US007838221B2

(12) United States Patent
Huletsky et al.

(10) Patent No.: US 7,838,221 B2
(45) Date of Patent: *Nov. 23, 2010

(54) **SEQUENCES FOR DETECTION AND IDENTIFICATION OF METHICILLIN-RESISTANT *STAPHYLOCOCCUS AUREUS* (MRSA)**

(75) Inventors: Ann Huletsky, Sillery (CA); Richard Giroux, Sillery (CA)

(73) Assignee: Geneohm Sciences, Inc., San Diego, CA (US)

( * ) Notice: Subject to any disclaimer, the term of this patent is extended or adjusted under 35 U.S.C. 154(b) by 352 days.

This patent is subject to a terminal disclaimer.

(21) Appl. No.: 11/248,438

(22) Filed: Oct. 11, 2005

(65) Prior Publication Data

US 2007/0082340 A1 Apr. 12, 2007

(51) Int. Cl.
*C12Q 1/68* (2006.01)
*G01N 33/53* (2006.01)
(52) U.S. Cl. ............................................ 435/6; 435/7.2
(58) Field of Classification Search ....................... None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 5,437,978 | A | 8/1995 | Ubukata et al. |
| 5,496,706 | A | 3/1996 | Kuusela et al. |
| 5,702,895 | A | 12/1997 | Matsunaga et al. |
| 5,776,712 | A | 7/1998 | Kuusela et al. |
| 5,780,610 | A | 7/1998 | Collins et al. |
| 5,866,366 | A | 2/1999 | Kallender |
| 6,090,592 | A | 7/2000 | Adams et al. |
| 6,117,635 | A | 9/2000 | Nazarenko et al. |
| 6,117,986 | A | 9/2000 | Nardone et al. |
| 6,156,507 | A | 12/2000 | Hiramatsu et al. |
| 2005/0019893 | A1 | 1/2005 | Huletsky et al. |
| 2006/0252078 | A1 | 11/2006 | Huletsky et al. |

FOREIGN PATENT DOCUMENTS

| | | |
|---|---|---|
| EP | 0 527 628 | 2/1993 |
| EP | 0887424 | 12/1998 |
| JP | 11056371 | 3/1999 |
| WO | WO 92/02638 | 8/1991 |
| WO | WO 92/05281 | 4/1992 |
| WO | WO 95/13395 | 5/1995 |
| WO | WO 01/23604 A2 | 4/2001 |
| WO | WO02/099034 | * 12/2002 |

OTHER PUBLICATIONS

U.S. Appl. No. 10/479,674, filed Sep. 2004, Huletsky.*
U.S. Appl. No. 11/545,986, filed Oct. 2006, Huletsky.*

Al-Soud, et al. "Capacity of nine thermostable DNA Polymerases to mediate DNA amplification in the presence of PCR-Inhibiting samples." *Appl. Environ. Microbiol.* 64(10): 3748-3753 (1998).
Al-Soud, et. al. "Effects of amplification facilitators on diagnostic PCR in the presence of blood, feces, and meat." *J. Clin. Microbiol.* 38(12): 4463-4470 (2002).
Arnheim, et al. "Polymerase Chain Reaction." C&EN. 36-47 (1990).
Archer and Niemeyer. "Origin and Evolution of DNA Associated with Resistance to Methicillin in *Staphylococci.*" Trends in Microbiology. 2(10):343-347 (1994).
Archer, et al. "Dissemination among *Staphylococci* of DNA Sequences Associated with Methicillin Resistance." Antimicrobial Agents and Chemotherapy. 38(3):447-54 (1994).
Baba et al., "Genome and Virulence Determinants of High Virulence Community-acquired MRSA." Lancet, England, May 25, 2002; vol. 359, No. 9320; pp. 1819-1827.
Barberis-Maino. IS431, a *Staphylococcai* insertion sequence-like element related to IS26 from *Proteus vulgaris*. Gene. 59:107-13 (1983).
Barringer, et al. "Blunt-end and single strand ligations by *Escherichia coli* ligase: influence on an in vitro amplification scheme." *Gene.* 89:117-122 (1990).
Berger-Bachi, et al. Insertional Inactivation of *Staphylococcal* Methicillin Resistance by Tn551. Journal of Bacteriology. 154(1):479-87 (1983).
Chakrabarti et al. "Novel Sulfoxides Facilitate GC-Rich Template Amplification." *Biotechniques.* 32: 866-874 (2002).
Database EMBL 'Online! May 14, 2001; retrieved from EBI, Database Accession No. AB037671, XP002238391.
Database EMBL 'Online! Jan. 7, 2000; retrieved from EBI Database Accession No. AB014433; XP002238392.
De Lencastre et al. Methicillin-Resistant *Staphylococcus aureus* disease in a Portuguese Hospital: Characterization of clonal Types by a Combination of DNA Typing Methods. Eur. *J. Clin. Microbiol. Infect. Dis.* 13: 64-73 (1994).
Deplano et al. "In Vivo deletion of the methicillin resistance *mec* region from the chromosome of I *Staphylococcus aureus* strains." *J. Antimicrob. Chemotherapty*, 46-617-619 (2000).
Derbise et al. "Mapping the Regions Carrying the Three Contiguous Antibiotic Resistance Genes *aadE, sat4*, and *aphA-3* in the Genomes of *Staphylococci*." Antimicrobial Agents and Chemotherapy. 41(5): 1024-32 (1997).
Dubin et al., "Physical Mapping of the *mec* Region of an American Methicillin-Resistant *Staphylococcus aureus* Strain." Antimicrobial Agents and Chemotherapy. 35(8):1661-65 (1991).
Egholm et al. "PNA hybridizes to complementary oligoncleotides obeying the Watson-Crick hydrogen-bonding rules." *Nature.* 365: 566-568 (1993).
Elghanian et al. "Selective Colorimetric Detection of Polynucleotides Based on the Distance-Dependent Optical Properties of Gold Nanoparticles." (1997) Science 277:1078-1081.

(Continued)

Primary Examiner—Steven C Pohnert
(74) *Attorney, Agent, or Firm*—Knobbe Martens Olson & Bear LLP

(57) ABSTRACT

Described herein are novel SCCmec right extremity junction (MREJ) sequences for the detection and/or identification of methicillin-resistant *Staphylococcus aureus* (MRSA). Disclosed are methods and compositions based on DNA sequences for the specific detection of MREJ sequences designated types xi, xii, xiii, xiv, xv, xvi, xvii, xviii, xix, and xx for diagnostic purposes and/or epidemiological typing.

14 Claims, 25 Drawing Sheets

OTHER PUBLICATIONS

Flores et. al. "A rapid, inexpensive method for eluting DNA from Agarose or Acrylamide gel slices without toxic or chaotropic materials." *Biotechniques*. 13: 205-206 (1992).

GenBank accession No. AB014440, version AB014440.1, Jul. 6, 1999, Ito et al.

GenBank accession No. AB063172, version AB063172.2, Jun. 12, 2001, Ito et al.

GenBank accession No. AB121219, version AB121219.1, Sep. 26, 2003, Ito et al.

GenBank accession No. AF270046, version AF270046.1, May 22, 2000, Taylor et al.

GenBank accession No. BK001539, version BK001539.1, Aug. 15, 2003, Mongkolrattanothai et al.

GenBank accession No. BX571856, version BX57156.1, Jun. 23, 2004, Holden et al.

GenBank accession No. U10927, version U10927.2, Nov. 1, 2001, Lin et al.

GenBank accession No. AF422691, version AR422691.1, Apr. 29, 2002, Oliveira et al.

GenBank accession No. AF411934, version AF411934.1, Mar. 5, 2002, Oliveira et al.

Gerberding, et al. Comparison of conventional susceptibility Tests with Direct Detection of Penicillin-Binding Protein 2a in borderline Oxacillin-Resistant Strains of *Staphylococcus aureus*. Antimicrobial Agents and Chemotherapy. 35(12):2574-79 (1991).

Guatelli, et al. "Isotherma, in vitro amplification of nucleic acids by a multenzyme reaction modeled after retroviral replication." *Proc. Natl. Acad. Sci. USA*, 87:1874-1878 (1990).

Hiramatsu et al. "Analysis of Borderline-Resistant Strains of Methicillin-Resistant *Staphylococcus aureus* Using Polymerase Chain Reaction." *Microbiol. Immunol*. 36: 445-453 (1992).

Hiramatsu et al., "Genetic Basis for Molecular Epidemiology of MRSA" J. Infect. Chemother. 1996, 2:117-129. XP001122060.

Hiramatsu, et al. "The emergence and evolution of methicillin-resistant *Staphylococcus aureus*." *Trends in Microbiology*. 9(10): 486-493 (2001).

Hiramatsu, et al. "Molecular Cloning and Nucleotide Sequence Determination of the Regulator Region of *mecA* gene in methicillin-resistant *staphylococcus aureus*." FEBS. 298(2.3):133-36 (1992).

Huletsky, et al. "New Real-Time PCR Asay for Rapid Detection of Methicillin-Resistant *Staphylococcus aureus* Directly from Specimens Containing a Mixture of *Staphylococci*." Journal of Clinical Microbiology. 42(5): 1875-84 (2004).

Inglis, et al. "Induced deletions within a cluster of resistance genes in the *mec* region of the chromosome of *Staphylococcus aureus*." *Gen. Microbiol*. 136:2231-2239 (1990).

Inglis, et al. "Methicillin-Sensitive and Resistant Homologues of *Staphylococcus aureus* Occur together among Clinical Isolates." J. Infect. Dis. N167:323-328 (1993).

Ito et al. "Acquisition of Methicillin Resistance and Progression of Multiantibiotic Resistance in Methicillin- Resistant *Staphylococcus aureus*." Yonsei Medical Journal. 39(6):526-33 (1998).

Ito et al. Novel Type V *Staphylococcal* Cassette Chromosome *mec* Driven by a Novel Cassette Chromosome Recombinase, ccrC. Antimicrob. Agents Chemother. 48:2637-2651 (2004).

Ito et al., "Cloning and Nucleotide Sequence Determination of the entire mvc DNA of pre-methicillin-resistant *Staphylococcus Aureus* N315," Antimicrob. Agents Chemother. US, Jun. 1999; vol. 43, No. 6, pp. 1449-1468. XP002238386;ISSN: 0066-4804.

Ito et al., "Structural Comparison of Three Types of *Staphylococcal* Cassette Chromosome Med Integrated in the Chromosome in Methicillini-resistant *Staphylococcus Aureaus*." Antimicrob. Agents Chemother. U.S. May, 2001, 45:1323-1336.

Katayama, et al. "A New Class of Genetic Element, *Staphylococcus* Cassette Chromosome *mec*, Encodes Methicillin resistance in *Staphylococcus aureus*." Antimicrob. Agents Chemother. 44(6):1549-1555 (2000).

Kellogg, et al. "TaqStart Antibody™ : "Hot Start" PCR facilitated by a neutralizing monoclonal antibody directed against *Taq* DNA Polymerase." *Biotechniques*. 16:1134-1137 (1994).

Kimmel, et al. "Preparations of cDNA and the Generation of cDNA Libraries: Overview." Methods in Enzymology. 152:307-316 (1987).

Kitagawa, et al. "Rapid Diagnosis of Methicillin-Resistant *Staphylococcus aureus* Bacteremia by Nested Polymerase Chain Reaction." Annals of Surgery. 224(5):665-71 (1996).

Kluytmans. Food-Initiated Outbreak of Methicillin-Resistant *Staphylococcus aureus* Analyzed by Pheno and Genotyping. Journal of clinical Microbiology. 33(5):1121-28 (1995).

Koshkin, et al. "LNA (locked nucleic acids): Synthesis of the Adenine, Cytosine, Guanine, 5-Methylcytosine, Thymine and Uracil Bicyclonucleoside Monomers, Oligomerisation, and unprecedented nucleic acid recognition." *Tetrahedron*. 54:3607-3630 (1998).

Kuroda, et al. "Whole genome sequencing of methicillin-resistant *Staphylococcus aureus*." *The Lancet*. 357: 9264; pp. 1225-1240, (2001).

Kwoh, et al. "Transcription-based amplification system and detection of amplified human immunodeficiency virus type 1 with a bead-based sandwich hybridization format." Proc. Natl. Acad. Sci. USA 86:1173-1177 (1989).

Landegren, et al. "A Ligase-Mediated Gene Detection Technique." (1988) Science 241:1077-1080.

Lawrence et al. "Consecutive isolation of homologous strains of methicillin-resistant and methicillin-susceptible *Staphylococcus aureus* from a hospitalized child." *J. Hosp. Infect*. 33:49-53 (1996).

Lawrence et al. "Use of the Coagulase Gene Typing Method for Detection of Carriers of Methicillin-Resistant Staphylococcus aureus." *Journal of Antimicrobial Chemotherapy*. 37:687-696 (1996).

Leach et al. "Theoretical Investigations of Novel Nucleic Acid Bases." (1992) J. Am. Chem. Soc. 114:3675-3683.

Lin et al. "Sequence Analysis and Molecular Characterization of Genes Required for the Biosynthesis of Type 1 Capsular Polysaccharide in *Staphylococcus aureus*." Journal of Bacteriology. 176(22):7005-16 (1994).

Lomell, et al. "Quantitative Assays Based on the Use of Replicatable Hybridization Probes." Clinical Chemistry. 35(9):1826-1831 (1989).

Luchansky and Pattee. "Isolation of Transposon Tn551 Insertions Near Chromosomal Markers of Interest in *Staphylococcus aureus*." Journal of Bacteriology. 159(3):894-99 (1984).

Luijendijk, et al. "Comparison of Five Tests for Identification of *Staphylococcus aureus* Clinical Samples." Journal of Clinical Microbiology. 34(9):2267-69 (1996).

Luong, et al. "Type I Capsule Genes of *Staphylococcus aureus* Are Carried in a *Staphyloccal* Cassette Chromosome genetic Element." Antimicrobial Agents and Chemotherapy. 46(4):1147-52 (2002).

Ma et al, "Novel Type of *Staphylococcal* Cassette Chromosome Mec Identified in Community-acquired Methicillin-resistant *Staphylococcus Aureus* Strains." Antimicrob. Agents Chemother. vol. 46, No. 4, Apr. 2002, pp. 1147-1152.

Mantsch et al. "Structural and Enzymatic Properties of Adenine 1-Oxide Nucleotides." (1975) Biochem. 14(26):5593-5601.

Martineau, et. al. "Correlation between the Resistance Genotype Determined by Multiplex PCR Assays and the Antibiotic Susceptibility Patterns of *Staphylococcus aureaus* and *Staphylococcus epidermis*." *Antimicrob. Chemotherapy*. 44(2): 231-238 (2000).

Mulligan, et al. "Methicillin-Resistant *Staphylococcus aureus*: a Consensus Review of the Microbiology, Pathogenesis, and Epidemiology with Implications for Prevention and Management." Am J Med. 94(3):313-28 (1993).

Murakami, et al. "Identification of Methicillin-Resistant Strains of *Staphylococci* by Polymerase Chain Reaction." *J. Clin Microbiol*. 29(10):2240-2244 (1991).

Muraki. Detection of Methicillin-Resistant *Staphylococcus aureus* using PCR and non-radioactive DNA probes (II). Rinsho Byori. 41(10): 1159-66 (1993).

Newton et al. "Instrumentation, Reagents and Consumables." PCR, 2nd Ed., Springer-Verlag (New York: 1997), Chapter 2, p. 8-28.

Nichols, et al. "A universal nucleoside for use at ambiguous sites in DNA primers." *Nature*. 369:492-493 (1994).

Oliveira et al., "Genetic Organization of the Downstream Region of the mecA Element in Methicillin-resistant Staphylococcus Aureus Isolates Carrying Different Polymorphisms of this Region," Antimicrobial Agents and Chemotherapy. US, Jul. 2000, vol. 44, No. 7, pp. 1906-1910; XP002238385; ISSN:0066-4804.

Oliveira, et al. "Multiplex PCR Strategy for Rapid Identification of Structural Types and Variants of the *mec* Element in Methicillin-Resistant *Staphylococcus aureus*." Antimicrob. Agents Chemother. 46:2155-2161 (2002).

Oliveira et al., "The Evolution of Pandemic Clones of Methicillin-resistant *Staphylococcus Aureus*: Identification of Two Ancestral Genetic Backgrounds and the Associated mec Elements." Microb. Drug Resist. vol. 7, No. 4, Jan. 2001, pp. 349-361.

Oliveira et al. "Secrets of success of a human pathogen: molecular evolution of pandemic clones of meticillin-resistant *Staphylococcus aureus*." Lancet Infect Dis. 2:180-9 (2002).

Partial International Search Report for International Application No. PCT/CA 02/00824 dated May 12, 2003.

Pattee, et al. "Genetic and Physical Mapping of the Chromosome of *Staphylococcus aureus*." Molecular Biology of the *Staphylococci*. VCH Publishers. 41-58 (1990).

Piccirilli et al. "Enzymatic incorporation of a new base pair into DNA and RNA extends the genetic alphabet." (1990) Nature. 343:33-37.

Saito, et. al. "Immunological Detection of Penicillin-Binding Protein 2' of Methicillin-Resistant *Staphylococci* by Using Monoclonal Antibodies Prepared from Synthetic Peptides." *J. Clin. Microbiol.* 33(9): 2498-2500 (1995).

Simor, et al. "Characterization and Proposed Nomenclature of Epidemic Strains of Methicillin-Resistant *Staphylococcus Aureus* in Canada." *CCDR* 25-12: 105-112 (Jun. 15, 1999).

Sooknanan, R. NASBA. A detection and amplification system uniquely suited for RNA. (1995) Biotechnology 13:563-564.

Stewart, et al. "IS257 and Small Plasmid Insertions in the *mec* Region of the Chromosome of *Staphylococcus aureus*." Plasmid. 31:12-20 (1994).

Suzuki, et al. "Distribution of *mec* Regulator Genes in Methicillin-Resistant *Staphylococcus* Clinical Strains." Antimicrobial Agents and Chemotherapy. 37(6):1219-26 (1993).

Suzuki, et al. "Survey of Methicillin-Resistant Clinical Strains of Coagulase-Negative *Staphylococci* for *mecA* Gene Distribution." *Antimicrob. Agents Chemother*. 36(2): 429-434 (1992).

Switzer et al. "Enzymatic Recognition of the Base Pair between Isocytidine and Isoguanosine." (1993) Biochemistry 32:10489-10496.

Thewell, et al. "Mode of action and application of Scorpion primers to mutation detection." (2000), Nucl. Acids Res. 28(19):3752-3761.

Tokue, et al. "Comparison of a Polymerase Chain Reaction Assay and a Convetional Microbiologic Method for Detection of Methicillin-Resistant *Staphylococcus aureus*." Antimicrobial Agents and Chemotherapy. 36(1):6-9 (1992).

Tor et al. "Site-Specific Enzymatic Incorporation of an Unnatural Base, $N^6$-(6-Aminohexyl)isoguanosine, into RNA." (1993) J. Am. Chem. Soc. 115:4461-4467.

Tyagi et al. "Molecular Beacons: Probes that Fluoresce upon Hybridization." (1996) Nat. Biotech. 14:303-308.

Ubukata, et. al. "Homology of *mecA* Gene in Methicillin-Resistant *Staphylococcus aureus* to that of *Staphylococcus aureus*." *Antimicrob, Agents Chemother*. 34(1):170-172 (1990).

Ubukata, et. al. "Rapid Detection of the *mecA* Gene in Methicillin-Resistant *Staphylococci* by Enzymatic Detection of Polymerase Chain Reaction Products." *J. Clin. Microbiol*. 30(7):1728-1733 (1992).

Ubukata, et. al. "Restriction Maps of the Regions Coding for Methicillin and Tobramycin Resistances on Chromosomal DNA in Methicillin-Resistant *Staphylococci*." Antimicrobial Agents and Chemotherapy. 33(9):1624-26 (1989).

Unal, et al. "Detection of Methicillin-Resistant Staphylococci by Using the Polymerase Chain Reaction." Journal of Clinical Microbiology. 30(7):1685-91 (1992).

Unal, et al. "Comparison of Tests for Detection of Methicillin-Resistant *Staphylococci aureus* in a Clinical Microbiological Laboratory." Antimicrobial Agents and Chemotherapy. 38(2):345-47 (1994).

Van Belkum, et al. "Comparison of Phage Typing and DNA Fingerprinting by Polymerase Chain Reaction of Discrimination of Methicillin-Resistant *Staphylococcus aureus* Strains." Journal of Clinical Microbiology. 31(4):798-803 (1993).

Van Brunt, J. "Amplifying Genes: PCR and its Alternatives." Biotechnology, 8:291-294 (1990).

Vannuffel, et al. "Specific Detection of Methicillin-Resistant *Staphylococcus* Species by Multiplex PCR." Journal of Clinical Microbiology. 33(11):2864-67 (1995).

Wada, et al. "Southern Hybridization Analysis of the mecA Deletion from Methicillin-Resistant *Staphylococcus aureus*." Biochem. Biophys. Res. Comm., 176: 1319-1326 (1991).

Wallet, et al. "Choice of a Routine Method for Detecting Methicillin-Resistance in *Staphylococci*." Journal of Antimicrobial Chemotherapy. 37:901-909 (1996).

Westin, et al. "Anchored multiplex amplification on a microelectronic chip array." *Nat. Biotechnol*. 18:199-204 (2000).

Wilson, Ian. "Inhibition and Facilitation of Nucleic Acid Amplification." *Appl. Environ. Microbiol*. 63: 3741-3751 (1997).

Wu, et al. "Genetic Organization of the *mecA* Region in Methicillin-Susceptible and Methicillin-Resistant Strains of *Staphylococcus sciuri*." Journal of Bacteriology. 180(2):236-42 (1998).

Wu, et a. "The Ligation Amplification Reaction (LAR)-Amplification of Specific DNA Sequences Using Sequential Rounds of Template-Dependent Ligation." (1989) Genomics 4:560-569.

Holden, et al. "Complete genomes of two clinical *Staphylococcus aureus* strains: Evidence for the rapid evolution of virulence and drug resistance." PNAS. 101(26):9786-9791 (2004).

International Search Report for International Application No. PCT/US06/39996 dated Nov. 23, 2007.

Zhang, et al. "Genome-based analysis of virulence genes in a non-biofilm-forming *Staphylococcus* epidermidis strain (ATCC 12228)." Molecular Microbiology. 49(6): 1577-1593 (2003).

\* cited by examiner

Figure 3 (continued).

| FIG. 3A | FIG. 3B |
| FIG. 3C | FIG. 3D |
| FIG. 3E | FIG. 3F |
| FIG. 3G | FIG. 3H |
| FIG. 3I | FIG. 3J |
| FIG. 3K | FIG. 3L |
| FIG. 3M | FIG. 3QN |
| FIG. 3O | FIG. 3P |
| FIG. 3Q | |

Page 1

SEQUENCES FOR DETECTION AND IDENTIFICATION OF METHICILLIN-RESISTANT *STAPHYLOCOCCUS AUREUS* (MRSA)

The Sequence Listing in electronic format entitled GENOM.057A.TXT was created on Jan. 12, 2008 and is 53.1 kilobytes in size. The information in the electronic format of the Sequence Listing is incorporated herein by reference in its entirety.

BACKGROUND OF THE INVENTION

1. Field of the Invention

The present invention relates to novel SCCmec right extremity junction sequences for the detection of methicillin-resistant *Staphylococcus aureus*, and uses thereof for diagnostic and/or epidemiological purposes.

2. Description of the Related Art

The coagulase-positive species *Staphylococcus aureus* is well documented as a human opportunistic pathogen (Murray et al. Eds, 1999, Manual of Clinical Microbiology, 7th Ed., ASM Press, Washington, D.C.). Nosocomial infections caused by *S. aureus* are a major cause of morbidity and mortality. Some of the most common infections caused by *S. aureus* involve the skin, and they include furuncles or boils, cellulitis, impetigo, and postoperative wound infections at various sites. Some of the more serious infections produced by *S. aureus* are bacteremia, pneumonia, osteomyelitis, acute endocarditis, myocarditis, pericarditis, cerebritis, meningitis, scalded skin syndrome, and various abcesses. Food poisoning mediated by staphylococcal enterotoxins is another important syndrome associated with *S. aureus*. Toxic shock syndrome, a community-acquired disease, has also been attributed to infection or colonization with toxigenic *S. aureus*.

Methicillin-resistant *S. aureus* (MRSA) emerged in the 1980s as a major clinical and epidemiologic problem in hospitals (Oliveira et al., 2002, Lancet Infect Dis. 2:180-9). MRSA are resistant to all β-lactams including penicillins, cephalosporins, carbapenems, and monobactams, which are the most commonly used antibiotics to cure *S. aureus* infections. MRSA infections can only be treated with more toxic and more costly antibiotics, which are normally used as the last line of defense. Since MRSA can spread easily from patient to patient via personnel, hospitals over the world are confronted with the problem to control MRSA. Consequently, there is a need to develop rapid and simple screening or diagnostic tests for detection and/or identification of MRSA to reduce its dissemination and improve the diagnosis and treatment of infected patients.

Methicillin resistance in *S. aureus* is unique in that it is due to acquisition of DNA from other coagulase-negative staphylococci (CNS), coding for a surnumerary β-lactam-resistant penicillin-binding protein (PBP), which takes over the biosynthetic functions of the normal PBPs when the cell is exposed to β-lactam antibiotics. *S. aureus* normally contains four PBPs, of which PBPs 1, 2 and 3 are essential. The low-affinity PBP in MRSA, termed PBP 2a (or PBP2'), is encoded by the choromosomal mecA gene and functions as a β-lactam-resistant transpeptidase. The mecA gene is absent from methicillin-sensitive *S. aureus* but is widely distributed among other species of staphylococci and is highly conserved (Ubukata et al., 1990, Antimicrob. Agents Chemother. 34:170-172).

Nucleotide sequence determination of the DNA region surrounding the mecA gene from *S. aureus* strain N315 (isolated in Japan in 1982), led to the discovery that the mecA gene is carried by a novel genetic element, designated staphylococcal cassette chromosome mec (SCCmec), which is inserted into the chromosome. SCCmec is a mobile genetic element characterized by the presence of terminal inverted and direct repeats, a set of site-specific recombinase genes (ccrA and ccrB), and the mecA gene complex (Ito et al., 1999, Antimicrob. Agents Chemother. 43:1449-1458; Katayama et al., 2000, Antimicrob. Agents Chemother. 44:1549-1555). SCCmec is precisely excised from the chromosome of *S. aureus* strain N315 and integrates into a specific *S. aureus* chromosomal site in the same orientation through the function of a unique set of recombinase genes comprising ccrA and ccrB. Cloning and sequence analysis of the DNA surrounding the mecA gene from MRSA strains NCTC 10442 (the first MRSA strain isolated in England in 1961) and 85/2082 (a strain from New Zealand isolated in 1985) led to the discovery of two novel genetic elements that shared similar structural features of SCCmec. The three SCCmec have been designated type I (NCTC 10442), type II (N315) and type III (85/2082) based on the year of isolation of the strains (Ito et al., 2001, Antimicrob. Agents Chemother. 45:1323-1336). Hiramatsu et al. have found that the SCCmec DNAs are integrated at a specific site in the chromosome of methicillin-sensitive *S. aureus* (MSSA). The nucleotide sequence of the regions surrounding the left and right boundaries of SCCmec DNA (i.e. attL and attR, respectively), as well as those of the regions around the SCCmec DNA integration site (i.e. attBscc which is the bacterial chromosome attachment site for SCCmec DNA), were analyzed. Sequence analysis of the attL, attR attBscc sites revealed that attBscc is located at the 3' end of a novel open reading frame (ORF), orfX. orfX encodes a putative 159-amino acid polypeptide that exhibits sequence homology with some previously identified polypeptides of unknown function (Ito et al., 1999, Antimicrob. Agents Chemother. 43:1449-1458). Two new types of SCCmec, designated type IV and type V were recently described (Ma et al., 2002, Antimicrob. Agents Chemother. 46:1147-1152, Ito et al., 2004, Antimicrob Agents Chemother. 48:2637-2651, Oliveira et al., 2001, Microb. Drug Resist. 7:349-360). Sequence analysis of the right extremity of the new SCCmec type IV from *S. aureus* strains CA05 and 8/6-3P revealed that the sequences were nearly identical over 2000 nucleotides to that of type II SCCmec of *S. aureus* strain N315 (Ma et al., 2002, Antimicrob. Agents Chemother. 46:1147-1152; Ito et al., 2001, Antimicrob. Agents Chemother. 45:1323-1336). To date, sequence data for the right extremity of the SCCmec type IV from *S. aureus* strains HDE288 and PL72 is not publicly available (Oliveira et al., 2001, Microb. Drug Resist. 7:349-360).

Methods to detect and identify MRSA based on the detection of the mecA gene and *S. aureus*-specific chromosomal sequences have been described. (Saito et al., 1995, J. Clin. Microbiol. 33:2498-2500; Ubukata et al., 1992, J. Clin. Microbiol. 30:1728-1733; Murakami et al., 1991, J. Clin. Microbiol. 29:2240-2244; Hiramatsu et al., 1992, Microbiol. Immunol. 36:445-453). However, because the mecA gene is widely distributed in both *S. aureus* and coagulase-negative staphylococci, these methods are not always capable of discriminating MRSA from methicillin-resistant CNS. (See, Suzuki et al., 1992, Antimicrob. Agents. Chemother. 36:429-434). To address this problem, Hiramatsu et al. developed a PCR-based assay specific for MRSA that utilizes primers that hybridize to the right extremities of the 3 types of SCCmec DNAs in combination with primers specific to the *S. aureus* chromosome, which corresponds to the nucleotide sequence on the right side of the SCCmec integration site. (U.S. Pat. No. 6,156,507, hereinafter the "'507 patent"). Nucleotide sequences surrounding the SCCmec integration site in other staphylococcal species (e.g., *S. epidermidis* and *S. haemolyticus*) are different from those found in *S. aureus*, therefore, this PCR assay is specific for the detection of MRSA.

The PCR assay described in the '507 patent also led to the development of "MREP typing" (mec right extremity polymorphism) of SCCmec DNA (Ito et al., 2001, Antimicrob. Agents Chemother. 45:1323-1336; Hiramatsu et al., 1996, J. Infect. Chemother. 2:117-129). The MREP typing method takes advantage of the fact that the nucleotide sequences of the three MREJ types differ at the right extremity of SCCmec DNAs adjacent to the integration site among the three types of SCCmec. Compared to type I, Type III has a unique nucleotide sequence while type II has an insertion of 102 nucleotides to the right terminus of SCCmec. The MREP typing method described by Hiramatsu et al. uses the following nomenclature: SCCmec type I is MREP type i, SCCmec type II is MREP type ii, and SCCmec type III as MREP type iii.

Because SCCmec types II and IV have the same nucleotide sequence to the right extremity, the MREP typing method described above cannot differentiate the new SCCmec type IV described by Hiramatsu et al. (Ma et al., 2002, Antimicrob. Agents Chemother. 46:1147-1152) from SCCmec type II.

The phrase MREJ refers to the mec right extremity junction <<mec right extremity junction>>. MREJ's are approximately 1 kilobase (kb) in length and include sequences from the SCCmec right extremity as well as bacterial chromosomal DNA to the right of the SCCmec integration site. Strains that were classified as MREP types i-iii correspond to MREJ types i-iii. MREJ types iv, v, vi, vii, viii, ix, and x have been previously characterized. (Huletsky et al., 2004, J Clin. Microbiol. 42:1875-1884, International Patent Application PCT/CA02/00824).

The embodiments described herein relate to the generation of SCCmec right extremity junction sequence data that enables the detection of more MRSA strains in order to improve NAT assays for detection of MRSA. There is a need for developing more ubiquitous primers and probes for the detection of most MRSA strains around the world.

SUMMARY OF THE INVENTION

Provided herein are specific, ubiquitous and sensitive methods and compositions for determining the presence and/or amount of nucleic acids from all methicillin-resistant *Staphylococcus aureus* (MRSA) strains. Methods, compositions and kits are disclosed that enable the detection and quantification of novel MREJ types xi-xx.

Some aspects relate to a method to detect the presence of an MRSA bacterium in a sample comprising bacterial nucleic acids. MRSA strains have SCCmec nucleic acid insert comprising a mecA gene. The SCCmec insert renders the MRSA bacterium resistant to methicillin. The SCCmec is inserted into the bacterial DNA at the 3' end of the open reading frame orfX, creating a polymorphic right extremity junction (MREJ). At least one primer and/or probe specific for MRSA strains is provided, wherein the primer or probe hybridizes to a polymorphic MREJ nucleic acid of MREJ types xi to xx. The primer(s) and/or probe(s) are annealed with the nucleic acids of the sample. Annealed primer and/or probe indicates the presence of MREJ.

In preferred embodiments, more than one primer and/or probe is provided. The primers and/or probes can anneal to the MREJ nucleic acids under substantially the same annealing conditions. The primers and/or probes can be at least 10 nucleotides, 12 nucleotides, 14 nucleotides, 16 nucleotides, 18 nucleotides, 20 nucleotides, 25 nucleotides, or 30 nucleotides in length. The probes and primers can be used together in the same physical enclosure or in different physical enclosures.

In some embodiments, the primers and/or probes anneal with any one of the nucleic acids of SEQ ID NOs: 15, 16, 17, 18, 19, 20, 21, 25, 26, 39, 40, 41, 42, 55, and 56. In some embodiments, the primers and/or probes altogether can anneal with MREJ types xi to xx, such as SEQ ID NOs: 15, 15, 16, 17, 18, 19, 20, 21, 25, 26, 39, 40, 41, 42, 55, and 56. For example, in some embodiments, the primers and/or probes listed in Table 4 are used to detect MRSA bacteria comprising the following MREJ nucleic acid:

TABLE 4

| Primer/Probe SEQ ID NOs: | To Identify MREJ type |
| --- | --- |
| 30, 31, 32, 33, 34, 44, 45, 76 | xi |
| 30, 31, 32, 33, 35, 44, 45, 62 | xii |
| 29, 30, 31, 32, 33, 44, 45, 76 | xiii |
| 29, 30, 31, 32, 33, 44, 45, 59 | xiv |
| 24, 30, 31, 32, 33, 4, 45, 62 | xv |
| 36, 44 | xvi |
| 4, 30, 31, 32, 33, 44, 45, 62 | xvii |
| 7, 30, 31, 32, 33, 44, 45, 59 | xviii |
| 9, 30, 31, 32, 33, 44, 45, 59 | xix |
| 8, 30, 31, 32, 33, 44, 45, 59 | xx |

In some embodiments, primers and/or probes are provided that anneal under stringent conditions to more than one MREJ type strain. For example, in preferred embodiments, SEQ ID NOs: 31, 32, 33 are provided for the detection of MREJ types xi to xv and xvii to xx.

In further embodiments primers and/or probes are provided in pairs for the detection of at least one MRSA having MREJ of types xi to x. Accordingly, in some embodiments, at least one pair of oligonucleotides selected from the group consisting of SEQ ID NO's: 34/45, 34/30, 34/76, and 34/44 are provided for detection of MREJ type xi. In other embodiments, at least one pair of oligonucleotides selected from the group consisting of SEQ ID NOs: 35/45, 35/30, 35/62, and 35/44 are provided for detection of MREJ type xii. In yet other embodiments, at least one pair of oligonucleotides selected from the group consisting of SEQ ID NOs: 29/45, 29/30, 29/76, and 29/44 is provided for detection of MREJ type xiii. In still other embodiments, at least one pair of oligonucleotides selected from the group consisting of SEQ ID NOs: 29/45, 29/30, 29/59, and 29/44 is provided for detection of MREJ type xiv. In other embodiments, at least one pair of oligonucleotides selected from the group consisting of SEQ ID NOs: 24/45, 24/30, 24/62, and 24/44 is provided for detection of MREJ type xv. In yet other embodiments, the oligonucleotides of SEQ ID NOs: 36 and 44 are provided for detection of MREJ type xvi. In still other embodiments, at least one pair of oligonucleotides selected from the group consisting of SEQ ID NOs: 4/45, 4/30, 4/62, and 4/44 is provided for the detection of MREJ type xvii. In yet other embodiments, at least one pair of oligonucleotides selected from the group consisting of 7/45, 7/30, 7/59 and 7/44 is provided for the detection of MREJ type xviii. In other embodiments, at least one pair of oligonucleotides selected from the group consisting of 9/45, 9/30, 9/59 and 9/44 is provided for the detection of MREJ type xix. In yet other embodiments, at least one pair of oligonucleotides selected from the group consisting of SEQ ID NOs: 8/45, 8/30, 8/59, and 8/44 is provided for the detection of MREJ type xx.

In some embodiments, at least two pairs of primers are provided for the detection of more than one MREJ type.

In other preferred embodiments, the primers and/or probes listed in Table 5 are provided together to detect MRSA bacteria comprising the following MREJ nucleic acid:

TABLE 5

| Primer/Probe SEQ ID NOs: | To Identify MREJ type |
|---|---|
| 51, 30, 31, 32, 33 | xi |
| 52, 30, 31, 32, 33 | xii |
| 29, 30, 31, 32, 33 | xiii |
| 29, 30, 31, 32, 33 | xiv |
| 24, 30, 31, 32, 33 | xv |
| 36, 44 | xvi |
| 4, 30, 31, 32, 33 | xvii |
| 7, 30, 31, 32, 33 | xviii |
| 9, 30, 31, 32, 33 | xix |
| 8, 30, 31, 32, 33 | xx |

In further embodiments, the methods described above further comprise providing primers and/or probes specific for a determined MREJ type, and detecting an annealed probe or primer as an indication of the presence of a determined MREJ type.

In yet other embodiments, primers and/or probes specific for the SEQ ID NOs listed in Table 6 are provided to detect MRSA bacteria comprising the following MREJ nucleic acid:

TABLE 6

| Primer/Probe SEQ ID NOs: | To Identify MREJ type |
|---|---|
| 17, 18, 19 | xi |
| 20 | xii |
| 15, 25, 26 | xiii |
| 16 | xiv |
| 56 | xv |
| 21 | xvi |
| 55 | xvii |
| 39, 40 | xviii |
| 41 | xix |
| 42 | xx |

In some embodiments, the primers are used in an amplification reaction, such as polymerase chain reaction (PCR) and variants thereof such as nested PCR and multiplex PCR, ligase chain reaction (LCR), nucleic acid sequence-based amplification (NABSA), self-sustained sequence replication (3SR), strand displacement amplification (SDA), branched DNA signal amplification (bDNA), transcription-mediated amplification (TMA), cycling probe technology (CPT), solid-phase amplification (SPA), nuclease dependent signal amplification (NDSA), rolling circle amplification, anchored strand displacement amplification, solid phase (immobilized) rolling circle amplification, Q beta replicase amplification and other RNA polymerase medicated techniques.

In preferred embodiments, PCR is used to amplify nucleic acids in the sample.

In other embodiments, oligonucleotides of at least 10, 12, 14, 16, 18, 20, 25, or 30 nucleotides in length which hybridize under stringent conditions with any of nucleic acids of SEQ ID NOs: 15, 16, 17, 18, 19, 20, 21, 25, 26, 39, 40, 41, 42, 55, and 56, and which hybridize with one or more MREJ of types selected from xi to xx are also provided.

In other embodiments, primer and/or probe pairs are provided for the detection of MRSA of all of types xi to xx. For example, in certain embodiments, the primer pairs (or probes) listed in Table 7 are provided:

TABLE 7

| Primer/Probe SEQ ID NOs: | To Identify MREJ type: |
|---|---|
| 34/45, 34/30, 34/76, 34/44 | xi |
| 35/45, 35/30, 35/62, 35/44 | xii |
| 29/45, 29/30, 29/76, 29/44 | xiii |
| 29/45, 29/30, 29/59, 29/44 | xiv |
| 24/45, 24/30, 24/62, 24/44 | xv |
| 36/44 | xvi |
| 4/45, 4/30, 4/62, 4/44 | xvii |
| 7/45, 7/30, 7/59, 7/44 | xviii |
| 9/45, 9/30, 9/59, 9/44 | xix |
| 8/45, 8/30, 8/59, 8/44 | xx |

In further embodiments of the method described above, internal probes having nucleotide sequences defined in any one of SEQ ID NOs: 31, 32, and 33 are provided.

In still other embodiments, primers and/or probes used detection of MREJ types xi to xx are used in combination with primers and/or probes capable of detecting MRSA of MREJ types i to x, such as for example those primers and or probes disclosed in co-pending International Patent Application PCT/CA02/00824.

Other aspects of the invention relate to nucleotide sequences comprising at least one of the nucleic acids of SEQ ID NOs: 15, 16, 17, 18, 19, 20, 21, 25, 26, 39, 40, 41, 42, 55, and 56, or the complement thereof. Further embodiments relate to fragments of the nucleic acids of SEQ ID NOs: 15, 16, 17, 18, 19, 20, 21, 25, 26, 39, 40, 41, 42, 55, and 56, wherein the fragments comprise at least 30, 50, 100, 150, 200, 300, or 500 consecutive nucleotides of the nucleic acids of SEQ ID NOs: SEQ ID NOs: 15, 16, 17, 18, 19, 20, 21, 25, 26, 39, 40, 41, 42, 55, and 56, or the complements thereof. Further aspects relate to vectors comprising the nucleic acid sequences of SEQ ID NOs: 15, 16, 17, 18, 19, 20, 21, 25, 26, 39, 40, 41, 42, 55, and 56, as well as host cells, such as *E. coli* host cells, comprising vectors comprising the nucleic acid sequences of SEQ ID NOs: 15, 16, 17, 18, 19, 20, 21, 25, 26, 39, 40, 41, 42, 55, and 56.

Still other aspects relate to oligonucloetides that are at least 10, 12, 14, 16, 18, 20, 25 or 30 nucleotides in length that anneal to any one of SEQ ID NOs: 15, 16, 17, 18, 19, 20, 21, 25, 26, 39, 40, 41, 42, 55, and 56. For example, some embodiments are oligonucleotides that comprise the sequence of any one of SEQ ID NOs: 31, 32, or 33. Yet other embodiments relate to oligonucloetides that are at least 10, 12, 14, 16, 18, 20, 25 or 30 nucleotides in length that anneal to only one of SEQ ID NOs: 15, 16, 17, 18, 19, 20, 21, 25, 26, 39, 40, 41, 42, 55, and 56.

Yet other aspects relate to kits comprising primers and/or probes. The primers and/or probes can be at least 10, 12, 14, 16, 18, 20, 25, or 30 nucleotides in length and hybridize with any one of the nucleic acids of MREJ type xi to xx. Further embodiments relate to kits comprising primers and/or probes that are at least 10, 12, 14, 16, 18, 20, 25, or 30 nucleotides in length and hybridize with any one of the nucleic acids of SEQ ID NOs: 15, 16, 17, 18, 19, 20, 21, 25, 26, 39, 40, 41, 42, 55, and 56. Some embodiments relate to kits that comprise primer pairs. For example, in some embodiments, the kits comprise the following primer pairs:

| Primer/Probe SEQ ID NOs: | To Identify MREJ type: |
|---|---|
| 34/45, 34/30, 34/76, 34/44 | xi |
| 35/45, 35/30, 35/62, 35/44 | xii |

-continued

| Primer/Probe SEQ ID NOs: | To Identify MREJ type: |
|---|---|
| 29/45, 29/30, 29/76, 29/44 | xiii |
| 29/45, 29/30, 29/59, 29/44 | xiv |
| 24/45, 24/30, 24/62, 24/44 | xv |
| 36/44 | xvi |
| 4/45, 4/30, 4/62, 4/44 | xvii |
| 7/45, 7/30, 7/59, 7/44 | xviii |
| 9/45, 9/30, 9/59, 9/44 | xix |
| 8/45, 8/30, 8/59, 8/44 | xx |

DETAILED DESCRIPTION OF THE INVENTION

Figure 1:
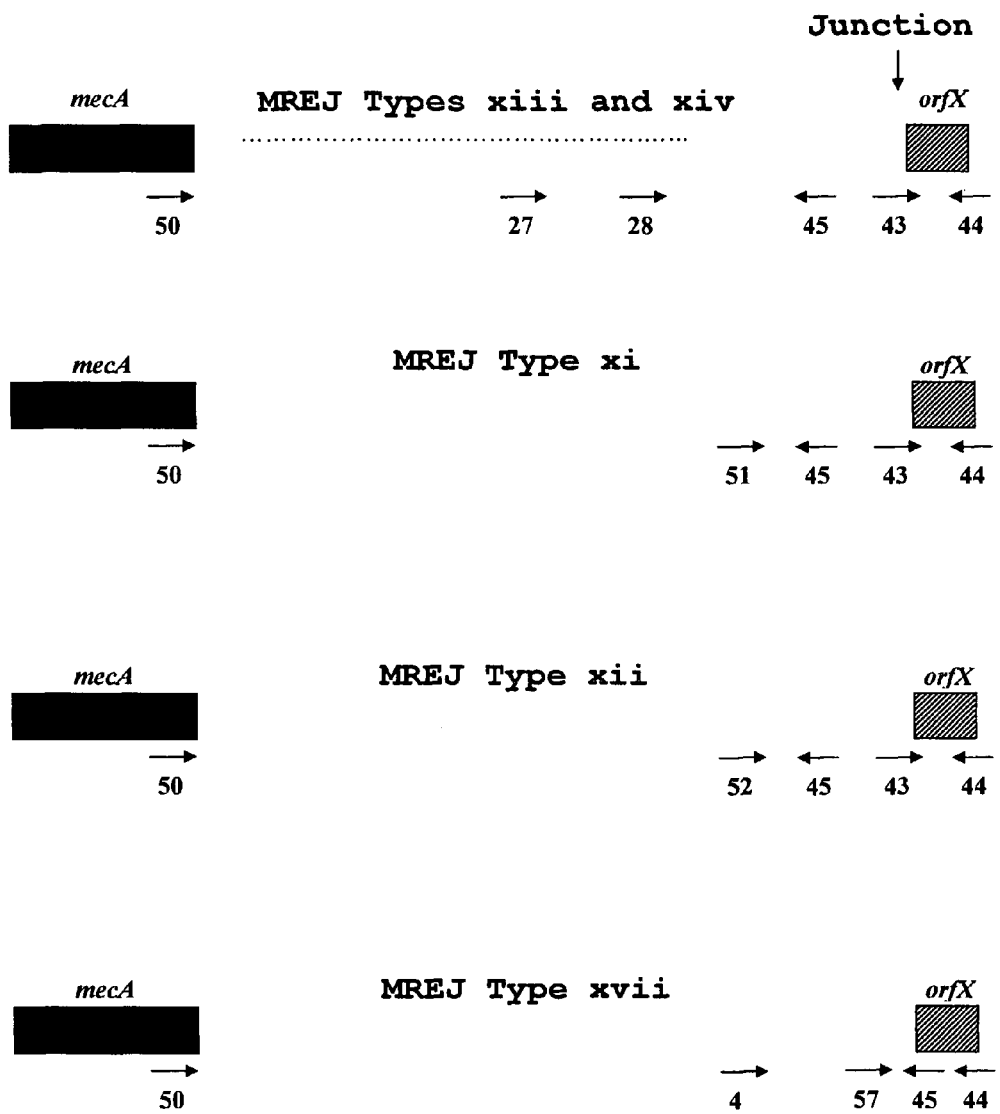
FIG. 1 depicts the SCCmec right extremity junctions. Shown are the positions and orientations of the primers used to sequence the novel MREJ types xi to xx. SEQ ID NOs.: 4, 24, 27-30, 36, 43-45, 50-57 were used to sequence MREJ types xi, xii, xiii, xiv, xv, xvi, xvii, xviii, xix, and xx. Arrows and numbers below indicate the positions of primers and their respective SEQ ID NOs. Walk indicates the positions where the DNA Walking ACP (DW-ACP) primers from the DNA Walking SpeedUp Kit (Seegene, Del Mar, Calif.) have annealed on the SCCmec sequence.
Figure 1:
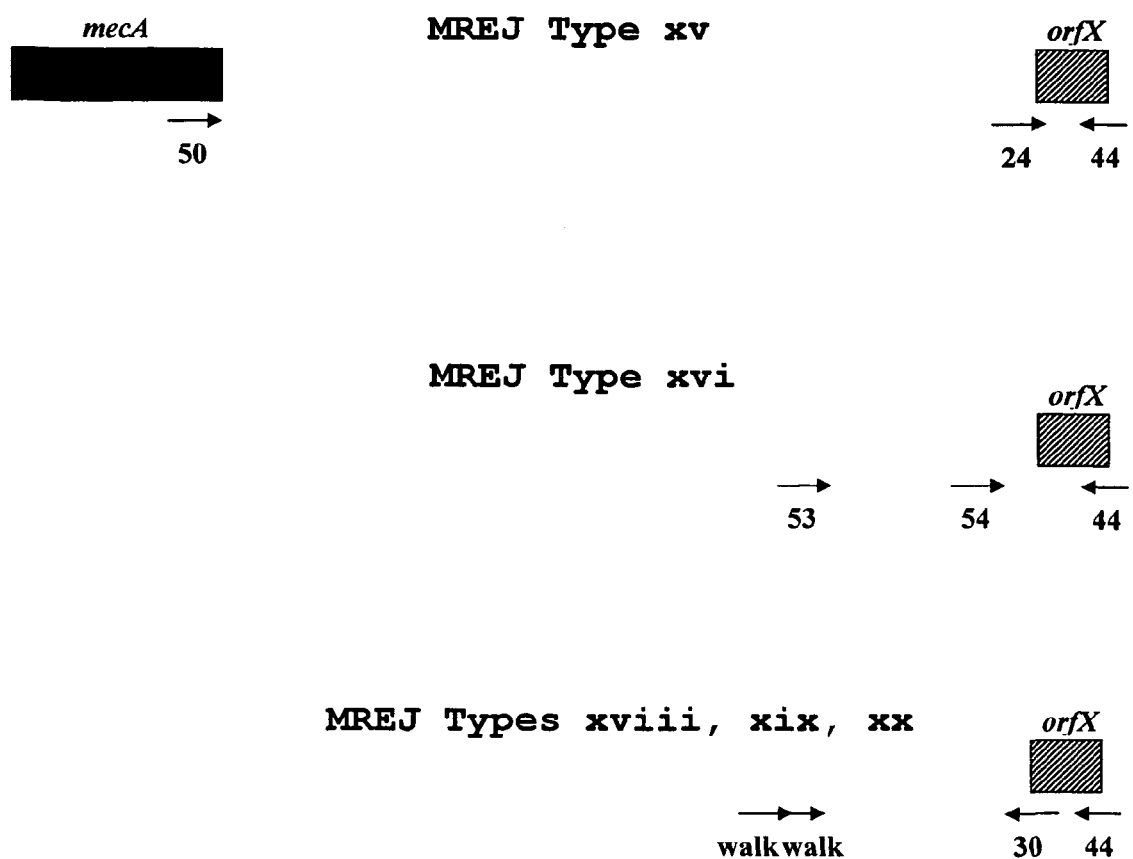

Methicillin resistant *Staphylococcus aureus* (MRSA) pose a serious health threat to individuals and the need for rapid and simple methods for the detection, identification, and quantification of MRSA is readily apparent.

Disclosed herein are novel DNA sequences and DNA arrangements present in MRSA strains that allow for the detection of MRSA that were undetectable using previously available methods. The novel DNA sequences and DNA arrangements are present at the SCCmec region of MRSA DNA. MRSA stains comprise an SCCmec insert that comprises a mecA gene. The SCCmec is inserted into the bacterial DNA at the 3' end of the orfX open reading frame. The insertion of the SCCmec into the bacterial DNA creates a polymorphic right extremity junction, hereinafter referred to as MREJ standing for <<mec right extremity junction>>. MREJ regions include sequences from the SCCmec right extremity, as well as chromosomal DNA adjacent to the right SCCmec integration site. Embodiments of the invention relate to the novel MREJ sequences and arrangements disclosed herein, which can be used as parental sequences from which primers and/or probes useful in the detection and identification of MRSA described below are derived. Other aspects of the invention relate to novel primers and/or probes derived from the novel MREJ sequences, as well as kits comprising primers and or probes that hybridize to MREJ types xi to xx, for the detection of MRSA.

Also disclosed herein are methods providing for the detection of the presence or absence of an MRSA strain in a sample that includes nucleic acids. At least one primer and/or probe that is specific for MRSA strains and that anneals to an MREJ nucleic acid of types xi to xx, disclosed herein, is provided. The primer(s) and/or probe(s) can be annealed to the nucleic acids of the sample. The detection of annealed primer(s) and/or probe(s) indicates the presence of an MRSA of the MREJ type that hybridizes to the primer(s) and/or probe(s).

Primers and Probes

As used herein, the terms "primer" and "probe" are not limited to oligonucleotides or nucleic acids, but rather encompass molecules that are analogs of nucleotides, as well as nucleotides. Nucleotides and polynucleotides, as used herein shall be generic to polydeoxyribonucleotides (containing 2-deoxy-D-ribose), to polyribonucleotides (containing D-ribose), to any other type of polynucleotide which is an N- or C-glycoside of a purine or pyrimidine base, and to other polymers containing nonnucleotidic backbones, for example, polyamide (e.g., peptide nucleic acids (PNAs)) and polymorpholino (commercially available from the Anti-Virals, Inc., Corvallis, Oreg., as Neugene™ polymers), and other synthetic sequence-specific nucleic acid polymers providing that the polymers contain nucleobases in a configuration which allows for base pairing and base stacking, such as is found in DNA and RNA.

The terms nucleotide and polynucleotide include, for example, 3'-deoxy-2',5'-DNA, oligodeoxyribonucleotide N3'→P5' phosphoramidates, 2'-O-alkyl-substituted RNA, double- and single-stranded DNA, as well as double- and single-stranded RNA, DNA:RNA hybrids, and hybrids between PNAs and DNA or RNA. The terms also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with a halogen, an aliphatic group, or are functionalized as ethers, amines, or the like. Other modifications to nucleotides or polynucleotides involve rearranging, appending, substituting for, or otherwise altering functional groups on the purine or pyrimidine base which form hydrogen bonds to a respective complementary pyrimidine or purine. The resultant modified nucleotide or polynucleotide may form a base pair with other such modified nucleotidic units but not with A, T, C, G or U. For example, guanosine (2-amino-6-oxy-9-beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidine) to form isocytosine (1-.beta.-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described U.S. Pat. No. 5,780,610 to Collins et al. The non-natural base pairs referred to as K and R., may be synthesized by the method described in Piccirilli et al. (1990) Nature 343:33-37 for the synthesis of 2,6-diaminopyrimidine and its complement (1-methylpyrazolo[4,3]-pyrimidine-5,7-(4H,6H)-dione. Other such modified nucleotidic units which form unique base pairs have been described in Leach et al. (1992) J. Am. Chem. Soc. 114:3675-3683 and Switzer et al., supra, or will be apparent to those of ordinary skill in the art.

Primers and/or probes can be provided in any suitable form, included bound to a solid support, liquid, and lyophilized, for example.

Specific binding or annealing of the primers and/or probes to nucleic acid sequences is accomplished through specific hybridization. It will be appreciated by one skilled in the art that specific hybridization is achieved by selecting sequences which are at least substantially complementary to the target or reference nucleic acid sequence. This includes base-pairing of the oligonucleotide target nucleic acid sequence over the entire length of the oligonucleotide sequence. Such sequences can be referred to as "fully complementary" with respect to each other. Where an oligonucleotide is referred to as "substantially complementary" with respect to a nucleic acid sequence herein, the two sequences can be fully complementary, or they may form mismatches upon hybridization, but retain the ability to hybridize under the conditions used to detect the presence of the MRSA nucleic acids.

A positive correlation exists between probe length and both the efficiency and accuracy with which a probe will anneal to a target sequence. In particular, longer sequences have a higher melting temperature ($T_m$) than do shorter ones, and are less likely to be repeated within a given target sequence, thereby minimizing promiscuous hybridization As used herein, "$T_m$" and "melting temperature" are interchangeable terms which refer to the temperature at which 50% of a population of double-stranded polynucleotide molecules becomes dissociated into single strands. Formulae for calculating the $T_m$ of polynucleotides are well known in the art. For example, the $T_m$ may be calculated by the following equation: $T_m=69.3+0.41$ x.(G+C) %−6−50/L, wherein L is the length of the probe in nucleotides. The $T_m$ of a hybrid polynucleotide may also be estimated using a formula adopted from hybridization assays in 1 M salt, and commonly used for calculating $T_m$ for PCR primers: [(number of A+T)× 2° C.+(number of G+C)×4° C.]. See, e.g, C. R. Newton et al. PCR, 2nd Ed., Springer-Verlag (New York: 1997), p. 24. Other more sophisticated computations exist in the art, which take structural as well as sequence characteristics into account for the calculation of $T_m$. A calculated $T_m$ is merely an estimate; the optimum temperature is commonly determined empirically.

Primer or probe sequences with a high G+C content or that comprise palindromic sequences tend to self-hybridize, as do their intended target sites, since unimolecular, rather than bimolecular, hybridization kinetics are generally favored in solution. However, it is also important to design a probe that contains sufficient numbers of G:C nucleotide pairings since each G:C pair is bound by three hydrogen bonds, rather than the two that are found when A and T (or A and U) bases pair to bind the target sequence, and therefore forms a tighter, stronger bond. Preferred G+C content is about 50%.

Hybridization temperature varies inversely with probe annealing efficiency, as does the concentration of organic solvents, e.g., formamide, which might be included in a hybridization mixture, while increases in salt concentration facilitate binding. Under stringent annealing conditions, longer hybridization probes, or synthesis primers, hybridize more efficiently than do shorter ones, which are sufficient under more permissive conditions. Preferably, stringent hybridization is performed in a suitable buffer under conditions that allow the reference or target nucleic acid sequence to hybridize to the probes. Stringent hybridization conditions can vary for example from salt concentrations of less than about 1 M, more usually less than about 500 mM and preferably less than about 200 mM) and hybridization temperatures can range (for example, from as low as 0° C. to greater than 22° C., greater than about 30° C. and (most often) in excess of about 37° C. depending upon the lengths and/or the nucleic acid composition of the probes. Longer fragments may require higher hybridization temperatures for specific hybridization. As several factors affect the stringency of hybridization, the combination of parameters is more important than the absolute measure of a single factor. "Stringent hybridization conditions" refers to either or both of the following: a) 6×SSC at about 45° C., followed by one or more washes in 0.2×SSC, 0.1% SDS at 65° C., and b) 400 mM NaCl, 40 mM PIPES pH 6.4, 1 mM EDTA, 50° C. or 70° C. for 12-16 hours, followed by washing.

In the methods described herein, detection of annealed primers and/or probes can be direct or indirect. For example, probes can be annealed to the sample being tested, and detected directly. On the other hand, primers can be annealed to the sample being tested, followed by an amplification step. The amplified products can be detected directly, or through detection of probes that anneal to the amplification products.

In some embodiments, more than one primer and/or probe is provided. For example, some embodiments relate to methods for detecting a plurality of MRSA strains comprising MREJ types xi to xx. A plurality of primers and/or probes may be used in reactions conducted in separate physical enclosures or in the same physical enclosure. Reactions testing for a variety of MRSA types can be conducted one at a time, or simultaneously. In embodiments where the plurality of primers is provided in the same physical enclosure, a multiplex PCR reaction can be conducted, with a plurality of oligonucleotides, most preferably that are all capable of annealing with a target region under common conditions.

In some embodiments, a plurality of primers and/or probes that are specific for different MREJ types are provided in a multiplex PCR reaction, such that the type of the MREJ can be determined. The primers and/or probes used for detection can have different labels, to enable to distinguish one MREJ type from another MREJ type. As used herein, the term "label" refers to entities capable of providing a detectable signal, either directly or indirectly. Exemplary labels include radioisotopes, fluorescent molecules, biotin and the like.

Although the sequences from orfX genes and some SCC-mec DNA fragments are available from public databases and have been used to develop DNA-based tests for detection of MRSA, the novel sequence data disclosed herein enable the detection of MRSA of MREJ types xi to xx, which heretofore were not detected using the assays known in the art. These novel sequences, which are listed in Table 8, could not have been predicted nor detected by PCR assays developed based on known MREJ sequences of MRSA (U.S. Pat. No. 6,156,507, International Patent Application PCT/CA02/00824, Ito et al., 2001, Antimicrob. Agents Chemother. 45:1323-1336, Huletsky et al., 2004, J Clin. Microbiol. 42:1875-1884, Ma et al, 2002, Antimicrob. Agents Chemother. 46:1147-1152, Ito et al, Antimicrob Agents Chemother. 2004. 48:2637-2651, Oliveira et al, 2001, Microb. Drug Resist. 7:349-360). Accordingly, the novel MREJ sequences improve current NAT assays for the diagnosis of MRSA as they enable the skilled artisan to design of primers and probes for the detection and/or identification of MRSA strains with MREJ types xi to xx.

Design and Synthesis of Oligonucleotide Primers and/or Probes

All oligonucleotides, including probes for hybridization and primers for DNA amplification, were evaluated for their suitability for hybridization or PCR amplification by computer analysis using publicly and commercially available computer software, such as the Genetics Computer Group GCG Wisconsin package programs, and the Oligo™ 6 and MFOLD 3.0 primer analysis software. The potential suitability of the PCR primer pairs was also evaluated prior to their synthesis by verifying the absence of unwanted features such as long stretches of one nucleotide and a high proportion of G or C residues at the 3' end (Persing et al., 1993, Diagnostic Molecular Microbiology: Principles and Applications, American Society for Microbiology, Washington, D.C.). Oligonucleotide amplification primers were synthesized using an automated DNA synthesizer (Applied Biosystems).

The oligonucleotide sequence of primers or probes may be derived from either strand of the duplex DNA. The primers or probes may consist of the bases A, G, C, or T or analogs and they may be degenerated at one or more chosen nucleotide position(s), using a nucleotide analog that pairs with any of the four naturally occurring nucleotides. (Nichols et al., 1994, Nature 369:492-493). Primers and probes may also contain nucleotide analogs such as Locked Nucleic Acids (LNA) (Koskin et al., 1998, Tetrahedron 54:3607-3630), and Peptide Nucleic Acids (PNA) (Egholm et al., 1993, Nature 365:566-568). Primers or probes may be of any suitable length, and may be selected anywhere within the DNA sequences from proprietary fragments, or from selected database sequences which are suitable for the detection of MRSA with MREJ types xi to xx. In preferred embodiments, the primers and/or probes are at least 10, 12, 14, 16, 18, 20, 25, or 30 nucleotides in length.

Variants for a given target microbial gene are naturally occurring and are attributable to sequence variation within that gene during evolution (Watson et al., 1987, Molecular Biology of the Gene, 4$^{th}$ ed., The Benjamin/Cummings Publishing Company, Menlo Park, Calif.; Lewin, 1989, Genes IV, John Wiley & Sons, New York, N.Y.). For example, different strains of the same microbial species may have a single or more nucleotide variation(s) at the oligonucleotide hybridization site. The skilled artisan readily appreciates the existence of variant nucleic acids and/or sequences for a specific gene and that the frequency of sequence variations depends on the selective pressure during evolution on a given gene product. Detection of a variant sequence for a region between two PCR primers may be achieved by sequencing the amplification product. On the other hand, to detect sequence variations that overlap with primer hybridization site, amplification and subsequent sequencing of a larger DNA target with PCR primers outside that hybridization site is required. Similar strategy may be used to detect variations at the hybridization site of a probe. Insofar as the divergence of the target nucleic acids and/or sequences or a part thereof does not affect significantly the sensitivity and/or specificity and/or ubiquity of the amplification primers or probes, variant MREJ sequences are contemplated, as are variant primer and/or probe sequences useful for amplification or hybridization to the variant MREJ.

Oligonucleotide sequences other than those explicitly described herein and which are appropriate for detection and/or identification of MRSA may also be derived from the novel MREJ sequences disclosed herein or selected public database sequences. For example, the oligonucleotide primers or probes may be shorter but of a length of at least 10 nucleotides or longer than the ones chosen; they may also be selected anywhere else in the MREJ sequences disclosed herein or in the sequences selected from public databases. Further, variants of the oligonucleotides disclosed herein can be designed. If the target DNA or a variant thereof hybridizes to a given oligonucleotide, or if the target DNA or a variant thereof can be amplified by a given oligonucleotide PCR primer pair, the converse is also true; a given target DNA may hybridize to a variant oligonucleotide probe or be amplified by a variant oligonucleotide PCR primer. Alternatively, the oligonucleotides may be designed from MREJ sequences for use in amplification methods other than PCR. The primers and/or probes disclosed herein were designed by targeting genomic DNA sequences which are used as a source of specific and ubiquitous oligonucleotide probes and/or amplification primers for MREJ types xi to xx. When a proprietary fragment or a public database sequence is selected for its specificity and ubiquity, it increases the probability that subsets thereof will also be specific and ubiquitous. Accordingly, although the selection and evaluation of oligonucleotides suitable for diagnostic purposes requires much effort, it is quite possible for the individual skilled in the art to derive, from the selected DNA fragments, oligonucleotides other than the ones listed in Tables 9, 10 and 11 which are suitable for diagnostic purposes.

The diagnostic kits, primers and probes disclosed herein can be used to detect and/or identify MRSA of MREJ types xi to xx, in both in vitro and/or in situ applications. For example, it is contemplated that the kits may be used in combination with previously described primers/probes detecting MRSA of MREJ types i to x. It is also contemplated that the diagnostic kits, primers and probes disclosed herein can be used alone or in combination with any other assay suitable to detect and/or identify microorganisms, including but not limited to: any assay based on nucleic acids detection, any immunoassay, any enzymatic assay, any biochemical assay, any lysotypic assay, any serological assay, any differential culture medium, any enrichment culture medium, any selective culture medium, any specific assay medium, any identification culture medium, any enumeration culture medium, any cellular stain, any culture on specific cell lines, and any infectivity assay on animals Samples may include but are not limited to: any clinical sample, any environmental sample, any microbial culture, any microbial colony, any tissue, and any cell line.

DNA Amplification

In some embodiments, an amplification and/or detection step follows the annealing step. Any type of nucleic acid amplification technology can be used in the methods described herein. Non-limiting examples of amplification reactions that can be used in the methods described herein include but are not restricted to: polymerase chain reaction (PCR) (See, PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y. (Innis)), ligase chain reaction (LCR) (See, Wu (1989) *Genomics* 4:560; Landegren (1988) *Science* 241: 1077; Barringer (1990) *Gene* 89:117), nucleic acid sequence-based amplification (NASBA), self-sustained sequence replication (3SR) (See, Guatelli (1990) *Proc. Natl. Acad. Sci. USA*, 87:1874), strand displacement amplification (SDA), branched DNA signal amplification bDNA, transcription-mediated amplification (TMA) (See, Kwoh (1989) *Proc. Natl. Acad. Sci. USA* 86:1173), cycling probe technology (CPT), nested PCR, multiplex PCR, solid phase amplification (SPA), nuclease dependent signal amplification (NDSA), rolling circle amplification technology (RCA), Anchored strand displacement amplification, solid-phase (immobilized) rolling circle amplification, Q Beta replicase amplification and other RNA polymerase mediated techniques (e.g., NASBA, Cangene, Mississauga, Ontario). These and other techniques are also described in Berger (1987) *Methods Enzymol.* 152:307-316; Sambrook, Ausubel, Mullis (1987) U.S. Pat. Nos. 4,683,195 and 4,683,202; Amheim (1990) *C&EN* 36-47; Lomell *J. Clin. Chem.*, 35:1826 (1989); Van Brunt, *Biotechnology*, 8:291-294 (1990); Wu (1989) *Gene* 4:560; Sooknanan (1995) *Biotechnology* 13:563-564.

In preferred embodiments, PCR is used to amplify nucleic acids in the sample. During DNA amplification by PCR, two oligonucleotide primers binding respectively to each strand of the heat-denatured target DNA from the microbial genome are used to amplify exponentially in vitro the target DNA by successive thermal cycles allowing denaturation of the DNA, annealing of the primers and synthesis of new targets at each cycle (Persing et al, 1993, Diagnostic Molecular Microbiology: Principles and Applications, American Society for Microbiology, Washington, D.C.).

Standard amplification protocols may be modified to improve nucleic acid amplification efficiency, including modifications to the reaction mixture. (Chakrabarti and Schutt, 2002, Biotechniques, 32:866-874; Al-Soud and Radstrom, 2002, J. Clin. Microbiol., 38:4463-4470; Al-Soud and Radstrom, 1998, Appl. Environ. Microbiol., 64:3748-3753; Wilson, 1997, Appl. Environ. Microbiol., 63:3741-3751). Such modifications of the amplification reaction mixture include but are not limited to the use of various polymerases or the addition of nucleic acid amplification facilitators such as betaine, BSA, sulfoxides, protein gp32, detergents, cations, and tetramethylamonium chloride.

Detection of Nucleic Acids

Detection of amplified nucleic acids may include any real-time or post-amplification technologies known to those skilled in the art. Classically, the detection of PCR amplification products is performed by standard ethidium bromide-stained agarose gel electrophoresis, however, the skilled artisan will readily appreciate that other methods for the detection of specific amplification products, which may be faster and more practical for routine diagnosis, may be used, such as those described in co-pending patent application WO01/23604 A2. Amplicon detection may also be performed by solid support or liquid hybridization using species-specific internal DNA probes hybridizing to an amplification product. Such probes may be generated from any sequence from the repertory of MREJ nucleic acids disclosed herein, and designed to specifically hybridize to DNA amplification. Alternatively, amplicons can be characterized by sequencing. See co-pending patent application WO01/23604 A2 for examples of detection and sequencing methods.

Other non-limiting examples of nucleic acid detection technologies that can be used in the embodiments disclosed herein include, but are not limited to the use of fluorescence resonance energy transfer (FRET)-based methods such as adjacent hybridization of probes (including probe-probe and probe-primer methods) (See, J. R. Lakowicz, "Principles of Fluorescence Spectroscopy," Kluwer Academic/Plenum Publishers, New York, 1999)., TaqMan probe technology (See, European Patent EP 0 543 942), molecular beacon probe technology (See, Tyagi et al., (1996) *Nat. Biotech.* 14:303-308.), Scorpion probe technology (See, Thewell (2000), *Nucl. Acids Res.* 28:3752), nanoparticle probe technology (See, Elghanian, et al. (1997) *Science* 277:1078-1081.) and Amplifluor probe technology (See, U.S. Pat. Nos. 5,866,366; 6,090,592; 6,117,635; and 6,117,986).

In preferred embodiments, molecular beacons are used in post-amplification detection of the target nucleic acids. Molecular beacons are single stranded oligonucleotides that, unless bound to target, exist in a hairpin conformation. The 5' end of the oligonucleotide contains a fluorescent dye. A quencher dye is attached to the 3' end of the oligonucleotide. When the beacon is not bound to target, the hairpin structure positions the fluorophore and quencher in close proximity, such that no fluorescence can be observed. Once the beacon hybridizes with target, however, the hairpin structure is disrupted, thereby separating the fluorophore and quencher and enabling detection of fluourescence. (See, Kramer F R., 1996, Nat Biotechnol 3:303-8.). Other detection methods include target gene nucleic acids detection via immunological methods, solid phase hybridization methods on filters, chips or any other solid support. In these systems, the hybridization can be monitored by any suitable method known to those skilled in the art, including fluorescence, chemiluminescence, potentiometry, mass spectrometry, plasmon resonance, polarimetry, colorimetry, flow cytometry or scanometry. Nucleotide sequencing, including sequencing by dideoxy termination or sequencing by hybridization (e.g. sequencing using a DNA chip) represents another method to detect and characterize the nucleic acids of target genes.

MREJ Nucleic Acids

The MREJ fragments disclosed herein were obtained as a repertory of sequences created by amplifying MRSA nucleic acids with novel primers. The amplification and sequencing primers, the repertory of MREJ sequences, and the oligonucleotide sequences derived therefrom for diagnostic purposes, disclosed in Tables 8-11 are further objects of this invention.

Aspects of the invention relate to nucleic acids, in particular nucleic acid sequences from DNA fragments of SCCmec right extremity junction (MREJ), including sequences from SCCmec right extremity and chromosomal DNA to the right of the SCCmec integration site in MRSA types xi to xx. Some embodiments relate to the parental sequences of MREJ types xi to xx from which primers and/or probes specific for the MREJ type xi to xx strain are derived. Thus, some embodiments relate to the nucleotide sequence of SEQ ID NO:15, 16, 17, 18, 19, 20, 21, 25, 26, 39, 40, 41, 42, 55, or 56 or the complement thereof. Other embodiments relate to DNA fragments and oligonucleotides, such as primers and probes. For example, some embodiments relate to nucleic acids comprising at least 10, 20, 30, 40, 50, 75, 100, 150, 200, 250, 300, 350, 400, 450, 500, 600, 700, or 800 consecutive nucleotides of the nucleic acids of SEQ ID NO: 15, 16, 17, 18, 19, 20, 21, 25, 26, 39, 40, 41, 42, 55, or 56.

The scope of this invention is not limited to the use of amplification by PCR, but rather includes the use of any nucleic acid amplification method or any other procedure which may be used to increase the sensitivity and/or the rapidity of nucleic acid-based diagnostic tests. The scope of the present invention also covers the use of any nucleic acids amplification and detection technology including real-time or post-amplification detection technologies, any amplification technology combined with detection, any hybridization nucleic acid chips or array technologies, any amplification chips or combination of amplification and hybridization chip technologies. Detection and identification by any nucleotide sequencing method is also under the scope of the present invention.

EXAMPLE 1

Evaluation of Previously Described MRSA Diagnostic Amplification Assays

Initially, the literature taught that five types of SCCmec right extremity sequences (SCCmec types I-V) are found among MRSA strains, based on DNA sequence homology. (See, Ito et al., 1999, Antimicrob. Agents Chemother. 43:1449-1458; Katayama et al., 2000, Antimicrob. Agents Chemother. 44:1549-1555; Ito et al., 2001, Antimicrob. Agents Chemother. 45:1323-1336, Ma et al., 2002, Antimicrob. Agents Chemother. 46:1147-1152, Ito et al, 2004, Antimicrob. Agents Chemother. 48:2637-2651). SCCmec DNAs are integrated at a specific site of the chromosome of a methicillin sensitive *Staphylococcus aureus* (MSSA), named orfX. Generally, each SCCmec type has a unique nucleotide sequence at the right extremity of the SCCmec cassette. The exception to this rule is seen with SCCmec types II and IV, which exhibit nearly identical sequence over 2000 nucleotides. However, SCCmec type II has an insertion of 102 nucleotides to the right terminus of SCCmec type I. Strains classified as SCCmec types I-III fall under the category of MREJ types i-iii.

Recently, we analyzed the MREJ regions of several MRSA strains. We described seven new sequences at the right extremity junction of SCCmec from MRSA that we named MREJ types iv, v, vi, vii, viii, ix, and x (Huletsky et al., 2004, J Clin. Microbiol. 42:1875-1884, International Patent Application PCT/CA02/00824).

We designed a real-time MRSA-specific multiplex PCR assay having primers that target the SCCmec portion of MREJ types i, ii, iii, iv, v, and vii with a primer targeting the *S. aureus* orfX. Three molecular beacon probes (MBPs) specific to the orfX sequence were used for detection of all sequence polymorphisms identified in this region of the orfX sequence (Huletsky et al., 2004, J. Clin. Microbiol. 42:1875-1884). The oligonucleotide of SEQ ID NO: 30, which hybridizes to the *S. aureus* orfX, and the oligonucleotides of SEQ ID NO's: 36, 70, 71, 72, and 74, which hybridize to the SCCmec portion of MREJ types i, ii, iii, iv, v, and vii were used in the PCR reaction. Oligonucleotides of SEQ ID NOs: 31, 32, and 33, which hybridize to *S. aureus* orfX were used as probes. The specificity and ubiquity (i.e., the ability to detect all or most MRSA strains) of the PCR assay was verified using a panel of 569 reference and clinical strains of methicillin sensivie *S. aureus* (MSSA) and 1657 different MRSA strains from 32 different countries and which include well-known epidemic clones.

A list of the strains tested and used to build the repertories of MREJ nucleic acids and oligonucleotides derived therefrom disclosed herein is presented in Table 1. The *S. aureus* clinical isolates used in this invention are part of the SENTRY program collection and several supplier's collections. These *S. aureus* reference strains or clinical isolates originate from 32 countries: African countries (n=15), Albania (n=2), Argentina (n=50), Australia (n=71), Austria (n=2), Belgium (n=10), Brazil (n=78), Canada (n=607), Chile (n=42), China (n=70), Denmark (n=33), Egypt (n=1), Finland (n=12), France (n=50), Germany (n=47), Greece (n=7), Ireland (n=5), Israel (n=19), Italy (n=61), Japan (n=62), Mexico (n=1), The Netherlands (n=179), Poland (n=33), Portugal (n=24), Singapore (n=20), Slovenia (n=12), Spain (n=31), Sweden (n=10), Switzerland (n=13), Turkey (n=28), United Kingdom (n=22), and United States (n=528). Confirmation of the identification of the staphylococcal strains was performed by using the MicroScan WalkAway Panel type Positive Breakpoint Combo 13 when required (Dade Behring Canada Inc., Mississauga, Ontario, Canada). When needed, the identity was reconfirmed by PCR analysis using *S. aureus*-specific primers and mecA-specific primers (SEQ ID NOs.: 50, 60, 61, 63) (Martineau et al., 2000, Antimicrob. Agents Chemother. 44:231-238). The data from the assay is presented in Table 2.

Among the 569 MSSA strains tested, 26 strains were misidentified as MRSA based on the PCR assay. Of the 1657 MRSA strains tested, 1640 were specifically detected with the PCR assay whereas 23 of these MRSA strains, representing a broad variety of origins were not detected by the assay. Thus, the specificity and ubiquity (i.e. the ability to detect all or most MRSA strains) of this PCR assay was verified. Four of these 23 MRSA strains, CCRI-9208, CCRI-9770, CCRI-9681, and CCRI-9860, which were not detected in the above assay have previously been shown to harbor the MREJ types vi, viii, ix, and x, respectively. (International Patent Application, PCT/CA02/00824).

The 19 remaining MRSA strains that were not detected in the assay were analyzed further. PCR was performed on the genomic DNA from each strain, using a primer targeting the sequence at the SCCmec right extremity of MREJ types vi, viii, or ix in combination with a primer targeting the *S. aureus* orfX Specifically, each PCR reaction contained the oligonucleotide of SEQ ID NO:65, which anneals to MREJ type vi, the oligonucleotide of SEQ ID NO:75, which anneals to MREJ type viii, or the oligonucleotide of SEQ ID NO:29, which anneals to MREJ type ix, in combination with the oligonucleotide of SEQ ID NO:30, which is *S. aureus* specific primer. MREJ type x was previously shown to have a deletion of the complete orfX and a portion at the right extremity of SCCmec type II. (International Patent Application PCT/CA02/00824). Therefore, the oligonucleotide of SEQ ID NO:77, which anneals to orf22 in the *S. aureus* chromosome, and the oligonucleotide of SEQ ID NO:73, which anneals to orf27 located in SCCmec type II were used in a PCR reaction to detect MREJ type x. Two out of 19 strains, CCRI-11879 and CCRI-12036, were shown to harbor MREJ type ix with these PCR primers. However, 17 MRSA strains were not detected with primers targeting MREJ types vi, viii, ix, and x suggesting that these strains harbor new MREJ types (Tables 2 and 3).

EXAMPLE 2

Sequencing of Novel MREJ Types from MRSA

To further characterize the MREJ region of the 17 MRSA strains from which DNA was not amplified with primers that allow the detection of MREJ types i to x, the nucleotide sequence of MREJ for 15 of these 17 MRSA strains was determined. First, a primer that anneals to mecA (SEQ ID NO.: 50) and a primer that anneals to the 5' end of orfX (SEQ ID NO.:44) were used in together in a PCR reaction to amplify MREJ fragments of MRSA. The strategy used to select these primers is illustrated in FIG. 1. Four identical PCR reactions, each containing 100 ng of purified genomic DNA were performed. Each PCR reaction contained IX HERCULASE™ DNA polymerase buffer (Stratagene, La Jolla, Calif.), 0.8 µM of each of the oligos of SEQ ID NOs.: 44 and 50, 0.56 mM of each of the four dNTPs and 5 units of HERCULASE™ DNA polymerase (Stratagene, La Jolla, Calif.) with 1 mM $MgCl_2$ in a final volume of 50 µl. PCR reactions were subjected to cycling using a standard thermal cycler (PTC-200 from MJ Research Inc.) as follows: 2 min at 92° C. followed by 35 or 40 cycles of 10 sec at 92° C. for the denaturation step, 30 sec at 55° C. for the annealing step and 15 min at 68° C. for the extension step.

The four PCR reactions were pooled. 10 µL of the PCR reaction was resolved by electrophoresis in a 0.7% agarose gel containing 0.25 µg/mL of ethidium bromide. The amplicons were then visualized with an Alpha-Imager (Alpha Innotech Corporation, San Leandro, Calif.) by exposing to UV light at 254 nm. The remaining PCR-amplified mixture (150-200 µl, total) was also resolved by electrophoresis in a 0.7% agarose gel and visualized by staining with methylene blue (Flores et al., 1992, Biotechniques, 13:203-205).

Of the 15 strains tested, the following eight yielded amplification products ranging from 12-20 kb in length with SEQ ID NOs.: 44 and 50 as primers: CCRI-11976, CCRI-11999, CCRI-12157, CCRI-12198, CCRI-12199, CCRI-12719, CCRI-9887, CCRI-9772. The amplification products were excised from the agarose gel and purified using the QIAquick™ gel extraction kit (QIAGEN Inc., Valencia, Calif.). The gel-purified DNA fragments were used directly in sequencing reactions. Both strands of the MREJ amplification products were sequenced by the dideoxynucleotide chain termination sequencing method using an Applied Biosystems automated DNA sequencer (model 377 or 3730xl) with their Big Dye™ Terminator Cycle Sequencing Ready Reaction Kit (Applied Biosystems, Foster City, Calif.). 425-495 ng of the gel-purified amplicons were used in sequencing reactions with SEQ ID NO.: 44, which was used for the amplification reaction. Based on the sequence information generated from the reactions with SEQ ID NO:44, internal sequencing primers were designed and used to obtain sequence data from both strands for a larger portion of each amplicon preparation. Specifically, the oligonulceotides of SEQ ID NOs.: 43 and 45 were used to sequence MRSA strains CCRI-11976 and CCRI-11999; SEQ ID NOs.: 43, 45, and 51 were used to sequence MRSA strains CCRI-12157, CCRI-12198, and CCRI-12199; SEQ ID NOs.: 43, 45, and 52 were used to sequence MRSA strain CCRI-12719; SEQ ID NO.: 24 was used to sequence MRSA strain CCRI-9887, and SEQ ID NOs.: 4, 45, and 57 were used to sequence MRSA strain CCRI-9772 (FIG. 1, Tables 9 and 11). The sequences of the 8 strains described in Table 3 are presented as SEQ ID NOs.: 15, 16, 17, 18, 19, 20, 55, and 56 (Table 8).

To ensure that the determined sequence did not contain errors attributable to the sequencing of PCR artifacts, two independent preparations of the gel-purified MREJ amplification products originating from two independent PCR amplifications were sequenced as described above. For most target fragments, the sequences determined for both amplicon preparations were identical. Furthermore, the sequences of both strands were 100% complementary thereby confirming the high accuracy of the determined sequence. The MREJ sequences determined using the above strategy are described in the Sequence Listing and in Table 8.

A different set of oligonucleotide primers (described in Oliviera et. al.) was used to further analyze the 17 MRSA strains that did not yield amplification products with primers for detection of MREJ types i-vii. (Oliveira and de Lencastre. 2002, Antimicrob. Agents Chemother. 46:2155-2161). Two strains, (CCRI-12382 and CCRI-12383), harbored SCCmec type III and contained sequences specific to the yccr complex. Another strain, (CCRI-12845), harbors SCCmec type II.

To determine the MREJ sequences of strains CCRI-12382 and CCRI-12383, a primer targeting the ψccr complex sequence located in SCCmec type III (SEQ ID NO.: 27) was used in combination with a primer targeting the 5'end of orfX (SEQ ID NO.: 44) to amplify MREJ fragments of these two MRSA strains (Table 10 and FIG. 1). Four identical PCR reactions, each containing 100 ng of purified genomic DNA were performed. Each PCR reaction contained IX HERCULASE™ DNA polymerase buffer (Stratagene, La Jolla, Calif.), 0.8 µM of each of the 2 primers (SEQ ID NOs.: 27 and 44), 0.56 mM of each of the four dNTPs and 5 units of HERCULASE™ DNA polymerase (Stratagene, La Jolla, Calif.) with 1 mM $MgCl_2$ in a final volume of 50 µl. The PCR reactions were cycled using a standard thermal cycler (PTC-200 from MJ Research Inc., Watertown, Mass.) as follows: 2 min at 92° C. followed by 35 cycles of 10 sec at 92° C. for the denaturation step, 30 sec at 55 C for the annealing step and 15 min at 68° C. for the extension step.

The PCR reactions were pooled and 10 µl of the PCR-amplified mixture was resolved by electrophoresis in a 0.7% agarose gel containing 0.25 µg/ml of ethidium bromide. The amplicons were then visualized with an Alpha-Imager (Alpha Innotech Corporation, San Leandro, Calif.) by exposing to UV light at 254 nm. The remaining PCR-amplified mixture (150-200 µl, total) was also resolved by electrophoresis in a 0.7% agarose gel and visualized by staining with methylene blue as described above. For these two MRSA strains, an amplification product of ~8 kb was obtained. The PCR amplification products were excised from the agarose gel and purified as described above. The gel-purified DNA fragment was then used directly in the sequencing protocol as described above. The sequencing reactions were performed by using SEQ ID NO.: 44 (also used in the amplification reaction) and 425-495 ng of the gel-purified amplicons for each reaction. Subsequently, different sets of internal sequencing primers were used to obtain sequence data from both strands and for a larger portion of the amplicon (SEQ ID NOs.: 28, 30, and 43) (FIG. 1, Tables 9 and 11). The sequence of the MRSA strains CCRI-12382 and CCRI-12383 described in Table 3 which were sequenced using this strategy are designated SEQ ID NOs.: 25 and 26, respectively (Table 8).

To sequence the MREJ fragment of strain CCRI-12845 (SCCmec type II) PCR amplification was performed using the oligonucleotide of SEQ ID NO:44, which anneals to the 5' end of orfX in combination with the oligonucleotide of SEQ ID NO:53, which anneals to the SCCmec right extremity of MREJ type ii. 1 µL of a purified genomic DNA preparation was transferred directly into 4 tubes containing 39 µL of a PCR reaction mixture. Each PCR reaction contained 50 mM KCl, 10 mM Tris-HCl (pH 9.0), 0.1% Triton X-100, 2.5 mM MgCl$_2$, 0,4 µM of each of the oligonucleotides of SEQ ID NO.: 44 and 53, 200 µM of each of the four dNTPs, 3.3 µg/µl of BSA (Sigma-Aldrich Canada Ltd) and 0.5 unit of Taq DNA polymerase (Promega, Madison, Wis.) coupled with the TaqStart™ Antibody (BD Bisociences, San Jose, Calif.). PCR reactions were performed using a standard thermocycler (PTC-200 from MJ Research Inc., Watertown, Mass.) as follows: 3 min at 94° C. followed by 40 cycles of 5 sec at 95° C. for the denaturation step, 1 min at 58° C. for the annealing step and 1 min at 72° C. for the extension step. An amplification product of 4.5 kb was obtained with this primer set.

The amplification products were pooled and 10 µl of the mixture were resolved by electrophoresis in a 1.2% agarose gel containing 0.25 µg/ml of ethidium bromide. The amplicons were then visualized with the Alpha-Imager. Amplicon size was estimated by comparison with a 1 kb molecular weight ladder (Life Technologies, Bethesda, Md.). The remaining PCR-amplified mixture (150 µl, total) was also resolved by electrophoresis in a 1.2% agarose gel and visualized by staining with methylene blue as described above. The PRC reaction yielded a 1.2 kb amplification product. The band corresponding to this specific amplification product was excised from the agarose gel and purified as described above. The gel-purified DNA fragment was then used directly in the sequencing protocol as described above. The sequencing reactions were performed using the oligonucleotides of SEQ ID NOs.: 44 and 53 as well as one internal primer (SEQ ID NO.: 54) and 10 ng/100 bp per reaction of the gel-purified amplicons (FIG. 1, Table 10). The MREJ sequence of strain CCRI-12845 is designated as SEQ ID NO.: 21 (Table 8).

To determine the MREJ sequences of the 4 last MRSA strains (CCRI-12524, CCRI-12535, CCRI-12810, and CCRI-12905), the oligonucleotide of SEQ ID NO:44 was used in combination with each of the four DNA Walking ACP (DW-ACP) primers from the DNA WALKING SPEED UP™ Sequencing Kit (Seegene, Del Mar, Calif.) according to the manufacturer's instructions on a PTC-200 thermocycler. The DW-ACP primer system (DW ACP-PCR™ Technology) enables one to obtain genuine unknown target amplification products up to 2 kb. A first amplification product obtained with one of the DW-ACP primers was purified using the QIAQUIK™ PCR purification Kit (QIAGEN Inc., Valencia, Calif.). The purified PCR product was re-amplified using the DW-ACP-N primer in combination with the oligonucleotide of SEQ ID NO:30, which anneals to orfX under manufacturer recommended PCR conditions. The PCR-amplified mixture of 4 different 50-µL PCR reactions were pooled and resolved by electrophoresis in a 1.2% agarose gel. The amplicons were then visualized by staining with methylene blue as described above. Amplicon size was once again estimated by comparison with a 1 kb molecular weight ladder. An amplification product of 1.5 to 3 kb was obtained. The amplification product was excised from the agarose gel and purified as described above and the DNA was then used directly in the sequencing protocol as described above. 10 ng of purified DNA for every 100 bp of the amplicon was used in sequencing reactions using the oligonucleotides of SEQ ID NO.: 30 and DW-ACP-N. The MREJ sequences from MRSA strains CCRI-12524, CCRI-12535, CCRI-12810, and CCRI-12905 (described in Table 3) are designated SEQ ID NOs.: 39, 40, 41, and 42 (Table 8).

CCRI-12376 and CCRI-12593 described in Table 3 were not sequenced but rather characterized using PCR primers and shown to contain MREJ type xiii using specific amplification primers.

EXAMPLE 3

Sequence Analysis of Novel MREJ Types xi-x

The sequences obtained for 15 of the 17 strains non-amplifiable by the MRSA-specific primers detecting MREJ types i to x previously described were compared to the sequences available from public databases. In all cases except MRSA strain CCRI-12845, the orfX portion of the MREJ sequence had an identity close to 100% to publicly available sequences for orfX CCRI-12845 has a deletion in orfX (SEQ ID NO.: 21) (described below). While the orfX portion of most MREJ fragments (SEQ ID NOs.: 15-20, 25-26, 39-42, 55-56) shared nearly 100% identity with publicly available *S. aureus* orfX sequences, with the exception of strain CCRI-12845, the DNA sequence within the right extremity of SCCmec itself was shown to be different from those of MREJ types i, ii, iii, iv, v, vi, vii, viii, ix, and x. (International Patent Application PCT/CA02/00824, U.S. Pat. No. 6,156,507). The DNA sequence within the right extremity of SCCmec of CCRI-12845 was similar to that of MREJ type ii (see below). Thus, ten different novel MREJ sequence types are reported herein: MREJ types xi to xx.

The sequences within the right extremity of SCCmec obtained from strains CCRI-12157, CCRI-12198, and CCRI-12199 (SEQ ID NOs.: 17, 18, and 19) were nearly identical to each other, and different from those of MREJ types i, ii, iii, iv, v, vi, vii, viii, ix, and x (Ito et al., 2001, Antimicrob. Agents Chemother. 45:1323-1336; Ma et al., 2002, Antimicrob. Agents Chemother. 46:1147-1152, Huletsky et al., 2004, J. Clin. Microbiol. 42:1875-1884, International Patent Application PCT/CA02/00824, U.S. Pat. No. 6,156,507). These new sequences were designated as MREJ type xi (SEQ ID NOs.: 17-19). A BLAST™ search revealed that the first 79 bp of the SCCmec portion of MREJ type xi exhibited 87% identity with an unknown sequence of *Staphylococcus epidermidis* strain SRI (GenBank accession number AF270046). The remainder of the MREJ sequence was shown to be unique, exhibiting no significant homology to any published sequence.

The sequence obtained at the right extremity of SCCmec from strain CCRI-12719 (SEQ ID NO.: 20) was different from MREJ types i to x as well as from MREJ type xi. The new MREJ type was designated as MREJ type xii. When compared with GenBank sequences using BLAST™, the sequence at the right extremity of SCCmec of MREJ type xii exhibited 100% identity with the sequence found at the right extremity of the SCCmec type V recently described (Ito et al., 2004, Antimicrob. Agents. Chemother. 48:2637-2651, GenBank accession number AB 121219).

The sequences within the right extremity of SCCmec obtained from strains CCRI-11976, CCRI-12382, and CCRI-12383 (SEQ ID NOs.: 15, 25, and 26) were 100% identical to each other, different from MREJ types i to x as well as from MREJ types xi and xii. The new MREJ sequences were designated as MREJ type xiii (SEQ ID NOs.: 15, 25, and 26).

The sequence within the right extremity of SCCmec obtained from strain CCRI-11999 (SEQ ID NO.:16) was also different from MREJ types i to x as well as from MREJ types xi, xii, and xiii, and consequently, was designated as MREJ type xiv. A BLAST™ search of the MREJ types xiii and xiv sequences showed that a portion of the SCCmec of these two MREJ types was identical to that of MREJ type ix. Indeed, the SCCmec portions of MREJ types ix and xiv were preceded by one and two consecutive 102 bp insertions, respectively, when compared to MREJ type xiii. The rest of the MREJ types ix, xiii, and xiv sequences, which were 100% identical to each other, exhibited 100% identity with a region of the SCC cassette (which do not contain mecA) harbouring cassette chromosome recombinase genes of the methicillin-susceptible *S. epidermidis* ATCC 12228 genome (GenBank accession number BK001539). The sequence of the 102-pb insertion was 99-100% identical to that found in MREJ type ii.

The sequence obtained within the right extremity of SCCmec from strain CCRI-9887 was different from MREJ types i to x as well as from MREJ types xi to xiv and was therefore designated as MREJ type xv (SEQ ID NO.: 56). A BLAST™ search of the sequence obtained within the SCCmec portion (126 nucleotides) of MREJ type xv revealed that this DNA fragment exhibited 96% identity with a sequence of the SCC cassette (which do not contain mecA) of the methicillin-susceptible *S. aureus* strain M (GenBank accession number U10927). Although the sequence of MREJ type xv has been described, the localization of this sequence downstream of orfX in a MRSA strain has heretofore not been described.

The sequence obtained for MREJ from strain CCRI-12845 (SEQ ID NO.: 21) revealed that the MREJ fragment of this strain has a deletion of nucleotides 165 to 434 of orfX (269-bp fragment), whereas the sequence at the right extremity of SCCmec (328 nucleotides) had identities ranging from 99.8 to 100% with that of MREJ type ii available in public databases. Although the MREJ sequence obtained from this strain exhibited a high level of identity with known MREJ sequences, the presence of a 269-bp deletion within orfX had heretofore never been described. As one of the oligonulcoetides used in the initial PCR amplification assay described above falls within this 269 bp deletion, the deletion in orfX explains why this MRSA strain was not or could not have been detected with primers and probes previously described to detect MRSA (U.S. Pat. No. 6,156,507 and International Patent Application PCT/CA02/00824). The novel MREJ sequence of this strain was designated as MREJ type xvi.

The sequence obtained at the right extremity of SCCmec from strain CCRI-9772 was different from MREJ types i to x as well as from MREJ types xi to xvi. The new MREJ type was designated as MREJ type xvii (SEQ ID NO.:55). A BLAST™ search against the GenBank database revealed that the SCCmec portion of MREJ type xvii sequence exhibited 100% identity with the sequence at left of the SCCmec junction of *S. aureus* strain CA05 (JCSC 1968) (GenBank Accession number AB063172) harbouring SCCmec type IV (Ma et al., 2002. Antimicrob. Agents Chemother. 46:1147-1152). Although the sequence itself has been described previously, the localization of this sequence downstream of orfX in a MRSA strain has heretofore never been described.

The sequences obtained from the right extremity of SCCmec from strains CCRI-12524 and CCRI-12535 were nearly identical to each other but were different from MREJ types i to x as well as from MREJ types xi to xvii and were therefore designated as MREJ type xviii (SEQ ID NOs.:39 and 40). A BLAST™ search against GenBank sequences revealed that the first 40 bp of the SCCmec portion of MREJ type xviii exhibited 92% identity with a sequence of the genome of *S. epidermidis* strain SRI with unknown function (GenBank accession number AF270130). The remainder of the sequence was shown to be unique, exhibiting no significant homology to any published sequence.

The sequence obtained from strain CCRI-12810 was different from MREJ types i to x as well as from MREJ types xi to xviii and was designated as MREJ type xix (SEQ ID NO.:41). When compared with GenBank sequences using BLAST, the SCCmec portion of MREJ type xix sequence exhibited 100% identity with a sequence of unknown function of the genome of strain MRSA 252 located at the left of SCCmec (GenBank accession number BX571856). Although the sequence itself had been described, the presence of this DNA fragment downstream of orfX had heretofore never been described.

The sequence obtained at the right extremity of SCCmec from strain CCRI-12905 was different from MREJ types i to x as well as from MREJ types xi to xix and was designated as MREJ type xx (SEQ ID NO.:42). When compared with Genbank sequences using BLAST, the SCCmec portion (328 bp) of MREJ type xx sequence exhibited 100% identity with the sequence downstream of orfX of the methicillin-susceptible *S. aureus* strain NCTC 8325 (GenBank accession number AB014440. The localization of this sequence downstream of orfX in a MRSA strain has heretofore never been described.

EXAMPLE 4

Sequence Comparison of New MREJ Types xi to xx

Figure 3:
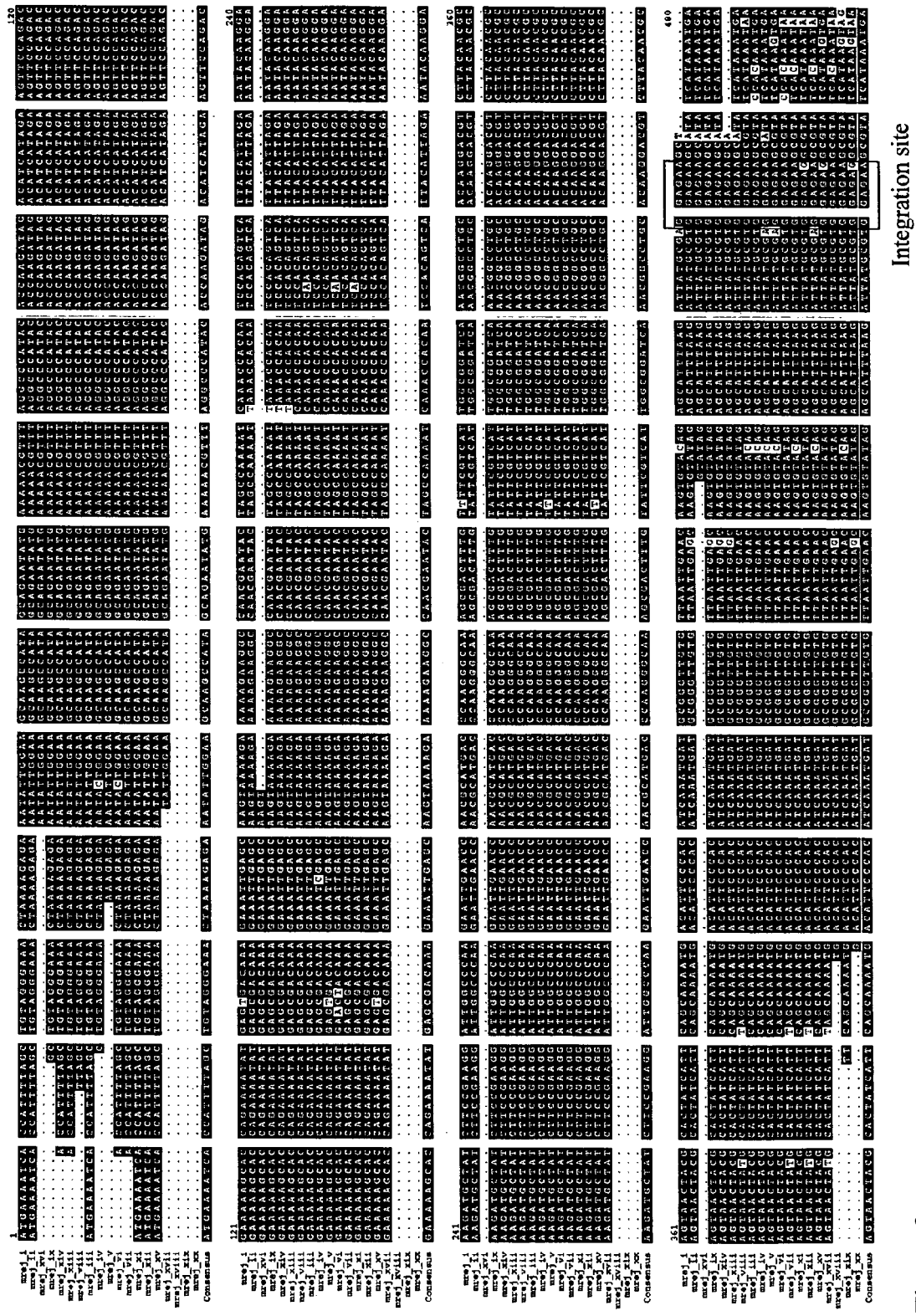
FIG. 3 illustrates a multiple sequence alignment of 19 representative MREJ types i to ix and xi to xx comprising the orfX, the integration site, and the first 535 nucleotides of the SSCmec right extremity. MREJ types i to ix sequences correspond to SEQ ID NOs.: 77, 78, 79, 80, 81, 82, 83, 84 and 85, respectively. SEQ ID NO.: 18 corresponds to MREJ type xi, SEQ ID NO:20 corresponds to MREJ type xii, SEQ ID NO:15 corresponds to MREJ type xiii, SEQ ID NO:16 corresponds to MREJ type xiv, SEQ ID NO:56 corresponds to MREJ type xv, SEQ ID NO:21 corresponds to MREJ type xvi, SEQ ID NO:55 corresponds to MREJ type xvii, SEQ ID NO:39 corresponds to MREJ type xviii, SEQ ID NO:41 corresponds to MREJ type, and SEQ ID NO:42 corresponds to MREJ type xx.
Figure 3:
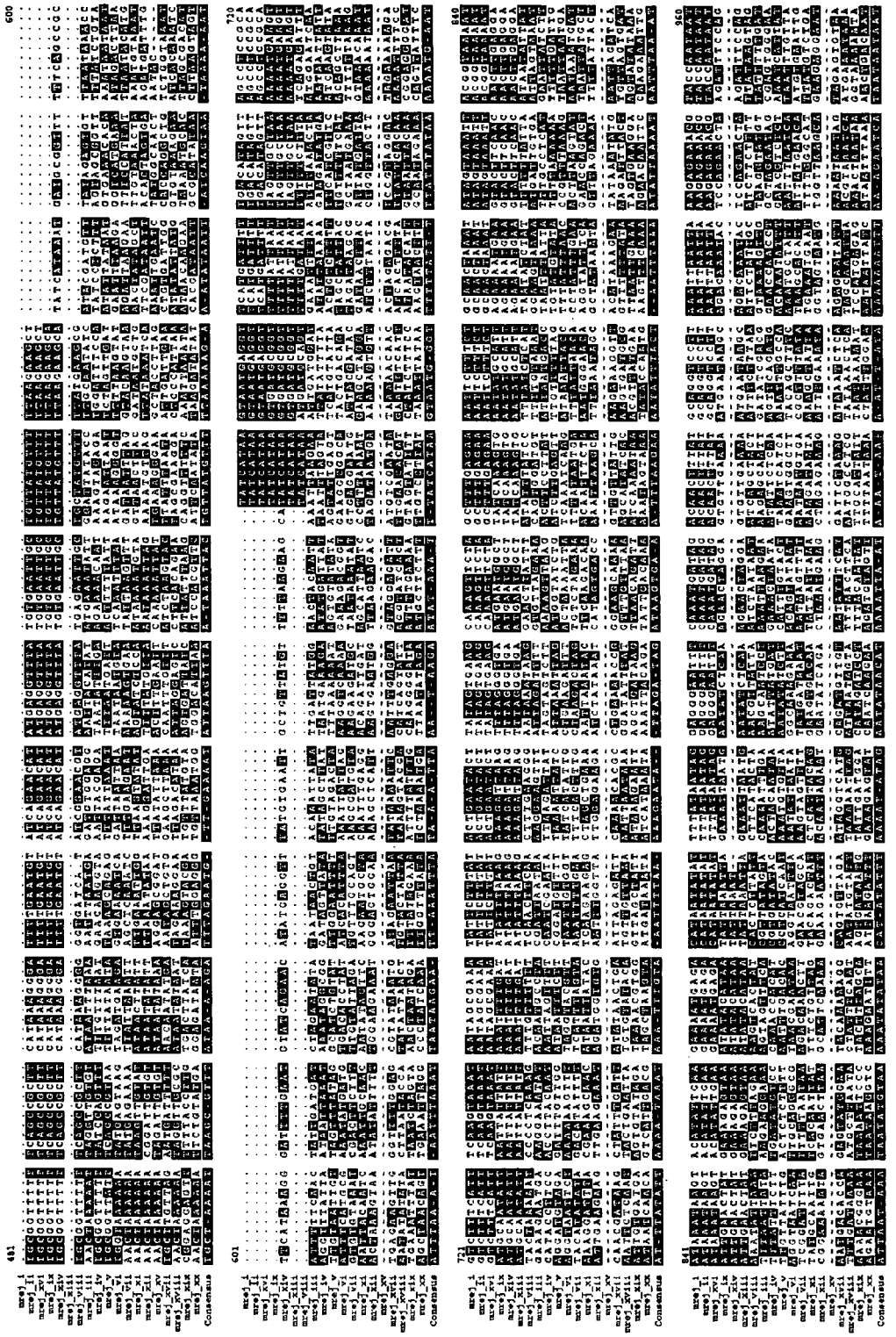
Figure 3A:
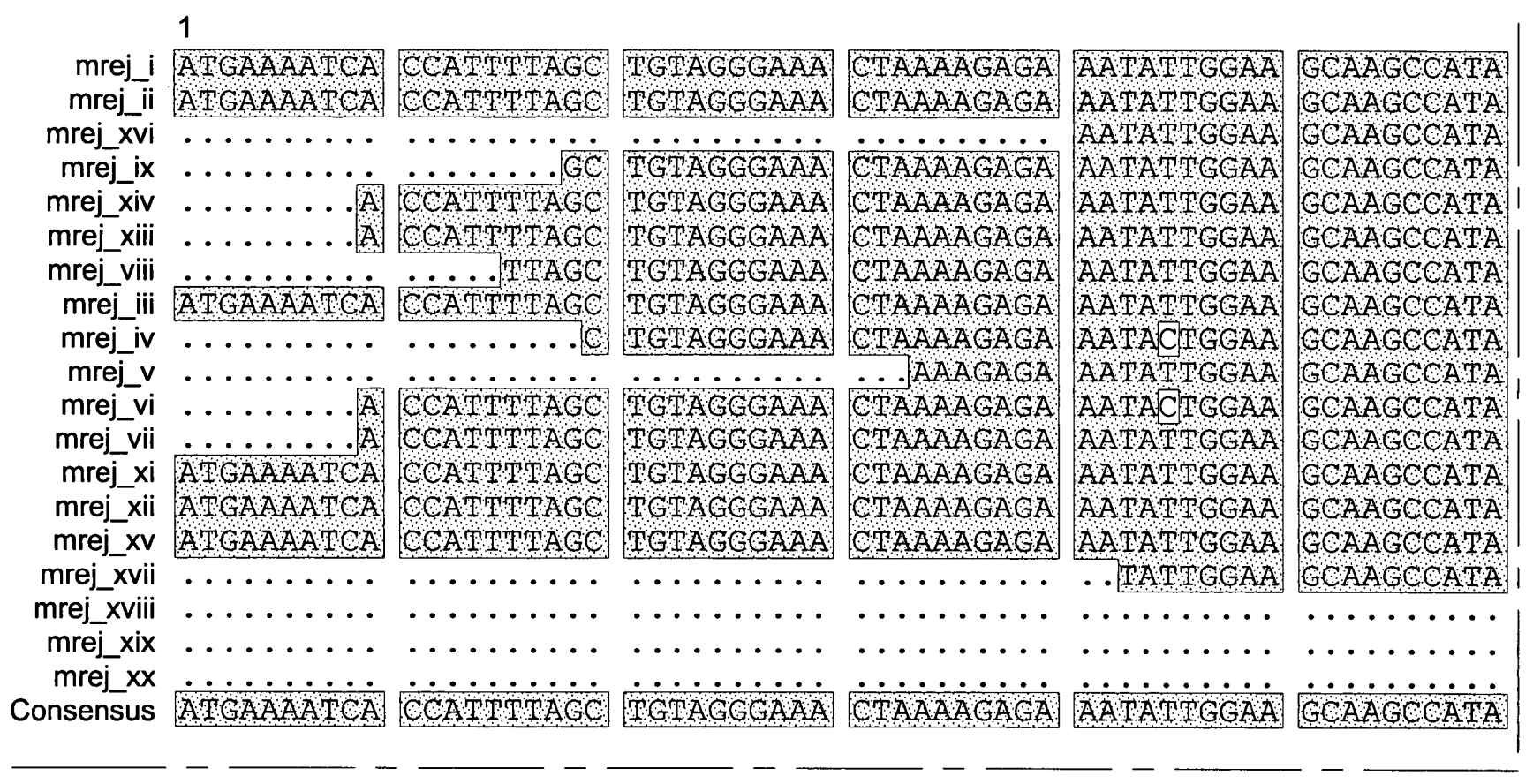
Figure 3B:
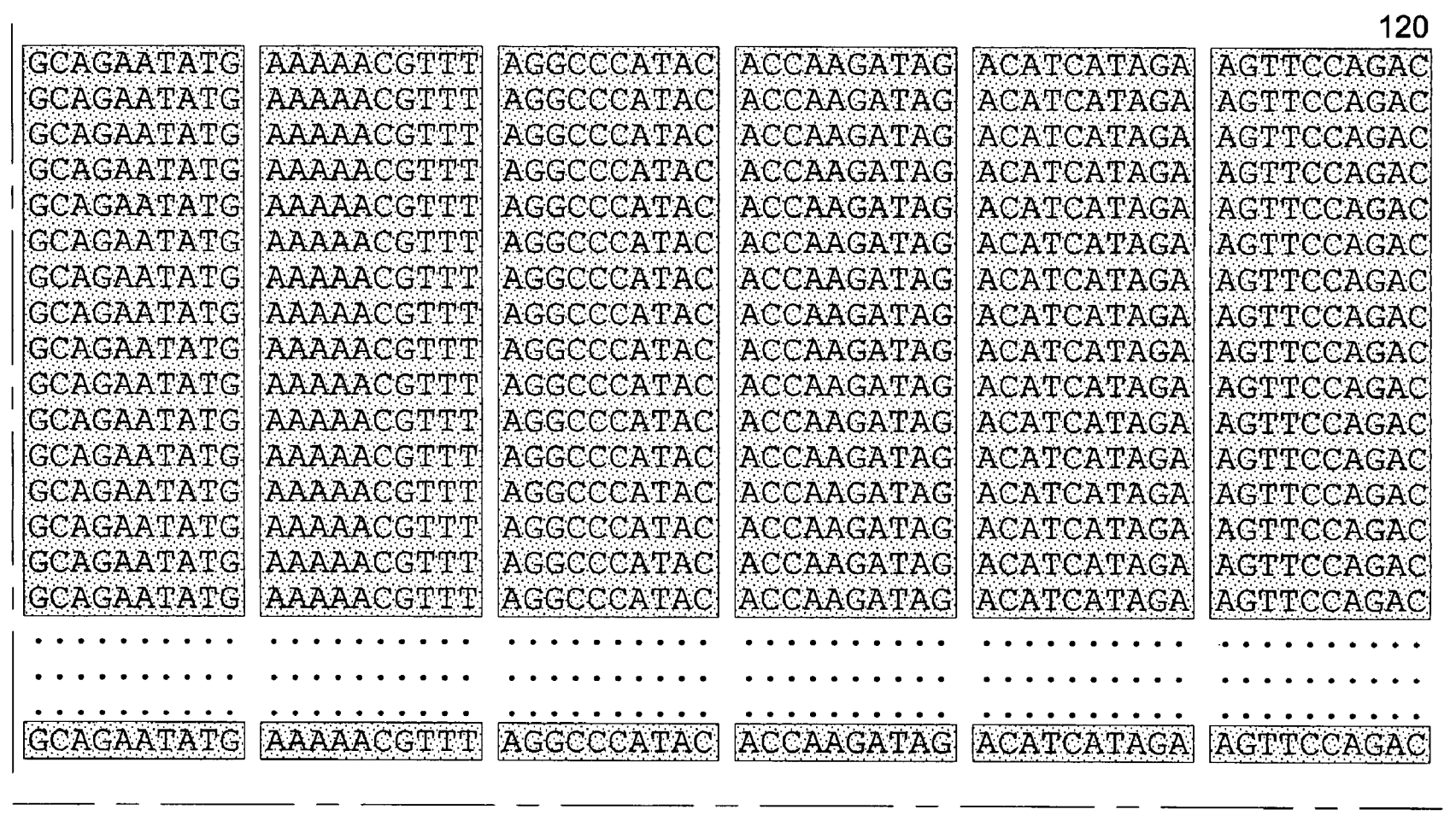
Figure 3C:
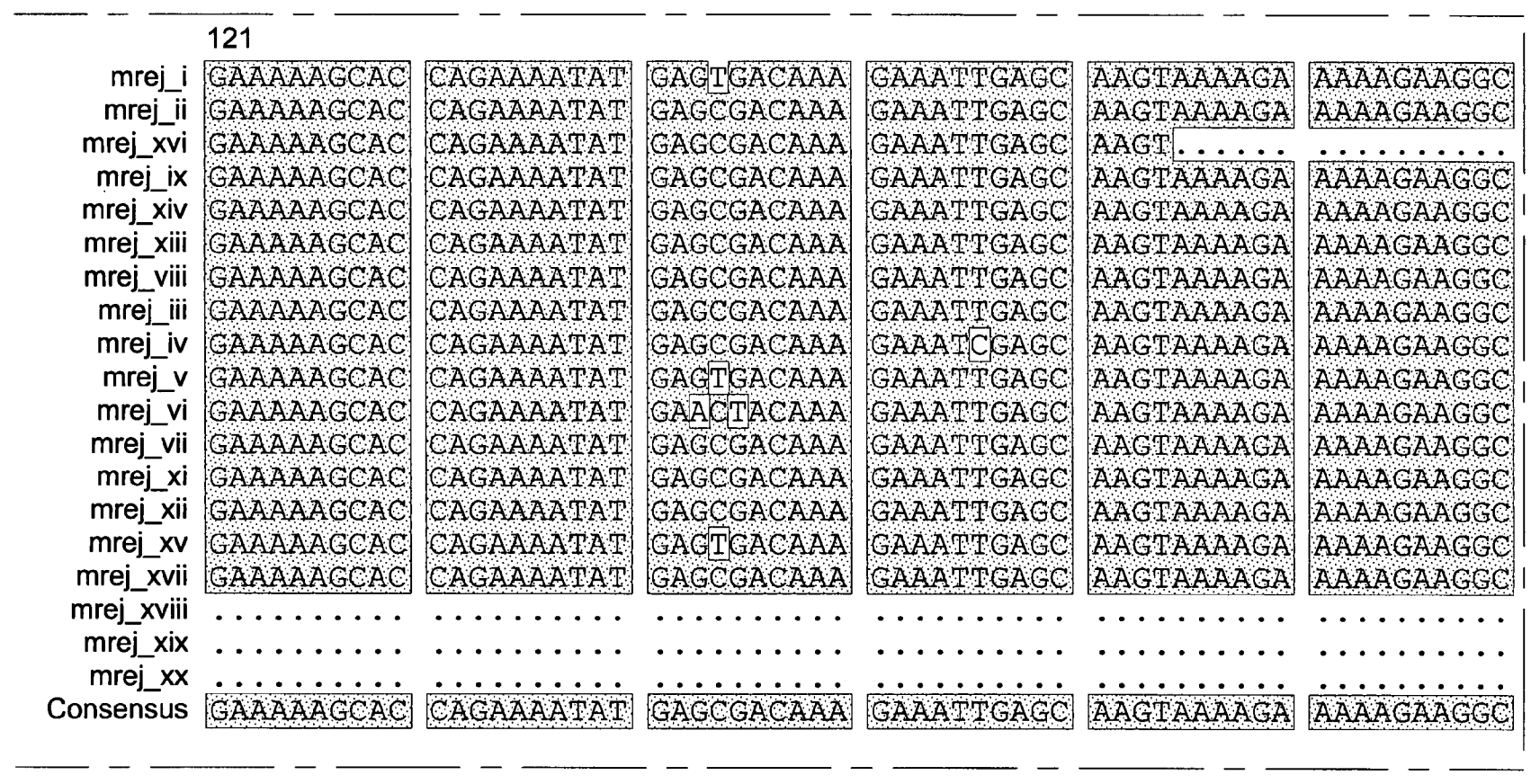
Figure 3E:
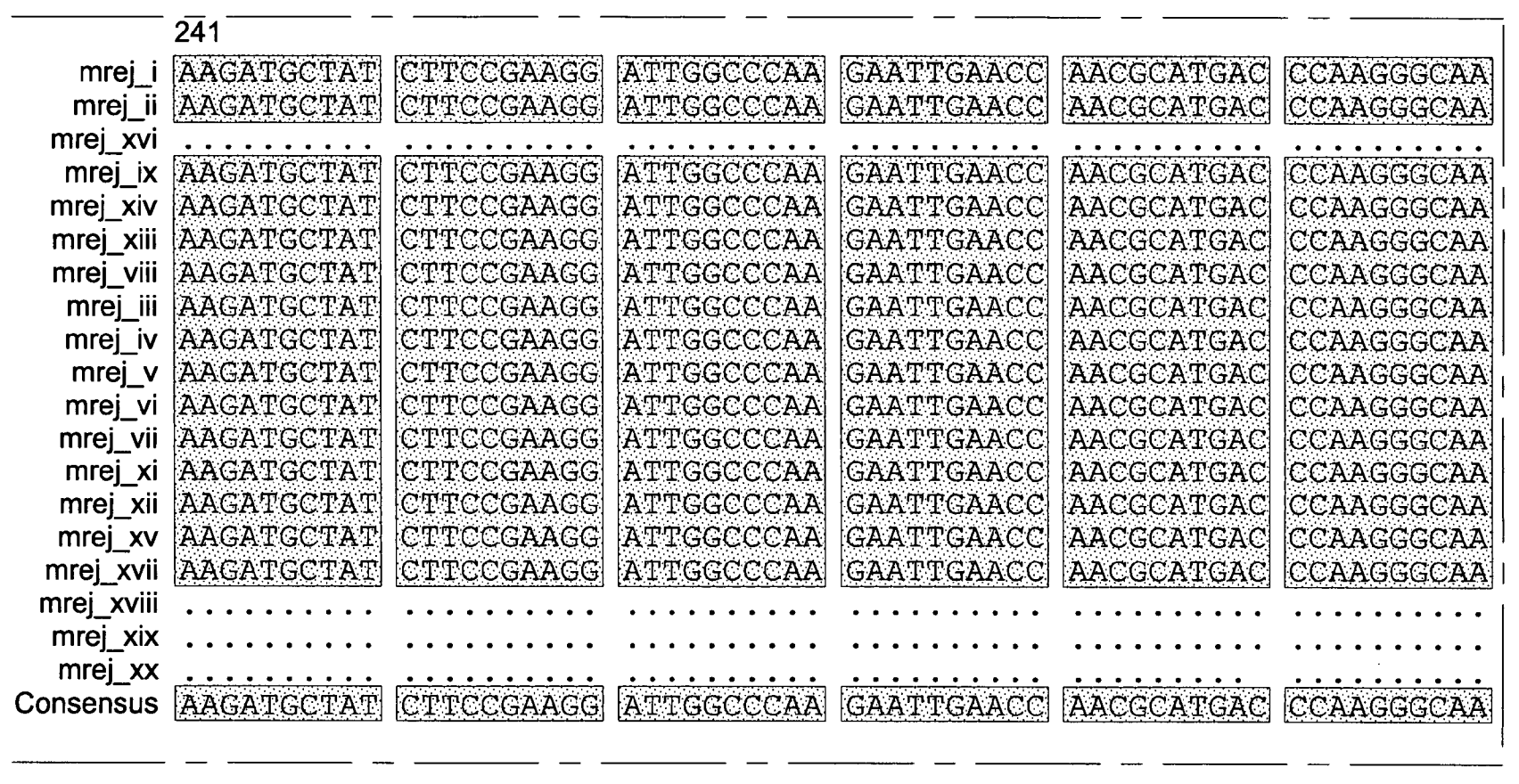
Figure 3F:
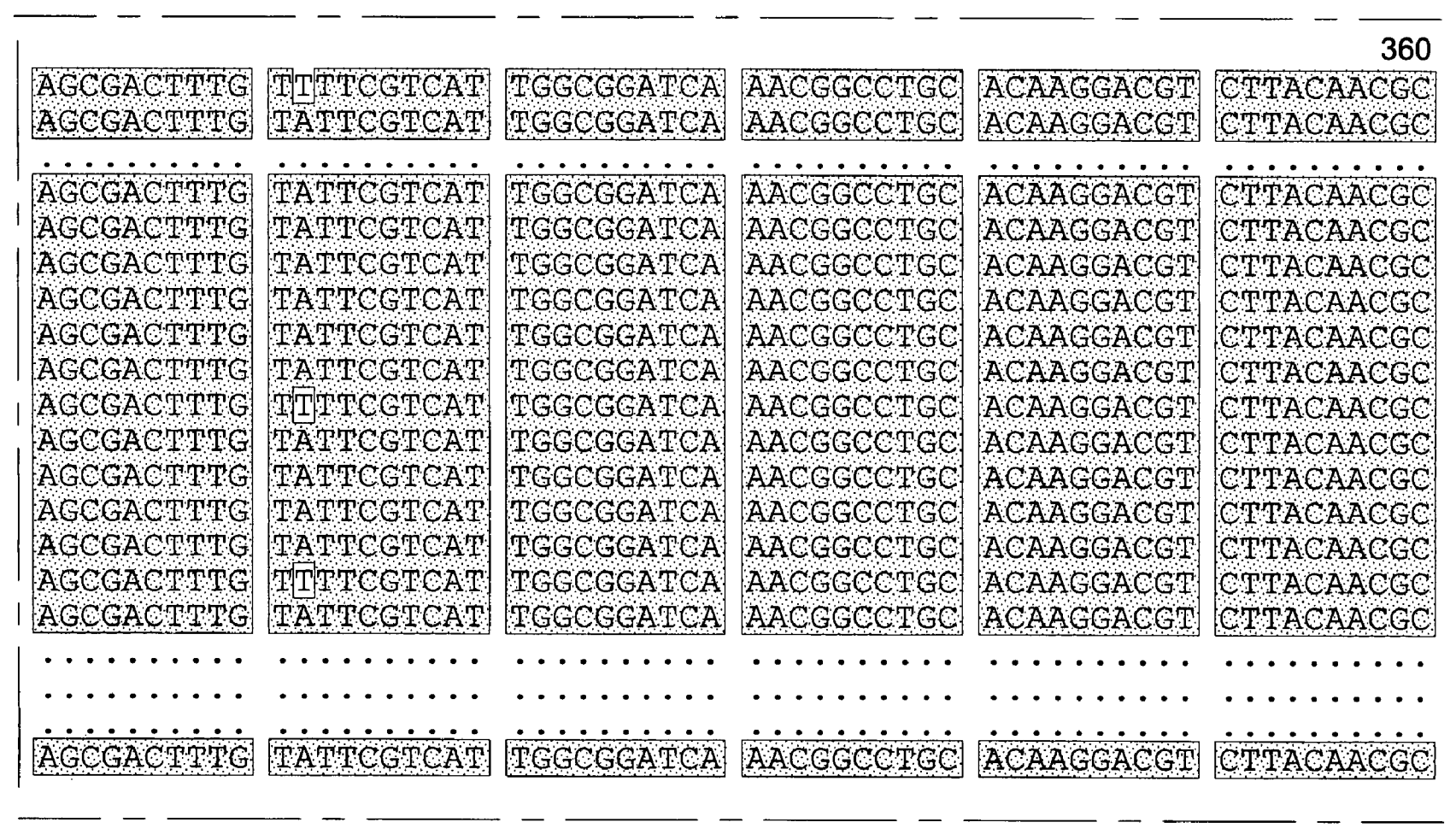
Figure 3H:
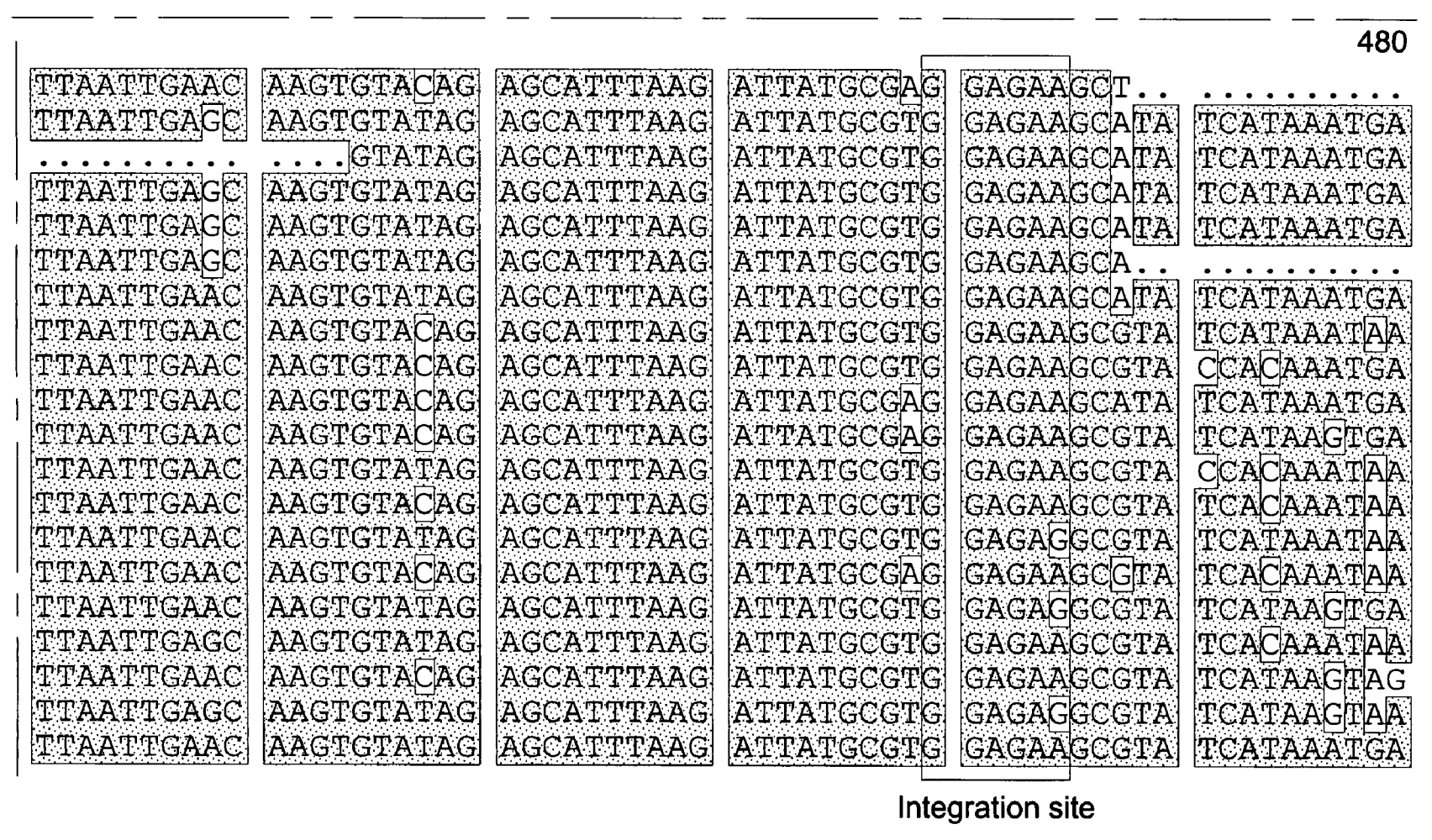
Figure 3I:
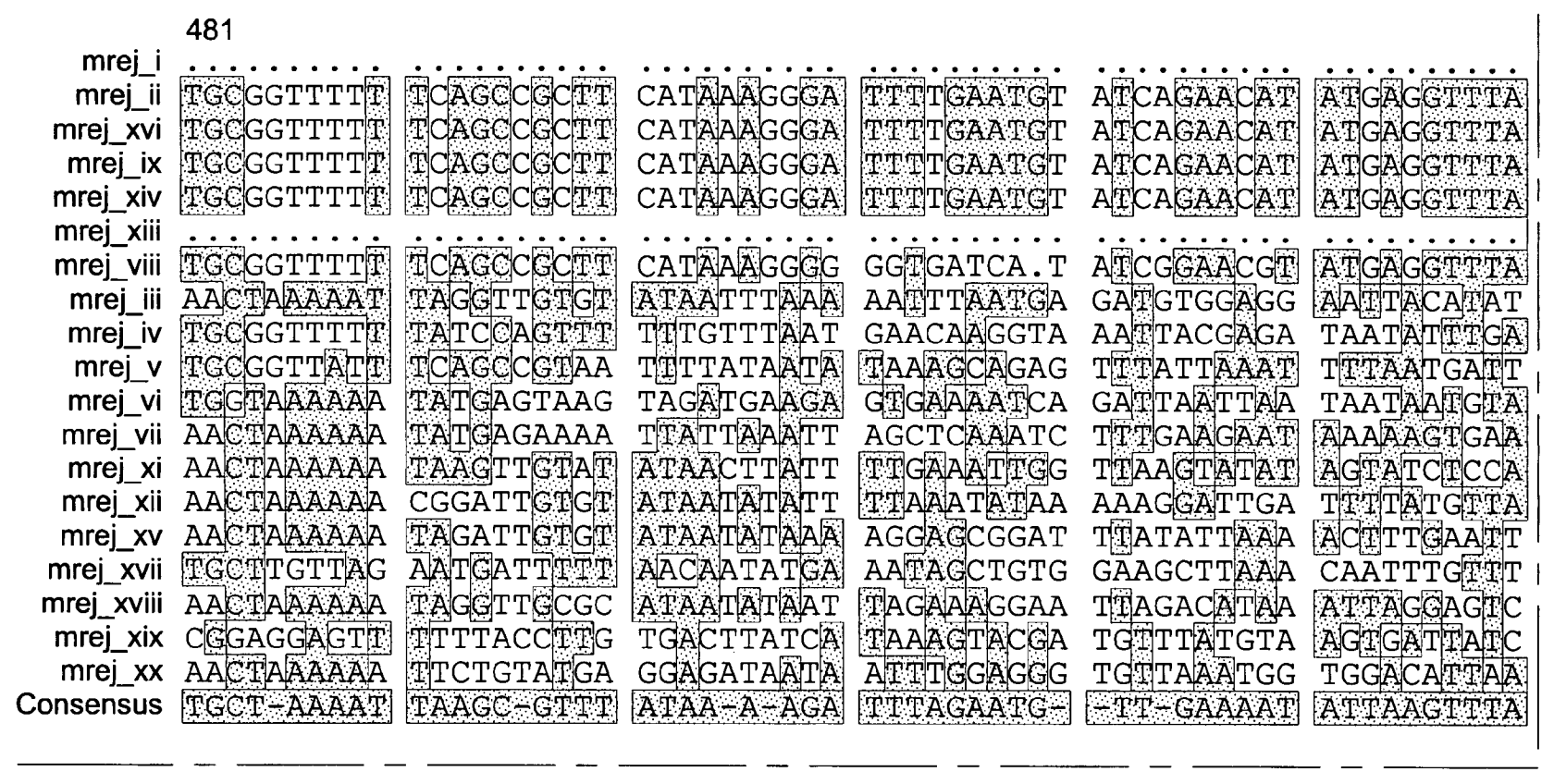
Figure 3J:
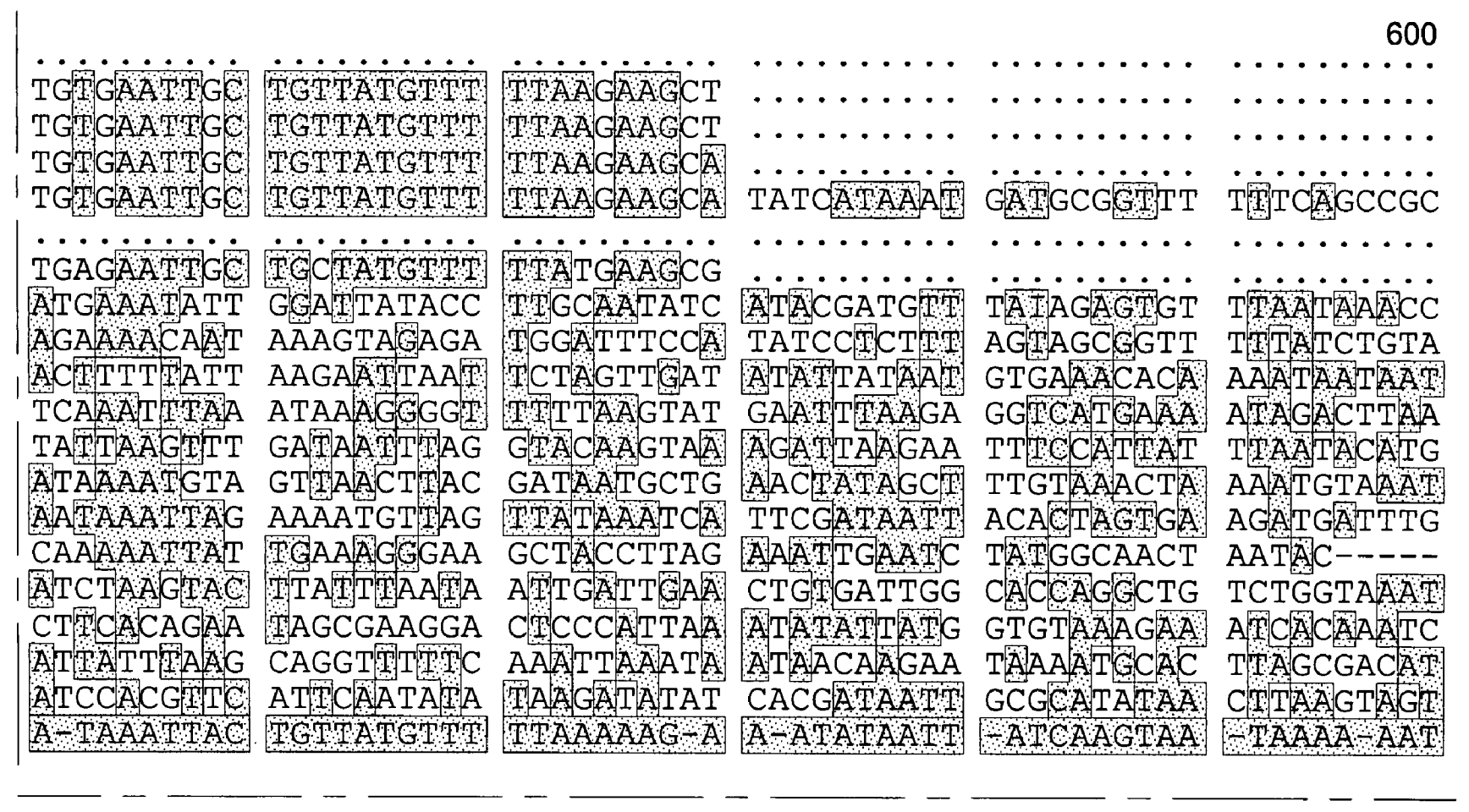
Figure 3K:
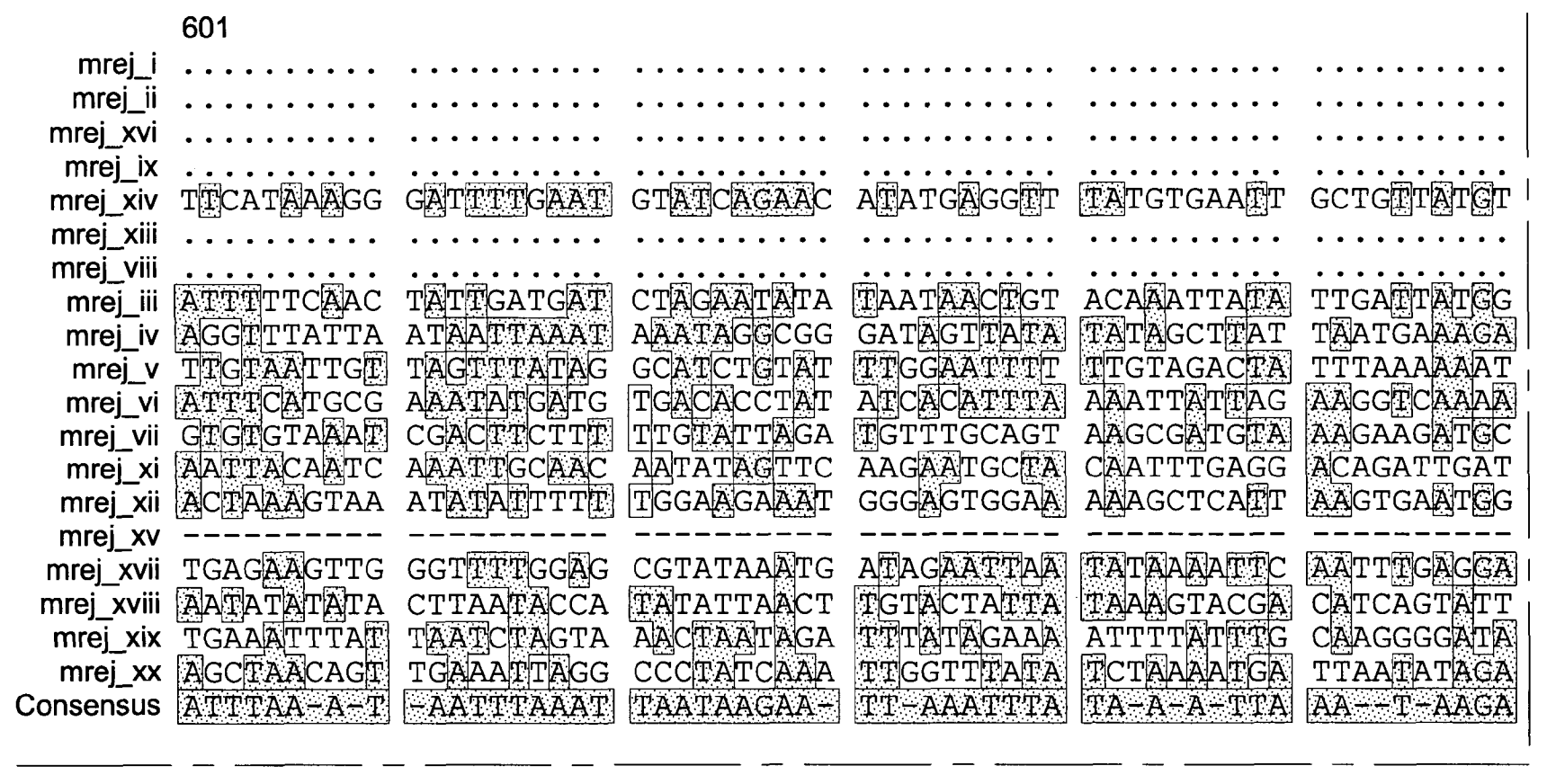
Figure 3L:
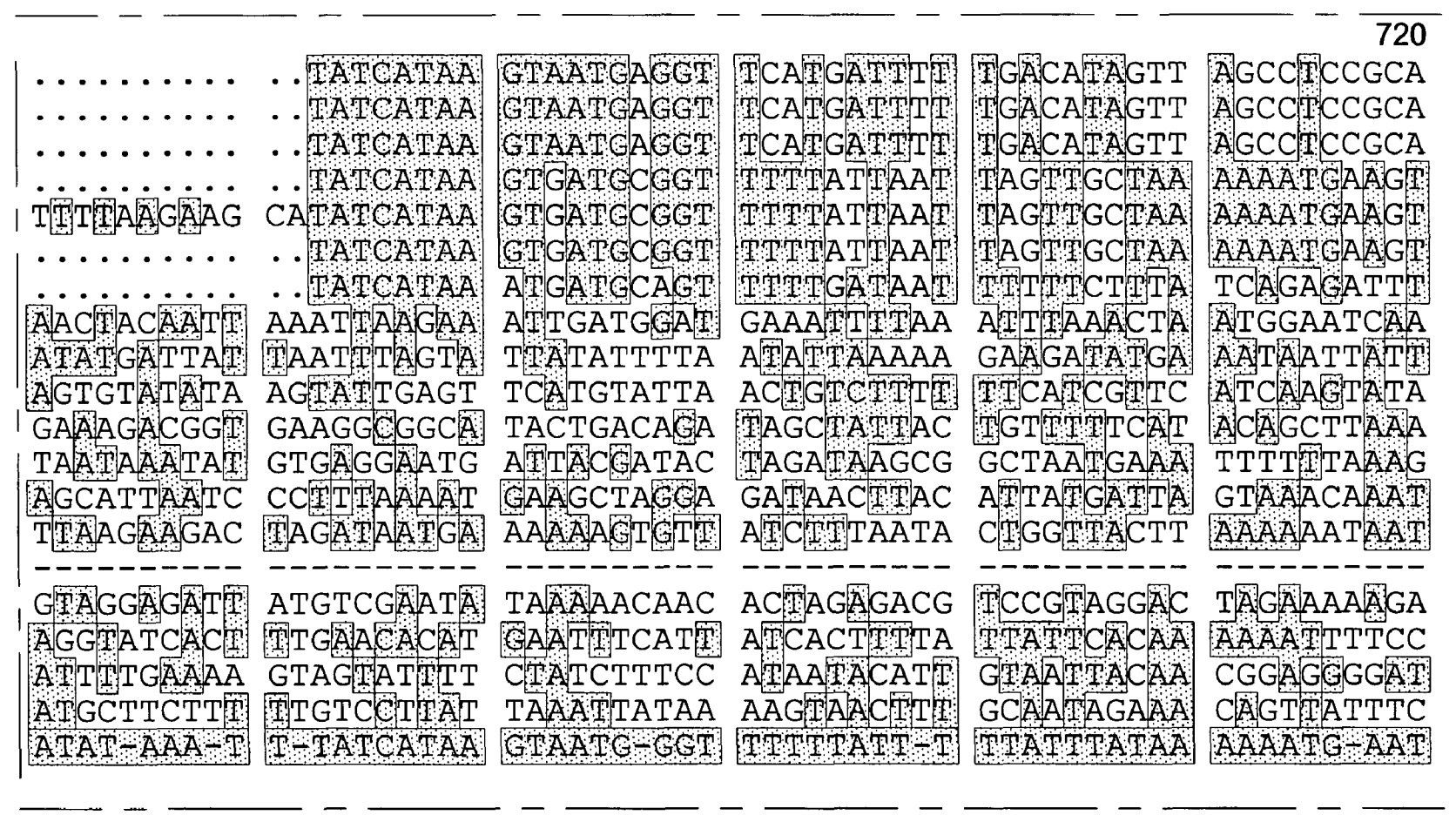
Figure 3M:
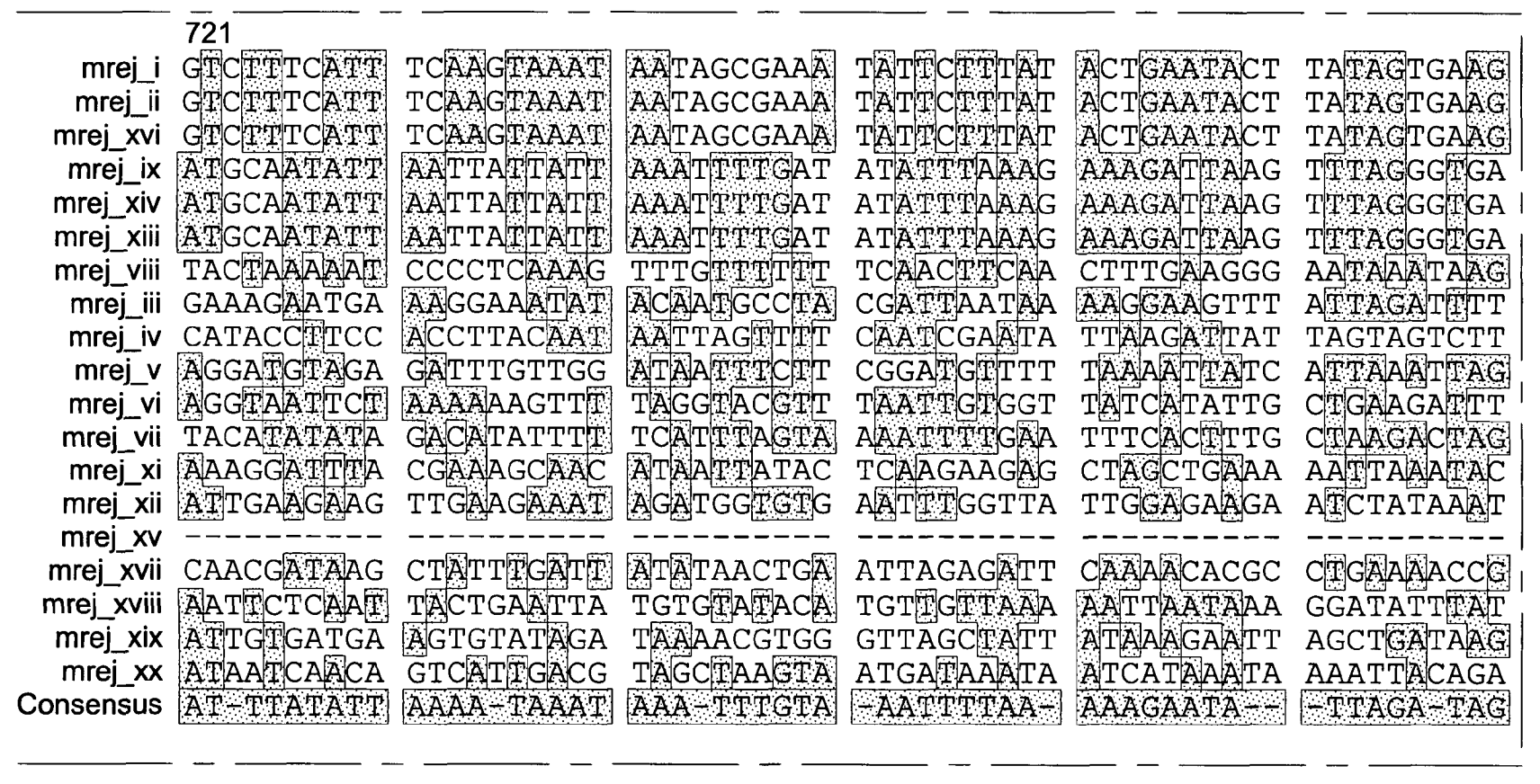
Figure 3N:
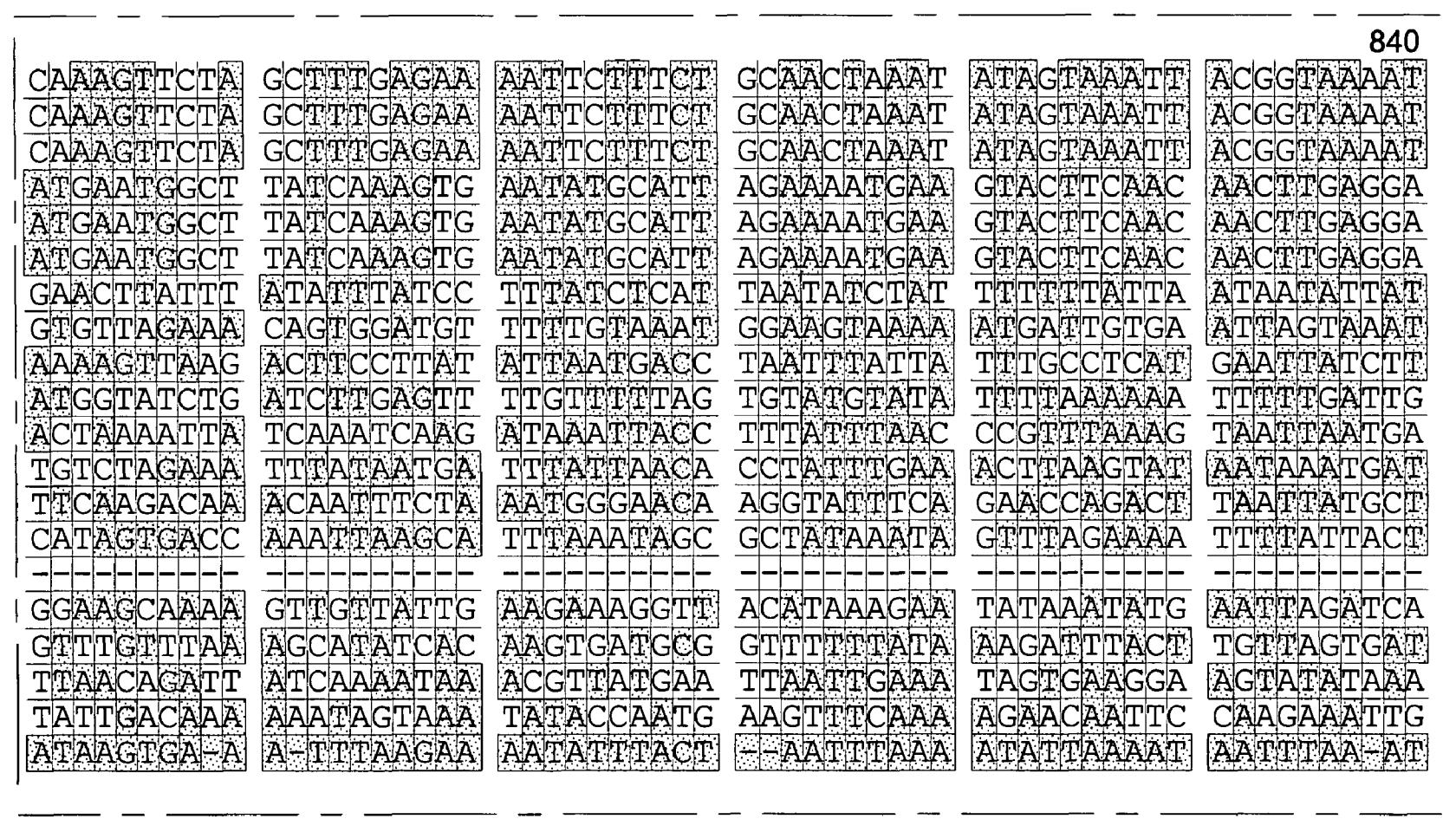
Figure 3O:
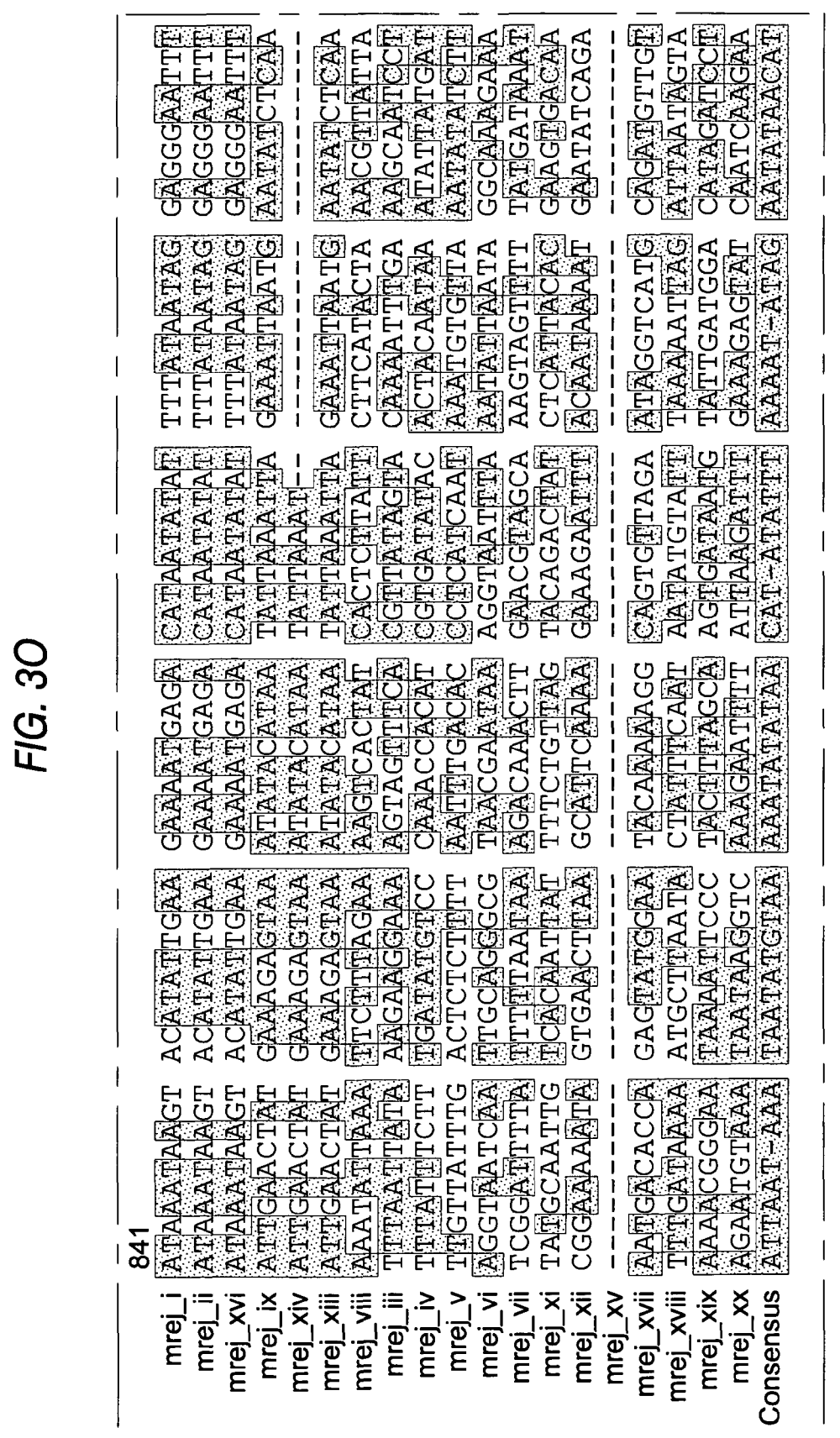
Figure 3P:
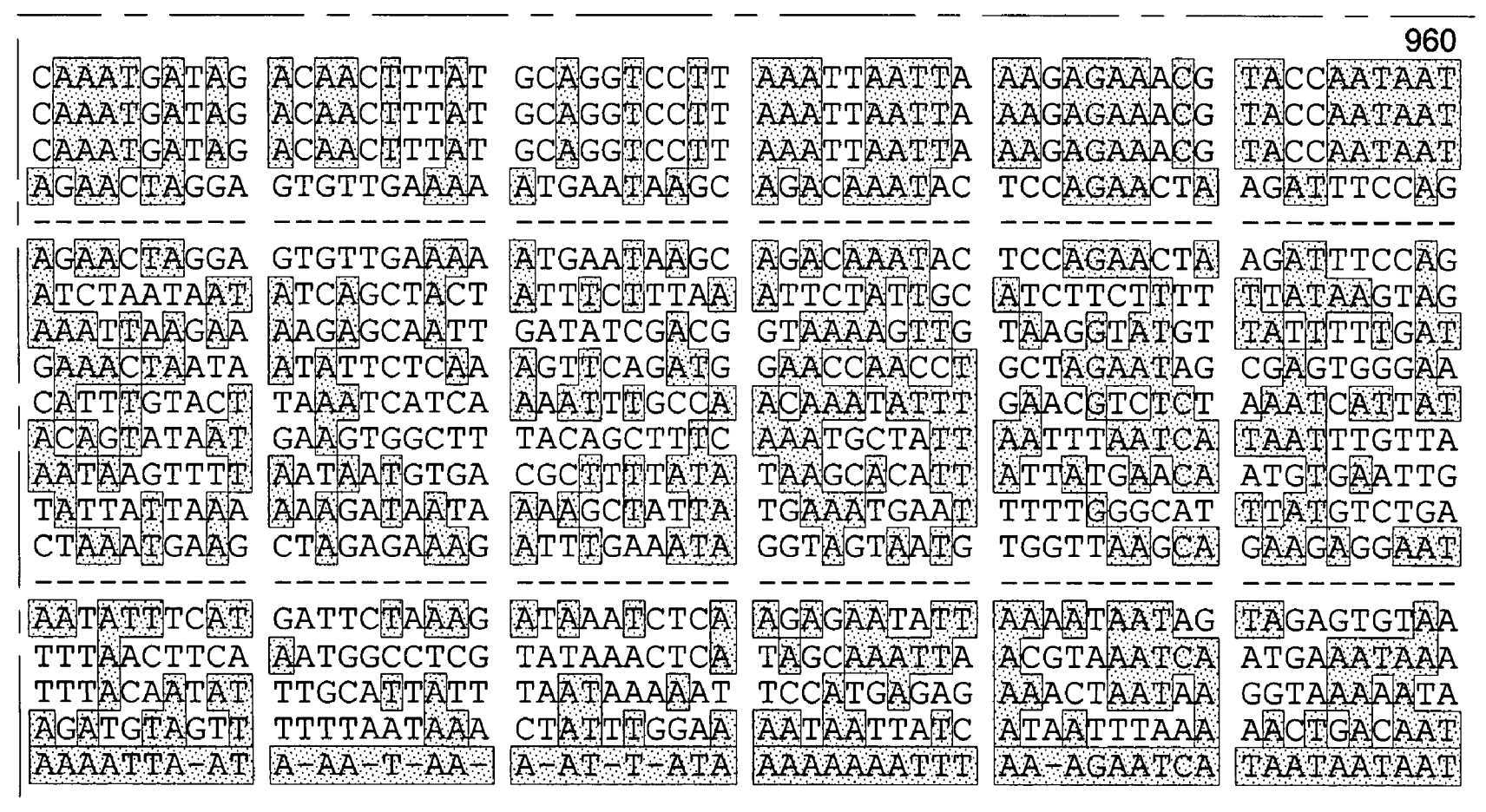
Figure 3Q:
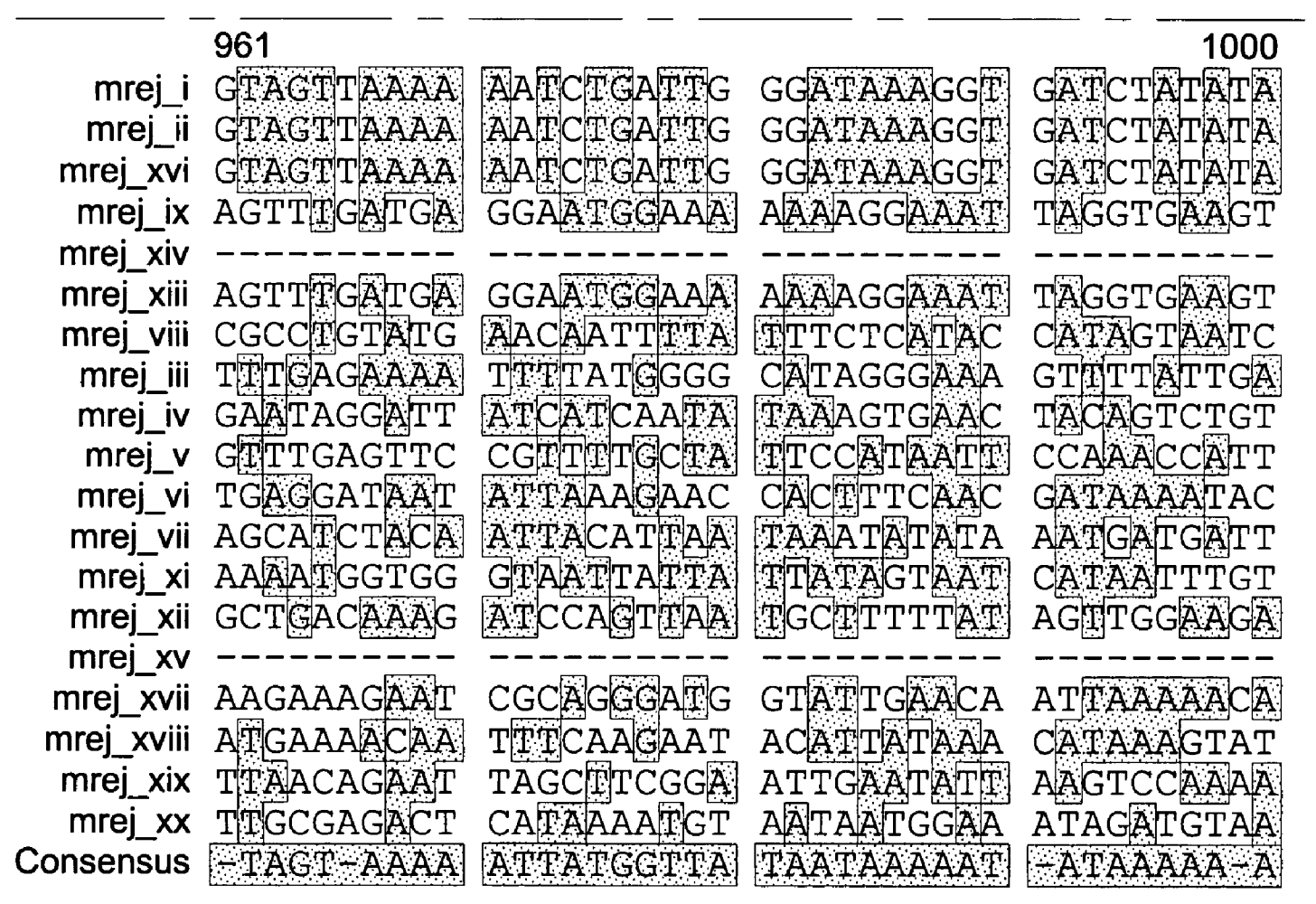

The sequences of the first 500-nucleotide portion of the SCCmec right extremity of all new MREJ types (xi to xx) were compared with each other and with those of the previously described MREJ types i to ix using GCG software programs Pileup and Gap (GCG, Wisconsin). Table 12 depicts the identities at the nucleotide level between the SCCmec right extremities of the 10 novel MREJ types (xi to xx) with those of the MREJ types previously described (i to ix) using the GCG program Gap. MREJ type x was excluded from this comparison since this MREJ sequence is deleted of the complete orfX and of the SCCmec integration site as well as ~4 kb at the right extremity of SCCmec when compared to the right extremity of SCCmec type II. The SCCmec right extremity of MREJ types ix, xiii, and xiv differed by only one and two 102-bp insertions present in MREJ types ix and xiv, respectively. However, the rest of these three sequences showed nearly 100% identity (FIG. 3). Although the SCCmec portion of MREJ type xvi is nearly 100% identical with that of MREJ type ii, the deletion of nucleotides 165 to 434 of orfX in MREJ type xvi has never been described previously. The SCCmec right extremities of all other new MREJ types showed identities ranging from 38.2 to 59.5% with each other or with MREJ types i to ix. The substantial variation between the novel MREJ sequences and the previously described sequences, from which the prior detection assays were based, explains why the right extremities of the novel MREJ types xi to xx disclosed in the present invention could not have been predicted nor detected with MREJ primers previously described (U.S. Pat. No. 6,156,507, International Patent Application PCT/CA02/00824, Ito et al., 2001, Antimicrob. Agents Chemother. 45:1323-1336, Huletsky et al., 2004, J Clin. Microbiol. 42:1875-1884, Ma et al, 2002, Antimicrob. Agents Chemother. 46:1147-1152, Ito et al, Antimicrob Agents Chemother. 2004. 48:2637-2651, Oliveira et al, 2001, Microb. Drug Resist. 7:349-360).

EXAMPLE 5

Figure 2:
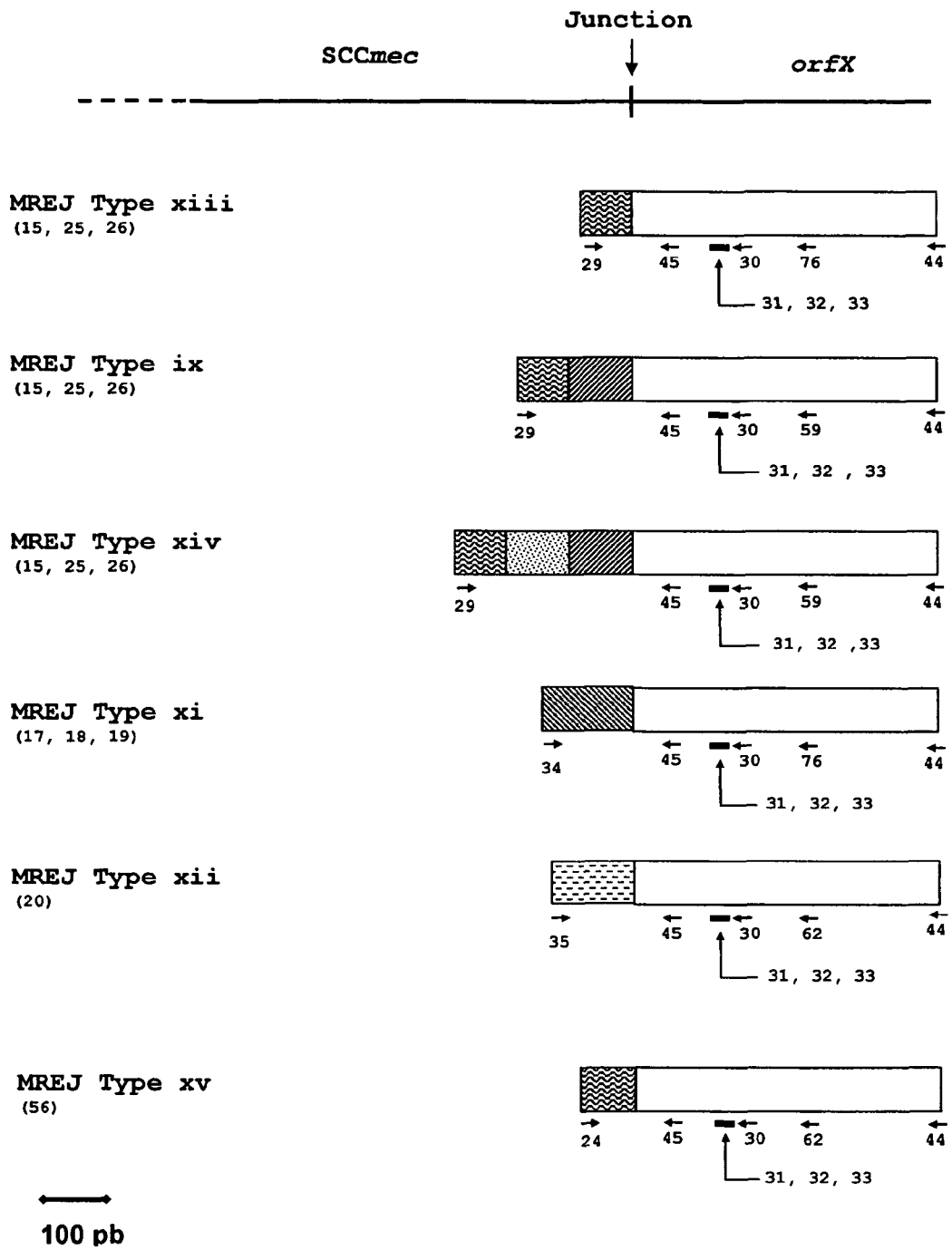
FIG. 2 depicts the SCCmec right extremity junction and the position of the primers (SEQ ID NOs.: 4, 7-9, 24, 29-36, 44, 45, 59, 62, 73) developed in the present invention for detection and identification of novel MREJ types xi, xii, xiii, xiv, xv, xvi, xvii, xviii, xix, and xx. Amplicon sizes are listed in Table 11. Numbers in parenthesis under MREJ types indicate MREJ SEQ ID NOs. Arrows indicate the positions of primers and the numbers below indicate their respective SEQ ID NOs. Dark bars and numbers below indicate the positions of probes and their respective SEQ ID NOs. Deletion in MREJ type xvi indicates the position of the 269-bp deletion in orfX.
Figure 2:
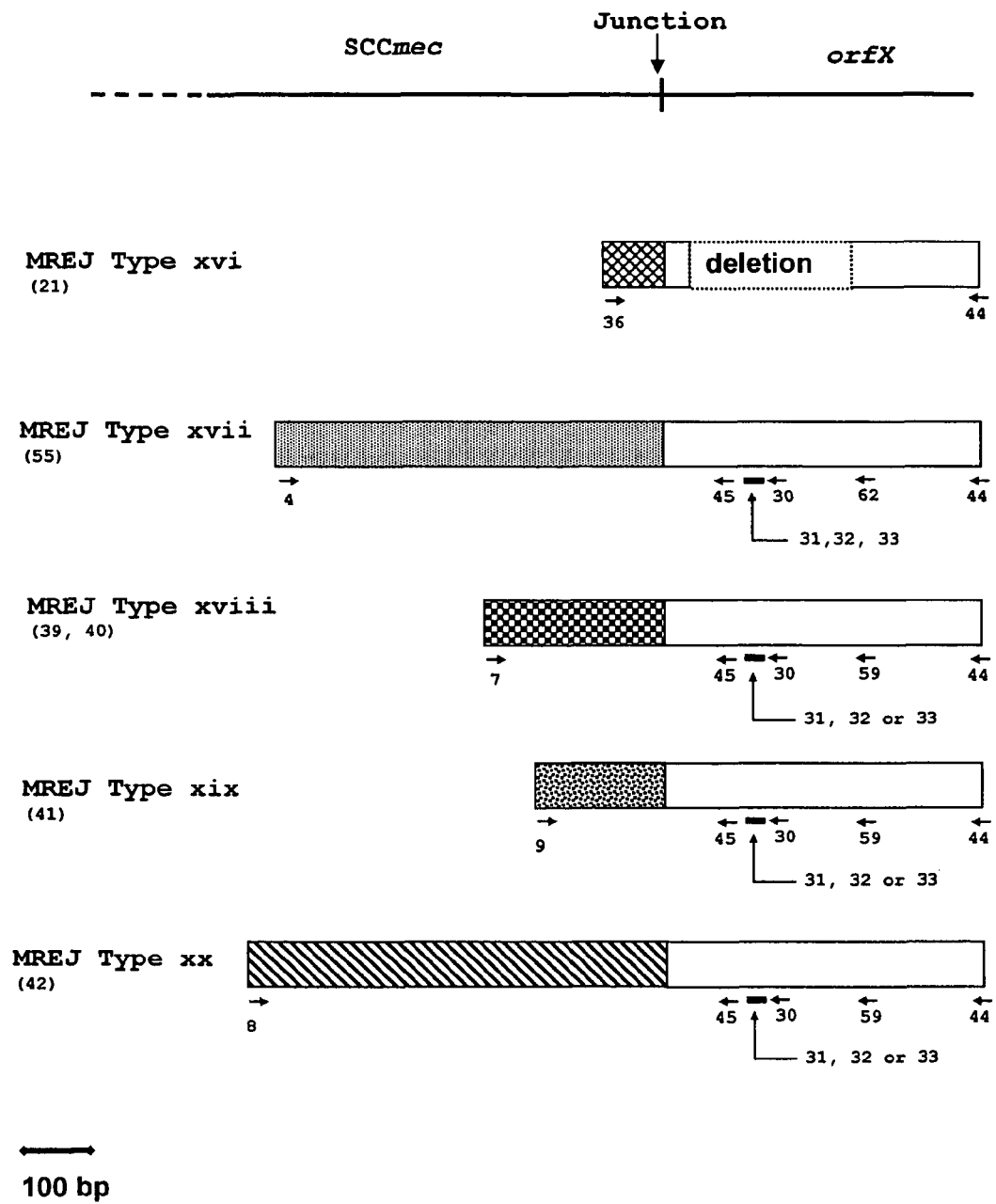

Selection of Amplification Primers from SCCmec/orfX Sequences of MRSA with MREJ types xi to xx Upon analysis of the 10 new MREJ types xi to xx sequence data described above, primers specific to each new MREJ type sequence were designed (FIG. 2, Tables 9 and 11). Primers specific to MREJ type xi (SEQ ID NO.: 34), MREJ type xii (SEQ ID NO.: 35), MREJ types xiii and xiv (SEQ ID NO.: 29) (also detect MREJ type ix but each of MREJ types ix, xiii, and xiv has a different amplicon length), MREJ type xv (SEQ ID NO.: 24), MREJ type xvii (SEQ ID NO.: 4), MREJ type xviii (SEQ ID NO.: 7), MREJ type xix (SEQ ID NO.: 9), MREJ type xx (SEQ ID NO.: 8), were each used in combination with a primer specific to the S. aureus orfX (SEQ ID NO.: 30) and tested against their specific MREJ target. For the detection of MREJ type xvi, a primer targeting MREJ types i, ii, and xvi (Table 10) was used in combination with a primer targeting the S. aureus orfX (SEQ ID NO.: 44). MREJ types i, ii, and xvi can be distinguished from each other by their different amplicon length.

Oligonucleotides primers found to amplify specifically DNA from the target MRSA MREJ types were subsequently tested for their ubiquity by PCR amplification (i.e. ubiquitous primers amplified efficiently most or all isolates of MRSA of the target MREJ type). The specificity and ubiquity of the PCR assays were tested either directly with bacterial cultures or with purified bacterial genomic DNA. The specificity of the primers targeting MREJ types xi to xx was also verified by testing DNA from MRSA strains harboring all other MREJ types.

1 μl of a treated standardized bacterial suspension or of a genomic DNA preparation purified from bacteria were amplified in a 20 μl PCR reaction mixture. Each PCR reaction contained 50 mM KCl, 10 mM Tris-HCl (pH 9.0), 0.1% Triton X-100, 2.5 mM $MgCl_2$, 0.4 μM of each of MREJ type xi primer (SEQ ID NO.: 34), MREJ type xii primer (SEQ ID NO.: 35), MREJ types xiii and xiv primer (SEQ ID NO.: 29), MREJ type xv primer (SEQ ID NO.: 24), MREJ type xvi (SEQ ID NO.: 36), MREJ type xvii primer (SEQ ID NO.: 4), MREJ type xviii primer (SEQ ID NO.: 7), MREJ type xix primer (SEQ ID NO.: 9), or MREJ type xx primer (SEQ ID NO.: 8) which were each used in combination with 0.4 μM of a S. aureus-specific primer (SEQ ID NO.: 30 or SEQ ID NO.: 44 for MREJ type xvi), 200 μM of each of the four dNTPs (Pharmacia Biotech, Piscataway, N.J.), 3.3 μg/μl of BSA (SIGMA, St. Louis, Mos.), and 0.5 U Taq polymerase (Promega, Madison, Wis.) coupled with TaqStart™ Antibody (BD Biosciences, San Jose, Calif.).

PCR reactions were then subjected to thermal cycling: 3 min at 94° C. followed by 40 cycles of 60 seconds at 95° C. for the denaturation step, 60 seconds at 55° C. for the annealing step, and 60 seconds at 72° C. for the extension step, then followed by a terminal extension of 7 minutes at 72° C. using a standard thermocycler (PTC-200 from MJ Research Inc., Watertown, Mass.). Detection of the PCR products was made by electrophoresis in agarose gels (1.2%) containing 0.25 μg/ml of ethidium bromide.

Each of the MRSA strains harbouring a specific MREJ target was specifically detected with their specific MREJ primers and there was no cross-detection with non targeted MREJ types.

This invention has been described herein above, and it is readily apparent that modifications can be made thereto without departing from the spirit of this invention. These modifications are under the scope of this invention, as defined in the appended claims.

TABLE 1

Reference *Staphylococcus aureus* strains used in the present invention[a]

| Strain number | Strain number | Strain number |
|---|---|---|
| Public collections (Type designation) | | |
| ATCC 6538[b] | BM10827 (C) | 54511 (Turku I E6) |
| ATCC 13301[b] | 3717 (EMRSA-GR1b) | 54518 (Turku II E7) |
| ATCC 23235[b] | 97S97 (Belgian epidemic clone 1a) | 61974 (Helsinki I E1) |
| ATCC 25923[b] | 359/96 (Berlin epidemic EMRSA IVc) | 62176 (Kotka E10) |
| ATCC 27660[b] | 792/96 (Berlin epidemic EMRSA IVd) | 62305 (mecA-Tampere I E12) |
| ATCC 29737[b] | 844/96 (Berlin epidemic EMRSA IVb) | 62396 (Helsinki II E2) |
| ATCC 29213[b] | 1966/97 (Hannover area EMRSA IIIc) | 75541 (Tampere II E13) |
| ATCC 29247[b] | 2594-2/97 (S. German EMRSA IIb) | 75916 (Helsinki V E5) |
| ATCC 33591 | 131/98 (S. German EMRSA II d2) | 76167 (Kemi E17) |
| ATCC 33592 | 406/98 (N. German EMRSA I c1) | 98442 (Helsinki VI E19) |
| ATCC 33593 | 408/98 (N. German EMRSA I c2) | 98514 (Helsinki VII E20) |
| ATCC 43300 | 872/98 (Hannover area EMRSA IIIb) | 98541 (Lohja E24) |
| ATCC BAA-38 (Archaic)[c] | 1155-1/98 (S. German EMRSA II c) | M307 (EMRSA-3) |
| ATCC BAA-39 (Hungarian)[c] | 1163/98 (S. German EMRSA II d1) | 90/10685 (EMRSA-15) |
| ATCC BAA-40 (Portuguese)[c] | 1869/98 (N. German EMRSA I d) | 98/14719 (EMRSA-15/b4) |
| ATCC BAA-41 (New York)[c] | HS 2 (I) | 96/32010 (EMRSA-16) |
| ATCC BAA-42 (Pediatric)[c] | AO 17934/97 (II) | 99/579 (EMRSA-16/a3) |
| ATCC BAA-43 (Brazilian)[c] | 98/10618 (EMRSA-15/b2) | 5 (E1) |
| ATCC BAA-44 (Iberian)[c] | 98/26821 (EMRSA-15/b3) | 3680 (EMRSA-GR1) |
| CCUG 41787 (Sa 501 V)[e] | 98/24344 (EMRSA-15/b7) | 3713 (EMRSA-GR1a) |
| CCUG 38266 (II)[e] | 99/1139 (EMRSA-16/a2) | 98S46 (Belgian epidemic clone 3b) |
| NCTC 8325[b] | 99/159 (EMRSA-16/a14) | 97S96 (Belgian epidemic clone 1a) |
| NCTC 11939 (EMRSA-1)[c] | 6 (D) | 97S98 (Belgian epidemic clone 1b) |
| | 13 (A') | 97S99 (Belgian epidemic clone 2a) |
| Canadian epidemic MRSA (Type designation)[d] | 14 (A') | 97S100 (Belgian epidemic clone 2b) |
| CMRSA-1 | 18 (A) | 97S101 (Belgian epidemic clone 3a) |
| CMRSA-2 | 25 (F') | 134/93 (N. German EMRSA I) |

TABLE 1-continued

Reference *Staphylococcus aureus* strains used in the present invention[a]

| Strain number | Strain number | Strain number |
|---|---|---|
| CMRSA-3 | 30 (G) | 1000/93 (Hannover area EMRSA III) |
| CMRSA-4 | 33 (F) | 1450/94 (N. German EMRSA 1a) |
| CMRSA-5 | 54 (B) | 825/96 (Berlin epidemic EMRSA IV) |
| CMRSA-6 | 60 (A″) | 842/96 (Berlin epidemic EMRSA IVa) |
| HARMONY collection or European epidemic MRSA | 80 (E) | 2594-1/97 (S. German EMRSA II a) |
| (Type designation)[e] | 98 (C) | 1155-2/98 (S. German EMRSA II) |
| 96158 (B) | 162 (A) | 1442/98 (Hannover area EMRSA IIIa) |
| 97117 (A) | 920 (B) | N8-890/99 (Sa 543 VI) IIIa) |
| 97117 (A) | 920 (B) | N8-890/99 (Sa 543 VI) |
| 97118 (A) | 95035 (A) | N8-3756/90 (Sa544 I) |
| 97120 (B) | 97121 (B) | 9805-01937 (V) |
| 97151 (B) | BM10828 (C) | AK 541 (IV) |
| 97392 (B) | BM10882 (C) | ON 408/99 (VII) |
| 97393 (A) | 37481 (Seinajoki E 14) | AO 9973/97 (III) |

[a]All *S. aureus* strains are resistant to methicillin except where otherwise indicated.
[b]These *S. aureus* strains are sensitive to oxacillin (MSSA).
[c]Informations on these strains and type designation based on pulse-field gel electrophoresis are from (6).
[d]Information on these strains and type designation based on pulse-field gel electrophoresis are from (47).
[e]Information on these strains and type designation based on pulse-field gel electrophoresis are available at http://www.phls.co.uk/inter/harmony/menu.htm.

TABLE 2

Evaluation of the MRSA-specific primers targeting MREJ types i to x using DNA from a variety of methicillin-sensitive and methicillin-resistant *Staphylococcus aureus* strains.

| *Staphylococcus aureus* strains[a] | PCR results | |
|---|---|---|
| (number) | Positive (%) | Negative (%) |
| MRSA (1657) | 1640 (99) | 17 (1) |
| MSSA (569) | 26 (4.6) | 543 (95.4) |

[a]MRSA, methicillin-resistant *Staphylococcus aureus*; MSSA, methicillin-sensitive *Staphylococcus aureus*. Reference *S. aureus* strains used are listed in Table 1. The origin of the *S. aureus* clinical isolates is described in the text.

TABLE 3

Origin of 17 MRSA strains not amplifiable using primers targeting MREJ types i to x.

| *Staphylococcus aureus* strain designation: | | |
|---|---|---|
| Original | CCRI[a] | Origin |
| 6-9637 | CCRI-12157 | Tempe, USA |
| 15-3967 | CCRI-12198 | New York, USA |
| 15-3972 | CCRI-12199 | New York, USA |
| 91 2290 | CCRI-12719 | Australia |
| SS1757 | CCRI-11976 | Houston, USA |
| 255 D | CCRI-12382 | Brazil |
| 106 I | CCRI-12383 | Brazil |
| 232 D | CCRI-12376 | Brazil |
| 6881 | CCRI-12593 | Spain |
| 5109 | CCRI-11999 | Wilmington, USA |
| BK793 | CCRI-9887 | Cairo, Egypt |
| 21 1 8424 | CCRI-12845 | Japan |
| SE46-1 | CCRI-9772 | Toronto, Canada |
| 1059 | CCRI-12524 | Italy |
| 1016 | CCRI-12535 | Italy |

TABLE 3-continued

Origin of 17 MRSA strains not amplifiable using primers targeting MREJ types i to x.

| *Staphylococcus aureus* strain designation: | | |
|---|---|---|
| Original | CCRI[a] | Origin |
| 816867 | CCRI-12905 | Rennes, France |
| 20 1 6060 | CCRI-12810 | Taiwan, China |

[a]CCRI stands for "Collection of the Centre de Recherche en Infectiologie".

TABLE 8

Novel *Staphylococcus aureus* MREJ[a] nucleotide sequences

| | *S. aureus* strain designation | | |
|---|---|---|---|
| SEQ ID | Original | CCRI[c] | Sequence[a,b] |
| 15 | SS1757 | CCRI-11976 | MREJ type xiii |
| 16 | 5109 | CCRI-11999 | MREJ type xiv |
| 17 | 6-9637 | CCRI-12157 | MREJ type xi |
| 18 | 15-3967 | CCRI-12198 | MREJ type xi |
| 19 | 15-3962 | CCRI-12199 | MREJ type xi |
| 20 | 91 2290 | CCRI-12719 | MREJ type xii |
| 21 | 21 1 8424 | CCRO-12845 | MREJ type xvi |
| 25 | 255 D | CCRI-12382 | MREJ type xiii |
| 26 | 106 I | CCRI-12383 | MREJ type xiii |
| 39 | 1059 | CCRI-12524 | MREJ type xviii |
| 40 | 1016 | CCRI-12535 | MREJ type xviii |
| 41 | 20 1 6060 | CCRI-12810 | MREJ type xix |
| 42 | 816867 | CCRI-12905 | MREJ type xx |
| 55 | SE46-1 | CCRI-9772 | MREJ type xvii |
| 56 | BK793 | CCRI-9887 | MREJ type xv |

[a]MREJ refers to mec right extremity junction and includes sequences from the SCCmec right extremity and chromosomal DNA to the right of the SCCmec integration site.
[b]Sequence refers to the target gene
[c]CCRI stands for "Collection for the Centre de Recherche en Infectiologie"

TABLE 9

Novel PCR amplification primers developed to detect MREJ types xi-xx

| Originating target DNA MREJ type | Originating target DNA SEQ ID NO | Oligo Position[a] | Oligo SEQ ID NO |
|---|---|---|---|
| MREJ type xvii | 55 | 954[b] | 4 |
| MREJ type xviii | 40 | 1080 | 7 |
| MREJ type xx | 42 | 987[b] | 8 |
| MREJ type xix | 41 | 581[b] | 9 |
| MREJ type xv | 38 | 624 | 23 |
| MREJ type xv | 56 | 566[b] | 24 |
| MREJ type ix, xiii, xiv | 15 | 756[b] | 28 |
| MREJ type xi | 17 | 615[b] | 34 |
| MREJ type xii | 20 | 612[b] | 35 |
| MREJ type xv | 56 | 457 | 48 |
| MREJ type xv | 56 | 564[b] | 49 |
| MREJ type xi | 17 | 956[b] | 51 |
| MREJ type xii | 20 | 1053[b] | 52 |
| MREJ type xvii | 55 | 415 | 57 |
| MREJ type xvii | 55 | 558 | 58 |

[a]Position refers to nucleotide position of 5' end of primer
[b]Primer is reverse-complement of target sequence

TABLE 10

Other amplification and/or sequencing primers and probes found in the sequence listing

| SEQ ID NO | Source | Target | Originating DNA Position[a] | SEQ ID NO |
|---|---|---|---|---|
| 27 | Oliveira and de Lencastre. 2002, Antimicrob. Agents Chemother. 46: 2155-2161 | SCCmec | — | — |
| 29 | International Patent Application PCT/CA02/00824.[b] | MREJ types ix, xiii, and xiv | 652[c] | 29 |
| 30 | International Patent Application PCT/CA02/00824.[b] | orfX | 325 | 18 |
| 31 | International Patent Application PCT/CA02/00824.[b] | orfX | 346[c] | 18 |
| 32 | International Patent Application PCT/CA02/00824.[b] | orfX | 346[c] | 20 |
| 33 | International Patent Application PCT/CA02/00824.[b] | orfX | — | — |
| 36 | International Patent Application PCT/CA02/00824.[b] | MREJ types i, ii, and xvi | 574[c] | 21 |
| 43 | International Patent Application PCT/CA02/00824.[b] | orfX | 367[c] | 18 |
| 44 | International Patent Application PCT/CA02/00824.[b] | orfX | 98 | 38 |
| 45 | International Patent Application PCT/CA02/00824.[b] | orfX | 401 | 18 |
| 50 | International Patent Application PCT/CA02/00824.[b] | mecA | 6945[c] | 22 |
| 53 | Oliveira and de Lencastre, 2002, Antimicrob. Agents Chemother. 46: 2155-2161 | SCCmec | — | — |
| 54 | International Patent Application PCT/CA02/00824.[b] | MREJ types i and ii | — | — |
| 60 | WO96/08582[d] | putative membrane protein | | |
| 61 | WO96/08582[d] | putative membrane protein | | |
| 62 | This patent | orfX | 193 | 20 |
| 63 | International Patent Application PCT/CA02/00824.[b] | mecA | 6798 | 22 |
| 65 | International Patent Application PCT/CA02/00824.[b] | MREJ type vi | 642[c] | 191[b] |
| 66 | International Patent Application PCT/CA02/00824.[b] | MREJ types ii, viii, ix, xiii, xiv | 514 | 167[b] |
| 73 | This patent | MREJ type x | 1913[c] | 69 |
| 74 | International Patent Application PCT/CA02/00824.[b] | MREJ type vii | 503 | 189[b] |
| 75 | International Patent Application PCT/CA02/00824.[b] | MREJ type viii | 601 | 167[b] |
| 76 | This patent | orfX | 193 | 17 |

[a]Position refers to nucleotide position of the 5' end of primer (on the target sequence).
[b]SEQ ID NOs from International Patent Application PCT/CA02/00824.
[c]Primer is reverse-complement of target sequence.
[d]SEQ ID NOs from WO96/08582.

TABLE 11

Length of amplicons obtained with primer pairs for MREJ types xi-xx

| Oligo Pair (SEQ ID NO) | Target DNA | Amplicon length[a] |
|---|---|---|
| 24/30 | MREJ type xv | 265 |
| 24/44 | MREJ type xv | 603 |
| 24/45 | MREJ type xv | 189 |
| 24/62 | MREJ type xv | 397 |
| 28/30 | MREJ type xiii, xiv | 464 (type xiii); 668 (type xiv) |
| 28/44 | MREJ type xiii, xiv | 802[b] (type xiii); 1006[b] (type xiv) |
| 28/45 | MREJ type xiii, xiv | 388 (type xiii); 592 (type xiv) |
| 28/76 | MREJ type xiii | 596 (type xiii) |
| 29/30 | MREJ type xiii, xiv | 267 (type xiii); 471 (type xiv) |
| 29/44 | MREJ type xiii, xiv | 605[b] (type xiii); 809[b] (type xiv) |
| 29/45 | MREJ type xiii, xiv | 191 (type xiii); 395 (type xiv) |
| 29/59 | MREJ type xiv | 605 |
| 29/76 | MREJ type xiii | 399 |
| 34/30 | MREJ type xi | 328 |
| 34/44 | MREJ type xi | 661[b] |
| 34/45 | MREJ type xi | 247 |
| 34/76 | MREJ type xi | 455 |
| 35/30 | MREJ type xii | 311 |
| 35/44 | MREJ type xii | 649[b] |
| 35/45 | MREJ type xii | 235 |
| 35/62 | MREJ type xii | 443 |
| 36/44 | MREJ type xvi | 348[b] |
| 4/30 | MREJ type xvii | 690 |
| 4/44 | MREJ type xvii | 968[b] |
| 4/45 | MREJ type xvii | 614 |
| 4/62 | MREJ type xvii | 822 |
| 7/30 | MREJ type xviii | 780[b] |
| 7/44 | MREJ type xviii | 1119[b] |
| 7/45 | MREJ type xviii | 704 |
| 7/59 | MREJ type xviii | 912[b] |
| 8/30 | MREJ type xx | 1076[b] |
| 8/44 | MREJ type xx | 1415[b] |
| 8/45 | MREJ type xx | 1000 |
| 8/59 | MREJ type xx | 1208[b] |
| 9/30 | MREJ type xix | 657[b] |
| 9/44 | MREJ type xix | 996[b] |
| 9/45 | MREJ type xix | 581 |
| 9/59 | MREJ type xix | 789[b] |

[a]Amplicon length is given in base pairs for MREJ types amplified by the set of primers
[b]Amplicon length is based on analysis by agarose gel electrophoresis

TABLE 12

Percentage of sequence identity for the first 500 nucleotides of SCCmec right extremities between 19 types of MREJ[a,b]

|  | i[d] | ii | v | i | ii | iii | x[f] | i | ii | iii | iv[e] | v[c] | vi | vii | viii | ix | x |
|---|---|---|---|---|---|---|---|---|---|---|---|---|---|---|---|---|---|
| i[d] | 00 | 4.4 | 9.1 | 0.4 | 2.9 | 3.2 | 1.5 | 0.8 | 1.1 | 0.2 | 2.4 | 1.2 | 9.6 | 00.0 | 2.1 | 4.1 | 2.5 | 0.4 |
| ii |  | 4.2 | 2.1 | 3.3 | 2.9 | 2.5 | 2.2 | 5.7 | 3.2 | 9.2 | 4.1 | 3.0 | 9.6 | 00.0 | 1.9 | 5.4 | 5.1 | 5.7 |
| v |  |  | 0.1 | 5.8 | 5.0 | 4.4 | 2.3 | 5.0 | 5.7 | 4.9 | 9.9 | 6.2 | 9.5 | 4.2 | 3.1 | 6.7 | 3.5 | 5.3 |
| i |  |  |  | 5.2 | 0.3 | 1.6 | 2.1 | 9.9 | 2.7 | 8.2 | 2.7 | 9.8 | 0.2 | 2.1 | 9.6 | 0.3 | 7.2 | 1.4 |
| ii |  |  |  |  | 5.0 | 1.3 | 6.5 | 3.2 | 1.2 | 3.6 | 3.8 | 0.2 | 7.2 | 3.3 | 2.3 | 9.8 | 3.8 | 9.8 |
| iii |  |  |  |  |  | 5.1 | 4.5 | 3.8 | 2.0 | 3.2 | 3.9 | 7.6 | 2.9 | 9.4 | 3.4 | 2.2 | 5.8 |
| x[f] |  |  |  |  |  |  | 2.8 | 9.4 | 2.7 | 2.0 | 4.8 | 1.8 | 9.7 | 2.5 | 3.2 | 4.7 | 1.1 | 1.9 |
| i |  |  |  |  |  |  |  | 4.0 | 1.1 | 1.9 | 1.1 | 3.3 | 7.6 | 2.2 | 0.9 | 1.2 | 2.4 | 9.1 |
| ii |  |  |  |  |  |  |  |  | 2.9 | 0.4 | 00 | 00 | 0.4 | 5.7 | 0.8 | 0.2 | 1.6 | 7.3 |
| iii |  |  |  |  |  |  |  |  |  | 8.0 | 6.0 | 4.8 | 7.1 | 3.2 | 0.5 | 7.1 | 1.8 | 3.6 |
| iv[e] |  |  |  |  |  |  |  |  |  |  | 2.5 | 7.8 | 7.5 | 9.2 | 3.3 | 3.7 | 4.7 | 5.6 |
| v[c] |  |  |  |  |  |  |  |  |  |  |  | 00 | 0.4 | 4.1 | 0.9 | 5.0 | 0.6 | 2.9 |
| vi |  |  |  |  |  |  |  |  |  |  |  |  | 1.2 | 3.0 | 5.7 | 4.2 | 1.6 | 2.9 |
| vii |  |  |  |  |  |  |  |  |  |  |  |  |  | 9.6 | 0.9 | 7.5 | 4.1 | 6.5 |
| viii |  |  |  |  |  |  |  |  |  |  |  |  |  |  | 1.9 | 5.4 | 5.1 | 5.7 |
| ix |  |  |  |  |  |  |  |  |  |  |  |  |  |  |  | 0.0 | 3.3 | 2.5 |
| x |  |  |  |  |  |  |  |  |  |  |  |  |  |  |  |  | 3.4 | 5.7 |
|  |  |  |  |  |  |  |  |  |  |  |  |  |  |  |  |  |  | 5.5 |

[a]"First 500 nucleotides" refers to the 500 nucleotides within the SCCmec right extremity, starting from the integration site of SCCmec in the *Staphylococcus aureus* chromosome as shown on FIG. 3.
[b]Sequences were extracted from International patent application PCT/CA02/00824 (SEQ ID NOs.: 1, 2, 232, 46, 50, 171, 166, 167 and 168 for types i to ix, respectively).
MREJ type x was excluded from the sequence comparison because it is deleted from the completed orfX, the integration site, and part of the SCCmec right extremity.
Sequences for types xi to xx were extracted from SEQ ID NOs.: 18, 20, 25, 16, 56, 21, 55, 39, 41 and 42, respectively.
[c]Sequence from the SCCmec right extremity of MREJ type xv is limited to 126 nucleotides.
[d]The first 102 nucleotides from the SCCmec right extremity of MREJ type ii were excluded from the sequence comparison.
[e]The first 206 nucleotides from the SCCmec right extremity of MREJ type xiv were excluded from the sequence comparison.
[f]The first 102 nucleotides from the SCCmec right extremity of MREJ type ix were excluded from the sequence comparison.

What is claimed is:

1. A method to detect the presence of an MREJ type xiii methicillin resistant *Staphylococcus aureus* (MRSA) strain comprising:

contacting a first primer and a second primer with a sample to be analyzed for the presence of said MREJ type xiii MRSA strain, said MREJ type xiii MRSA strain including a Staphylococcal cassette chromosome mec (SCC-mec) element containing a mecA gene inserted into chromosomal DNA, thereby generating a polymorphic right extremity junction (MREJ) type xiii sequence that comprises sequences from both the SCCmec element right extremity and chromosomal DNA adjoining said right extremity, wherein said first and second primers are at least 10 nucleotides in length, and wherein said first primer is specific for and hybridizes with said SCCmec element right extremity of an MREJ type xiii sequence selected from the group consisting of SEQ ID NOs: 15, 25 and 26 and complements thereof, and wherein said second primer hybridizes with a chromosomal sequence of *S. aureus*, wherein said first primer and said second primer together generate a first amplicon that spans the mec right extremity junction of MREJ type xiii sequences under amplification conditions only if said MREJ type xiii MRSA strain is present in the sample; and wherein said contacting of said first primer and said second primer takes place under annealing conditions wherein generating and detecting the presence of said first amplicon as indicative of the presence of said MREJ type xiii MRSA strain in the sample.

2. The method of claim 1, wherein said chromosomal sequence of *S. aureus* is orfX.

3. The method of claim 1, wherein said first primer and said second primer comprise nucleic acid sequences selected from the group consisting of SEQ ID NOs: 29 and 45; SEQ ID NOs: 29 and 30; SEQ ID NOs: 29 and 76; and SEQ ID NOs: 29 and 44.

4. The method of claim 1, comprises contacting at least one primer and/or probe comprising a nucleic acid sequence selected from the group consisting of SEQ ID NOs: 29, 30, 31, 32, 33, 44, 45, and 76 with said sample.

5. The method of claim 1, wherein the detecting comprises a method selected from the group consisting of: agarose gel electrophoresis, fluorescence resonance energy transfer, chemiluminescence, potentiometry, mass spectrometry, plasmon resonance, polarimetry, colorimetry, flow cytometry, scanometry, and DNA sequencing or any combination thereof.

6. The method of claim 1, further comprising detecting the presence of at least one further methicillin-resistant *Staphylococcus aureus* (MRSA) strain in said sample, said at least one further MRSA strain being an MREJ type xi, xii, xiv, xv, xvi, xvii, xviii, xix, or xx MRSA strain, comprising: contacting a third primer and a fourth primer with the sample, said MREJ type xi, xii, xiv, xv, xvi, xvii, xviii, xix, or xx MRSA strain including a Staphylococcal cassette chromosome mec (SCCmec) element containing a mecA gene inserted into chromosomal DNA, thereby generating a polymorphic right extremity junction (MREJ) type xi, xii, xiv, xv, xvi, xvii, xviii, xix, or xx sequence that comprises sequences from both the SCCmec right extremity and chromosomal DNA adjoining said right extremity, wherein said third primer and said fourth primer together generate a second amplicon that spans the mec right extremity junction of the MREJ type xi, xii, xiv, xv, xvi, xvii, xviii, xix, or xx sequence under amplification conditions only if said MREJ type xi, xii, xiv, xv, xvi, xvii, xviii, xix, or xx MRSA strain, respectively, is present in the sample and wherein said contacting takes place under annealing conditions; and detecting the presence of said second amplicon as indicative of the presence of said MREJ type i, xi, xii, xiv, xv, xvi, xvii, xviii, xix, or xx MRSA strain in the sample.

7. The method of claim 6, wherein said method comprises contacting a nucleic acid sequence selected from the group consisting of: SEQ ID NOs: 51, 30, 31, 32, 33, 52, 29, 30, 31, 32, 24, 36, 44, 4, 7, 9, and 8 with said sample.

8. The method of claim 6, wherein said third primer and said fourth primers comprise nucleic acid sequences selected from the group consisting of one primer SEQ ID NOs: 34 and 45, SEQ ID NOs: 34 and 30, SEQ ID NOs: 34 and 76; SEQ ID NOs: 34 and 44; SEQ ID NOs: 35 and 45; SEQ ID NOs: 35 and 30; SEQ ID NOs: 35 and 62; SEQ ID NOs: 35 and 44; SEQ ID NOs: 29 and 45; SEQ ID NOs: 29 and 30; SEQ ID NOs: 29 and 59; SEQ ID NOs: 29 and 44; SEQ ID NOs: 24 and 45; SEQ ID NOs: 24 and 30; SEQ ID NOs: 24 and 62; SEQ ID NOs: 24 and 44; SEQ ID NOs: 36 and 44; for SEQ ID NOs: 4 and 45; SEQ ID NOs: 4 and 30; SEQ ID NOs: 4 and 62; SEQ ID NOs: 4 and 44; SEQ ID NOs: 7 and 45; SEQ ID NOs: 7 and 30; SEQ ID NOs: 7 and 59; SEQ ID NOs: 7 and 44; SEQ ID NOs: 9 and 45; SEQ ID NOs: 9 and 30; SEQ ID NOs: 9 and 59; SEQ ID NOs: 9 and 44; SEQ ID NOs: 8 and 45; SEQ ID NOs: 8 and 30; SEQ ID NOs: 8 and 59; and SEQ ID NOs: 8 and 44.

9. The method of claim 1, further comprising detecting the presence or absence of at least one further methicillin-resistant *Staphylococcus aureus* (MRSA) strain in said sample, said at least one further MRSA strain being an MREJ type i, ii, iii, iv, v, vi, vii, viii, ix, or x MRSA strain comprising: contacting a third primer and a fourth primer with the sample, said MREJ type i, ii, iii, iv, v, vi, vii, viii, ix, or x MRSA strain including a Staphylococcal cassette chromosome mec (SCCmec) element containing a mecA gene inserted into chromosomal DNA, thereby generating a polymorphic right extremity junction (MREJ) type i, ii, iii, iv, v, vi, vii, viii, ix, or x sequence that comprises sequences from both the SCCmec right extremity and chromosomal DNA adjoining said right extremity wherein said third primer and said fourth primer together generate a second amplicon that spans the right extremity junction of the MREJ type i, ii, iii, iv, v, vi, vii, viii, ix, or x sequence under amplification conditions only if said MREJ type i, ii, iii, iv, v, vi, vii, viii, ix, or x MRSA strain, respectively, is present in the sample and wherein said contacting takes place under annealing conditions; and detecting the presence of said second amplicon as indicative of the presence of said MREJ type i, ii, iii, iv, v, vi, vii, viii, ix, or x MRSA strain in the sample.

10. The method of claim 9, wherein said third primer and said fourth primer comprise nucleic acid sequences selected from the group consisting of: SEQ ID NOs: 30 and 36; SEQ ID NOs: 30 and 70; SEQ ID NOs: 30 and 71; SEQ ID NOs: 30 and 72; SEQ ID NOs: 30 and 65; SEQ ID NOs: 30 and 74; SEQ ID NOs: 30 and 75; SEQ ID NOs: 30 and 29; and SEQ ID NOs: 73 and 77.

11. The method of claim 9, wherein the first, second, third and fourth primers are used together in the same physical enclosure.

12. The method of claim 11, wherein the first and second primers probes are chosen to hybridize under the same hybridization conditions.

13. The method of claim 6, wherein the first second, third and fourth primers are used together in the same physical enclosure.

14. The method of claim 1, wherein the first and second primers are chosen to hybridize under the same hybridization conditions.

* * * * *

SEQUENCE LISTING

<160> NUMBER OF SEQ ID NOS: 85

<210> SEQ ID NO 1
<211> LENGTH: 21
<212> TYPE: DNA

```
<213> ORGANISM: Artificial Sequence
<220> FEATURE:
<223> OTHER INFORMATION: Synthetically prepared nucleic acid sequence

<400> SEQUENCE: 1
gcaggaacaa acagatgaag a                                              21

<210> SEQ ID NO 2
<211> LENGTH: 19
<212> TYPE: DNA
<213> ORGANISM: Artificial Sequence
<220> FEATURE:
<223> OTHER INFORMATION: Synthetically prepared nucleic acid sequence

<400> SEQUENCE: 2
tcggctctac cctcaacaa                                                 19

<210> SEQ ID NO 3
<211> LENGTH: 19
<212> TYPE: DNA
<213> ORGANISM: Artificial Sequence
<220> FEATURE:
<223> OTHER INFORMATION: Synthetically prepared nucleic acid sequence

<400> SEQUENCE: 3
tcgcagggat ggtattgaa                                                 19

<210> SEQ ID NO 4
<211> LENGTH: 19
<212> TYPE: DNA
<213> ORGANISM: Artificial Sequence
<220> FEATURE:
<223> OTHER INFORMATION: Synthetically prepared nucleic acid sequence

<400> SEQUENCE: 4
caccctgcaa gatatgttt                                                 19

<210> SEQ ID NO 5
<211> LENGTH: 25
<212> TYPE: DNA
<213> ORGANISM: Artificial Sequence
<220> FEATURE:
<223> OTHER INFORMATION: Synthetically prepared nucleic acid sequence

<400> SEQUENCE: 5
ttcgttgaaa gaagagaaaa ttaaa                                          25

<210> SEQ ID NO 6
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 6 gcttttttt ctttattatc aagtatc                                         27

<210> SEQ ID NO 7
<211> LENGTH: 25
<212> TYPE: DNA
<213> ORGANISM: Artificial Sequence
<220> FEATURE:
<223> OTHER INFORMATION: Synthetically prepared nucleic acid sequence

<400> SEQUENCE: 7
aatggaattt gttaatttca taaat                                          25
```

<210> SEQ ID NO 8
<211> LENGTH: 25
<212> TYPE: DNA
<213> ORGANISM: Artificial Sequence
<220> FEATURE:
<223> OTHER INFORMATION: Synthetically prepared nucleic acid sequence

<400> SEQUENCE: 8
ttccgaagtc ataatcaatc aaatt                                      25

<210> SEQ ID NO 9
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 9
ttccgaagct aattctgtta ata                                        23

<210> SEQ ID NO 10
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 10
aggcgttaaa aatcctgata ctg                                        23

<210> SEQ ID NO 11
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 11
aagccaattc aatttgtaat gc                                         22

<210> SEQ ID NO 12
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 12
aacccctcct ctgtaattag tg                                         22

<210> SEQ ID NO 13
<211> LENGTH: 21
<212> TYPE: DNA
<213> ORGANISM: Artificial Sequence
<220> FEATURE:
<223> OTHER INFORMATION: Synthetically prepared nucleic acid sequence

<400> SEQUENCE: 13
agcggtggag tgcaaataga t                                          21

<210> SEQ ID NO 14
<211> LENGTH: 23
<212> TYPE: DNA
<213> ORGANISM: Artificial Sequence
<220> FEATURE:

<223> OTHER INFORMATION: Synthetically prepared nucleic acid sequence

<400> SEQUENCE: 14
ttgctggaca tcaacagtat cat                                            23

<210> SEQ ID NO 15
<211> LENGTH: 1032
<212> TYPE: DNA
<213> ORGANISM: Staphylococcus aureus

<400> SEQUENCE: 15

```
accattttag ctgtagggaa actaaaagag aaatattgga agcaagccat agcagaatat      60
gaaaaacgtt taggcccata caccaagata gacatcatag aagttccaga cgaaaaagca     120
ccagaaaata tgagcgacaa agaaattgag caagtaaaag aaaagaagg ccaacgaata      180 ctagccaaaa ttaaaccaca atccacagtc attacattag aaatacaagg aaagatgcta     240
tcttccgaag gattggccca agaattgaac caacgcatga cccaagggca aagcgacttt     300
gtattcgtca ttggcggatc aaacggcctg cacaaggacg tcttacaacg cagtaactac     360
gcactatcat tcagcaaaat gacattccca catcaaatga tgcgggttgt gttaattgag     420
caagtgtata gagcatttaa gattatgcgt ggagaagcat atcataagtg atgcggtttt     480
tattaattag ttgctaaaaa atgaagtatg caatattaat tattattaaa ttttgatata     540
tttaaagaaa gattaagttt agggtgaatg aatggcttat caaagtgaat atgcattaga     600
aaatgaagta cttcaacaac ttgaggaatt gaactatgaa agagtaaata tacataaat     660 taaattagaa attaatgaat atctcaaaga actaggagtg ttgaaaaatg aataagcaga     720
caaatactcc agaactaaga tttccagagt ttgatgagga atggaaaaaa aggaaattag     780
gtgaagtagt aaattataaa aatggtggtt catttgaaag tttagtgaaa aaccatggtg     840
tatataaact cataactctt aaatctgtta atacagaagg aaagttgtgt aattctggaa     900
aatatatcga tgataaatgt gttgaaacat tgtgtaatga tactttagta atgatactga     960
gcgagcaagc accaggacta gttggaatga ctgcaattat acctaataat aatgagtatg    1020
tactaaatca ac                                                       1032
```

<210> SEQ ID NO 16
<211> LENGTH: 1116
<212> TYPE: DNA
<213> ORGANISM: Staphylococcus aureus

<400> SEQUENCE: 16

```
accattttag ctgtagggaa actaaaagag aaatattgga agcaagccat agcagaatat      60
gaaaaacgtt taggcccata caccaagata gacatcatag aagttccaga cgaaaaagca     120
ccagaaaata tgagcgacaa agaaattgag caagtaaaag aaaagaagg ccaacgaata      180 ctagccaaaa ttaaaccaca atccacagtc attacattag aaatacaagg aaagatgcta     240
tcttccgaag gattggccca agaattgaac caacgcatga cccaagggca aagcgacttt     300
gtattcgtca ttggcggatc aaacggcctg cacaaggacg tcttacaacg cagtaactac     360
gcactatcat tcagcaaaat gacattccca catcaaatga tgcgggttgt gttaattgag     420
caagtgtata gagcatttaa gattatgcgt ggagaagcat atcataaatg atgcggtttt     480
ttcagccgct tcataaaggg attttgaatg tatcagaaca tatgaggttt atgtgaattg     540
ctgttatgtt tttaagaagc atatcataaa tgatgcggtt ttttcagccg cttcataaag     600
ggattttgaa tgtatcagaa catatgaggt ttatgtgaat tgctgttatg tttttaagaa     660
```

```
gcatatcata agtgatgcgg ttttattaa ttagttgcta aaaaatgaag tatgcaatat    720
taattattat taaattttga tatatttaaa gaaagattaa gtttagggtg aatgaatggc    780
ttatcaaagt gaatatgcat tagaaaatga agtacttcaa caacttgagg aattgaacta    840
tgaaagagta aatatacata atattaaatt agaaattaat gaatatctca aagaactagg    900
agtgttgaaa aatgaataag cagacaaata ctccagaact aagatttcca gagtttgatg    960
aggaatggaa aaaaggaaa ttaggtgaag tagtaaatta taaaaatggt ggttcatttg   1020
aaagtttagt gaaaaaccat ggtgtatata aactcataac tcttaaatct gttaatacag   1080
aaggaaagtt gtgtaattct ggaaaatata tcgatg                            1116
```

<210> SEQ ID NO 17
<211> LENGTH: 1100
<212> TYPE: DNA
<213> ORGANISM: Staphylococcus aureus

<400> SEQUENCE: 17

```
accattttag ctgtagggaa actaaaagag aaatattgga agcaagccat agcagaatat     60
gaaaaacgtt taggcccata caccaagata gacatcatag aagttccaga cgaaaaagca    120
ccagaaaata tgagcgacaa agaaattgag caagtaaaag aaaagaagg ccaacgaata    180 ctagccaaaa ttaaaccaca atccacagtc attacattag aaatacaagg aaagatgcta    240
tcttccgaag gattgcccca agaattgaac caacgcatga cccaagggca agcgactttt    300
gtattcgtca ttggcggatc aaacggcctg cacaaggacg tcttacaacg cagtaactac    360
gcactatcat tcagcaaaat gacattccca catcaaatga tgcgggttgt gttaattgag    420
caagtgtata gagcatttaa gattatgcgt ggagaagcgt atcacaaata aaactaaaaa    480
ataagttgta taacttatt tttgaaattg gttaagtata taatatctcc aataaaatgt    540
agttaactta cgataatgct gaactatagc tttgtaaact aaaatgtaaa taattacaat    600
caaattgcaa caatatagtt caagaatgct acaatttgag gacagattga tagcattaat    660 cccttttaaaa tgaagctagg agataactta cattatgatt agtaaacaaa taaaggattt    720
acgaaagcaa cataattata ctcaagaaga gctagctgaa aaattaaata cttcaagaca    780 aacaattct aaatgggaac aaggtatttc agaaccagac ttaattatgc ttatgcaatt    840
gtcacaatta tttctgtta gtacagacta tctcattaca ggaagtgaca atattattaa    900
aaaagataat aaaagctatt atgaaatgaa ttttgggca tttatgtctg aaaaatggtg    960
ggtaattatt attatagtaa tcataattg tggaacaata ggacaaatt tttcaaacta   1020 atgtaagtat ctctcaaata ttttgggagg ttttattatg aaaatcaaaa aattattaaa   1080
gacattatta attattttat                                              1100
```

<210> SEQ ID NO 18
<211> LENGTH: 1118
<212> TYPE: DNA
<213> ORGANISM: Staphylococcus aureus

<400> SEQUENCE: 18

```
atgaaaatca ccattttagc tgtagggaaa actaaaagaga aatattggaa gcaagccata     60
gcagaatatg aaaaacgttt aggcccatac accaagatag acatcataga agttccagac    120
gaaaaagcac cagaaaatat gagcgacaaa gaaattgagc aagtaaaaga aaagaaggc    180 caacgaatac tagccaaaat caaaccacaa tcaacagtca ttacattaga aatacaagga    240
```

```
aagatgctat cttccgaagg attggcccaa gaattgaacc aacgcatgac ccaagggcaa        300
agcgactttg tattcgtcat tggcggatca aacggcctgc acaaggacgt cttacaacgc        360
agtaactacg cactatcatt cagcaaaatg acattcccac atcaaatgat gcgggttgtg        420
ttaattgaac aagtgtacag agcatttaag attatgcgtg gagaagcgta tcacaaataa        480
aactaaaaaa taagttgtat ataacttatt ttgaaattgg ttaagtatat agtatctcca        540
ataaaatgta gttaacttac gataatgctg aactatagct ttgtaaacta aaatgtaaat        600
aattacaatc aaattgcaac aatatagttc aagaatgcta caatttgagg acagattgat        660
agcattaatc cctttaaaat gaagctagga gataacttac attatgatta gtaaacaaat        720
aaaggattta cgaaagcaac ataattatac tcaagaagag ctagctgaaa aattaaatac        780
ttcaagacaa acaatttcta aatgggaaca aggtatttca gaaccagact taattatgct        840
tatgcaattg tcacaattat tttctgttag tacagactat ctcattacag gaagtgacaa        900
tattattaaa aaagataata aaagctatta tgaaatgaat ttttgggcat ttatgtctga        960
aaaatggtgg gtaattatta ttatagtaat cataatttgt ggaacaatag acaaatttt       1020 ttcaaactaa tgtaagtatc tctcaaatat tttgggaggt tttattatga aaatcaaaaa      1080
attattaaag acattattaa ttattttatt atgttttg                              1118

<210> SEQ ID NO 19
<211> LENGTH: 1168
<212> TYPE: DNA
<213> ORGANISM: Staphylococcus aureus

<400> SEQUENCE: 19
atgaaaatca ccatttttagc tgtagggaaa ctaaaagaga atattggaa gcaagccata         60 gcagaatatg aaaaacgttt aggcccatac accaagatag acatcataga agttccagac        120
gaaaaagcac cagaaaatat gagcgacaaa gaaattgagc aagtaaaaga aaagaaggc        180 caacgaatac tagccaaaat caaaccacaa tcaacagtca ttacattaga aatacaagga        240
aagatgctat cttccgaagg attggcccaa gaattgaacc aacgcatgac ccaagggcaa        300
agcgactttg tattcgtcat tggcggatca aacggcctgc acaaggacgt cttacaacgc        360
agtaactacg cactatcatt cagcaaaatg acattcccac atcaaatgat gcgggttgtg        420
ttaattgaac aagtgtacag agcatttaag attatgcgtg gagaagcgta tcacaaataa        480
aactaaaaaa taagttgtat ataacttatt ttgaaattgg ttaagtatat agtatctcca        540
ataaaatgta gttaacttac gataatgctg aactatagct ttgtaaacta aaatgtaaat        600
aattacaatc aaattgcaac aatatagttc aagaatgcta caatttgagg acagattgat        660
agcattaatc cctttaaaat gaagctagga gataacttac attatgatta gtaaacaaat        720
aaaggattta cgaaagcaac ataattatac tcaagaagag ctagctgaaa aattaaatac        780
ttcaagacaa acaatttcta aatgggaaca aggtatttca gaaccagact taattatgct        840
tatgcaattg tcacaattat tttctgttag tacagactat ctcattacag gaagtgacaa        900
tattattaaa aaagataata aaagctatta tgaaatgaat ttttgggcat ttatgtctga        960
aaaatggtgg gtaattatta ttatagtaat cataatttgt ggaacaatag acaaatttt       1020 ttcaaactaa tgtaagtatc tctcaaatat tttgggaggt tttattatga aaatcaaaaa      1080
attattaaag acattattaa ttattttatt atgttttgta ttgtctgtta ttgtgcaaaa      1140
tatttcaatg ctatggcata ttgtgagc                                         1168
```

<210> SEQ ID NO 20
<211> LENGTH: 1134
<212> TYPE: DNA
<213> ORGANISM: Staphylococcus aureus

<400> SEQUENCE: 20

| | | | | | |
|---|---|---|---|---|---|
| atgaaaatca | ccattttagc | tgtagggaaa | ctaaaagaga | atattggaa | gcaagccata | 60 |
| gcagaatatg | aaaaacgttt | aggcccatac | accaagatag | acatcataga | agttccagac | 120 |
| gaaaaagcac | cagaaaatat | gagcgacaaa | gaaattgagc | aagtaaaaga | aaagaaggc | 180 |
| caacgaatac | tagccaaaat | caaaccacaa | tccacagtca | ttacattaga | aatacaagga | 240 |
| aagatgctat | cttccgaagg | attggcccaa | gaattgaacc | aacgcatgac | ccaagggcaa | 300 |
| agcgactttg | tattcgtcat | tggcggatca | aacggcctgc | acaaggacgt | cttacaacgc | 360 |
| agtaactatg | cactatcatt | tagcaaaatg | acattcccac | atcaaatgat | gcgggttgtg | 420 |
| ttaattgaac | aagtgtatag | agcatttaag | attatgcgtg | gagaggcgta | tcataaataa | 480 |
| aactaaaaaa | cggattgtgt | ataatatatt | ttaaatataa | aaaggattga | ttttatgtta | 540 |
| aataaattag | aaaatgttag | ttataaatca | ttcgataatt | acactagtga | agatgatttg | 600 |
| actaaagtaa | atatatttttt | tggaagaaat | gggagtggaa | aaagctcatt | aagtgaatgg | 660 |
| ttaagaagac | tagataatga | aaaaagtgtt | atctttaata | ctggttactt | aaaaaataat | 720 |
| attgaagaag | ttgaagaaat | agatggtgtg | aatttggtta | ttggagaaga | atctataaat | 780 |
| catagtgacc | aaattaagca | tttaaatagc | gctataaata | gtttagaaaa | ttttattact | 840 |
| cggaaaaata | gtgaacttaa | gcattcaaaa | gaaagaattt | acaataaaat | gaatatcaga | 900 |
| ctaaatgaag | ctagagaaag | atttgaaata | ggtagtaatg | tggttaagca | gaagaggaat | 960 |
| gctgacaaag | atccagttaa | tgcttttttat | agttggaaga | aaaatgctaa | cgatataatt | 1020 |
| caagagatga | ctattgaatc | tttagatgaa | ttagaagaaa | gaataacaag | aaaagaagtc | 1080 |
| ttattaaata | atataaaaac | accaatttta | gcttttgatt | ataatgattt | tagt | 1134 |

<210> SEQ ID NO 21
<211> LENGTH: 818
<212> TYPE: DNA
<213> ORGANISM: Staphylococcus aureus

<400> SEQUENCE: 21

| | | | | | |
|---|---|---|---|---|---|
| aatattggaa | gcaagccata | gcagaatatg | aaaaacgttt | aggcccatac | accaagatag | 60 |
| acatcataga | agttccagac | gaaaaagcac | cagaaaatat | gagcgacaaa | gaaattgagc | 120 |
| aagtgtatag | agcatttaag | attatgcgtg | gagaagcata | tcataaatga | tgcggttttt | 180 |
| tcagccgctt | cataaaggga | ttttgaatgt | atcagaacat | atgaggttta | tgtgaattgc | 240 |
| tgttatgttt | ttaagaagct | tatcataagt | aatgaggttc | atgattttg | acatagttag | 300 |
| cctccgcagt | ctttcatttc | aagtaaataa | tagcgaaata | ttctttatac | tgaatactta | 360 |
| tagtgaagca | aagttctagc | tttgagaaaa | ttctttctgc | aactaaatat | agtaaattac | 420 |
| ggtaaaatat | aaataagtac | atattgaaga | aaatgagaca | taatatattt | tataatagga | 480 |
| gggaatttca | aatgatagac | aactttatgc | aggtccttaa | attaattaaa | gagaaacgta | 540 |
| ccaataatgt | agttaaaaaa | tctgattggg | ataaaggtga | tctatataaa | actttagtcc | 600 |
| atgataagtt | acccaagcag | ttaaaagtgc | atataaaaga | agataaatat | tcagttgtag | 660 |
| ggaaggttgc | tactgggaac | tatagtaaag | ttccttggat | ttcaatatat | gatgagaata | 720 |
| taacaaaaga | aacaaaggat | ggatattatt | tggtatatct | ttttcatccg | gaaggagaag | 780 |

```
gcatatactt atcttgaatc aaggatggtc aaagataa                              818
```

<210> SEQ ID NO 22
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 22

```
aacaggtgaa ttattagcac ttgtaag                                          27
```

<210> SEQ ID NO 23
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 23

```
gagcggattt atattaaaac tttg                                             24
```

<210> SEQ ID NO 24
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 24

```
gttgccatag attcaatttc taag                                             24
```

<210> SEQ ID NO 25
<211> LENGTH: 1090
<212> TYPE: DNA
<213> ORGANISM: Staphylococcus aureus

<400> SEQUENCE: 25

```
atgaaaatca ccattttagc tgtagggaaa ctaaaagaga atattggaa gcaagccata       60
gcagaatatg aaaaacgttt aggcccatac accaagatag acatcataga agttccagac    120
gaaaaagcac cagaaaatat gagcgacaaa gaaattgagc aagtaaaaga aaaagaaggc    180
caacgaatac tagccaaaat caaaccacaa tcaacagtca ttacattaga aatacaagga    240
aagatgctat cttccgaagg attggcccaa gaattgaacc aacgcatgac ccaagggcaa    300
agcgactttg tattcgtcat tggcggatca aacggcctgc acaaggacgt cttacaacgc    360
agtaactacg cactatcatt cagcaaaatg acattccac atcaaatgat gcgggttgtg    420
ttaattgaac aagtgtacag agcatttaag attatgcgtg gagaagcata tcataagtga    480
tgcggttttt attaattagt tgctaaaaaa tgaagtatgc aatattaatt attattaaat    540
tttgatatat ttaagaaag attaagttta gggtgaatga atggcttatc aaagtgaata    600
tgcattagaa aatgaagtac ttcaacaact tgaggaattg aactatgaaa gagtaaatat    660
acataatatt aaattagaaa ttaatgaata tctcaaagaa ctaggagtgt tgaaaaatga    720
ataagcagac aaatactcca gaactaagat ttccagagtt tgatgaggaa tggaaaaaaa    780
ggaaattagg tgaagtagta aattataaaa atggtggttc atttgaaagt ttagtgaaaa    840
accatggtgt atataaactc ataactctta aatctgttaa tacagaagga aagttgtgta    900
attctggaaa atatatcgat gataaatgtg ttgaaacatt gtgtaatgat actttagtaa    960
tgatactgag cgagcaagca ccaggactag ttggaatgac tgcaattata cctaataata   1020
```

-continued

```
atgagtatgt actaaatcaa cgagtagcag cactagtgcc taaacaattt atagatagtc    1080
aatttctatc                                                           1090

<210> SEQ ID NO 26
<211> LENGTH: 1063
<212> TYPE: DNA
<213> ORGANISM: Staphylococcus aureus

<400> SEQUENCE: 26
atgaaaatca ccattttagc tgtagggaaa ctaaaagaga aatattggaa gcaagccata      60
gcagaatatg aaaaacgttt aggcccatac accaagatag acatcataga agttccagac     120
gaaaaagcac cagaaaatat gagcgacaaa gaaattgagc aagtaaaaga aaagaaggc      180 caacgaatac tagccaaaat caaaccacaa tcaacagtca ttacattaga aatacaagga     240
aagatgctat cttccgaagg attggcccaa gaattgaacc aacgcatgac ccaagggcaa     300
agcgactttg tattcgtcat tggcggatca aacggcctgc acaaggacgt cttacaacgc     360
agtaactacg cactatcatt cagcaaaatg acattcccac atcaaatgat gcgggttgtg     420
ttaattgaac aagtgtacag agcatttaag attatgcgtg gagaagcata tcataagtga     480
tgcggttttt attaattagt tgctaaaaaa tgaagtatgc aatattaatt attattaaat     540
tttgatatat ttaaagaaag attaagttta gggtgaatga atggcttatc aaagtgaata     600
tgcattagaa aatgaagtac ttcaacaact tgaggaattg aactatgaaa gagtaaatat     660
acataatatt aaattagaaa ttaatgaata tctcaaagaa ctaggagtgt tgaaaaatga     720
ataagcagac aaatactcca gaactaagat ttccagagtt tgatgaggaa tggaaaaaaa     780
ggaaattagg tgaagtagta aattataaaa atggtggttc atttgaaagt ttagtgaaaa     840
accatggtgt atataaactc ataactctta aatctgttaa tacagaagga aagttgtgta     900
attctggaaa atatatcgat gataaatgtg ttgaaacatt gtgtaatgat actttagtaa     960
tgatactgag cgagcaagca ccaggactag ttggaatgac tgcaattata cctaataata    1020
atgagtatgt actaaatcaa cgagtagcag cactagtgcc taa                      1063

<210> SEQ ID NO 27
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 27
ttcttaagta cacgctgaat cg                                              22

<210> SEQ ID NO 28
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 28
taatttcctt ttttccatt cctc                                             24

<210> SEQ ID NO 29
<211> LENGTH: 24
<212> TYPE: DNA
<213> ORGANISM: Artificial Sequence
<220> FEATURE:
```

<223> OTHER INFORMATION: Synthetically prepared nucleic acid sequence

<400> SEQUENCE: 29
tgataagcca ttcattcacc ctaa                                          24

<210> SEQ ID NO 30
<211> LENGTH: 19
<212> TYPE: DNA
<213> ORGANISM: Artificial Sequence
<220> FEATURE:
<223> OTHER INFORMATION: Synthetically prepared nucleic acid sequence

<400> SEQUENCE: 30
ggatcaaacg gcctgcaca                                                19

<210> SEQ ID NO 31
<211> LENGTH: 37
<212> TYPE: DNA
<213> ORGANISM: Artificial Sequence
<220> FEATURE:
<223> OTHER INFORMATION: Synthetically prepared nucleic acid sequence

<400> SEQUENCE: 31
cccgcgcgta gttactgcgt tgtaagacgt ccgcggg                            37

<210> SEQ ID NO 32
<211> LENGTH: 37
<212> TYPE: DNA
<213> ORGANISM: Artificial Sequence
<220> FEATURE:
<223> OTHER INFORMATION: Synthetically prepared nucleic acid sequence

<400> SEQUENCE: 32
cccgcgcata gttactgcgt tgtaagacgt ccgcggg                            37

<210> SEQ ID NO 33
<211> LENGTH: 37
<212> TYPE: DNA
<213> ORGANISM: Artificial Sequence
<220> FEATURE:
<223> OTHER INFORMATION: Synthetically prepared nucleic acid sequence

<400> SEQUENCE: 33
cccgcgcgta gttactacgt tgtaagacgt ccgcggg                            37

<210> SEQ ID NO 34
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 34
caaattgtag cattcttgaa ctat                                          24

<210> SEQ ID NO 35
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 35
ctcccatttc ttccaaaaaa tata                                          24

<210> SEQ ID NO 36
<211> LENGTH: 29
<212> TYPE: DNA
<213> ORGANISM: Artificial Sequence
<220> FEATURE:
<223> OTHER INFORMATION: Synthetically prepared nucleic acid sequence

<400> SEQUENCE: 36
gtcaaaaatc atgaacctca ttacttatg                              29

<210> SEQ ID NO 37
<211> LENGTH: 1256
<212> TYPE: DNA
<213> ORGANISM: Staphylococcus aureus

<400> SEQUENCE: 37
gctgtaggga aactaaaaga gaaatattgg aagcaagcca tagcagaata tgaaaaacgt    60
ttaggcccat acaccaagat agacatcata gaagttccag acgaaaaagc accagaaaat   120
atgagcgaca aagaaattga gcaagtaaaa gaaaagaag gccaacgaat actagccaaa    180
attaaaccac aatccacagt cattacatta gaaatacaag gaaagatgct atcttccgaa   240
ggattggccc aagaattgaa ccaacgcatg acccaagggc aaagcgactt tgtattcgtc   300
attggcggat caaacggcct gcacaaggac gtcttacaac gcagtaacta cgcactatca   360
ttcagcaaaa tgacattccc acatcaaatg atgcgggttg tgttaattga gcaagtgtat   420
agagcattta gattatgcg tggagaagca tatcataaat gatgcggttt tttcagccgc    480
ttcataaagg gattttgaat gtatcagaac atatgaggtt tatgtgaatt gctgttatgt   540
ttttaagaag catatcataa gtgatgcggt ttttattaat tagttgctaa aaaatgaagt   600
atgcaatatt aattattatt aaattttgat atatttaaag aaagattaag tttagggtga   660
atgaatggct tatcaaagtg aatatgcatt agaaaatgaa gtacttcaac aacttgagga   720
attgaactat gaaagagtaa atatacataa tattaaatta gaaattaatg aatatctcaa   780
agaactagga gtgttgaaaa atgaataagc agacaaatac tccagaacta agatttccag   840
agtttgatga ggaatggaaa aaaaggaaat taggtgaagt agtaaattat aaaaatggtg   900
gttcatttga agtttagtg aaaaaccatg gtgtatataa actcataact cttaaatctg    960
ttaatacaga aggaaagttg tgtaattctg gaaatatat cgatgataaa tgtgttgaaa   1020
cattgtgtaa tgatacttta gtaatgatac tgagcgagca agcaccagga ctagttggaa   1080
tgactgcaat tatacctaat aataatgagt atgtactaaa tcaacgagta gcagcactag   1140
tgcctaaaca atttatagat agtcaatttc tatctaagtt aattaataga aaccagaaat   1200
atttcagtgt gagatctgct ggaacaaaag tgaaaaatat ttctaaagga catgta       1256

<210> SEQ ID NO 38
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 38
gaggaccaaa cgacatgaaa atc                                    23

<210> SEQ ID NO 39
<211> LENGTH: 756
<212> TYPE: DNA
<213> ORGANISM: Staphylococcus aureus

<400> SEQUENCE: 39

```
tgacattccc acatcaaatg atgcgggttg tgttaattga gcaagtgtat agagcattta        60
agattatgcg tggagaagcg tatcacaaat aaaactaaaa aataggttgc gcataatata       120
attagaaagg aattagacat aaattaggag tccttcacag aatagcgaag gactcccatt       180
aaatatatta tggtgtaaag aaatcacaaa tcaatatata tacttaatac catatattaa       240
cttgtactat tataaagtac gacatcagta ttaggtatca ctttgaacac atgaatttca       300
ttatcacttt tattattcac aaaaaatttt ccaattctca attactgaat tatgtgtata       360
catgttgtta aaaattaata aaggatattt atgtttgttt aaagcatatc acaagtgatg       420
cggttttta taaagattta cttgttagtg attttgataa aaatgcttaa tactatttca       480
ataatatgta tttaaaaatt agattaatag tatttaactt caaatggcct cgtataaact       540
catagcaaat taacgtaaat caatgaaata aaatgaaaac aatttcaaga atacattata       600
aacataaagt atacaaaaaa taatgagcg tatttgttta aacgtataca ctcattttta        660
ttaaattaat ttattatatt ttacgattgt tatttatgaa attaacaaat tccattttg        720
atagtgaaat taaaagcttt atcacttatt attgat                                 756
```

<210> SEQ ID NO 40
<211> LENGTH: 771
<212> TYPE: DNA
<213> ORGANISM: Staphylococcus aureus

<400> SEQUENCE: 40

```
tgacattccc acatcaaatg atgcgggttg tgttaattga gcaagtgtat agagcattta        60
agattatgcg tggagaagcg tatcacaaat aaaactaaaa aataggttgc gcataatata       120
attagaaagg aattagacat aaattaggag tccttcacag aatagcgaag gactcccatt       180
aaatatatta tggtgtaaag aaatcacaaa tcaatatata tacttaatac catatattaa       240
cttgtactat tataaagtac gacatcagta ttaggtatca ctttgaacac atgaatttca       300
ttatcacttt tattattcac aaaaaatttt ccaattctca attactgaat tatgtgtata       360
catgttgtta aaaattaata aaggatattt atgtttgttt aaagcatatc acaagtgatg       420
cggttttta taaagattta cttgttagtg attttgataa aaatgcttaa tactatttca       480
ataatatgta tttaaaaatt agattaatag tatttaactt caaatggcct cgtataaact       540
catagcaaat taacgtaaat caatgaaata aaatgaaaac aatttcaaga atacattata       600
aacataaagt atacaaaaaa taatgagcg tatttgttta aacgtataca ctcattttta        660
ttaaattaat ttattatatt ttacgattgt tatttatgaa attaacaaat tccattttg        720
atagtgaaat taaaagcttt atcacttatt attgataatt tgactgcat c                 771
```

<210> SEQ ID NO 41
<211> LENGTH: 681
<212> TYPE: DNA
<213> ORGANISM: Staphylococcus aureus

<400> SEQUENCE: 41

```
ttcagcaaaa tgacattccc acatcaaatg atgcgggttg tgttaattga acaagtgtac        60
agagcattta agattatgcg tggagaagcg tatcataagt agcggaggag tttttttacct      120
tgtgacttat cataaagtac gatgtttatg taagtgatta tcattattta agcaggtttt       180
tcaaattaaa taataacaag aataaaatgc acttagcgac attgaaattt attaatctag       240
taaactaata gatttataga aaattttatt tgcaagggga taatttgaa aagtagtatt        300
```

```
ttctatcttt ccataataca ttgtaattac aacggagggg atattgtgat gaagtgtata    360
gataaaacgt gggttagcta ttataaagaa ttagctgata agttaacaga ttatcaaaat    420
aaacgttatg aattaattag aaatagtgaa ggaagtatat aaaaaaacgg aataaaatt     480 ccctacttta gcaagtgata atgtattgat ggacatagat ccttttacaa tatttgcatt    540
atttaataaa aattccatga gagaaactaa taaggtaaaa atattaacag aattagcttc    600
ggaattgaat attaagtcca aaattccgtc agttttttgac agtattccaa cagtcaataa   660
tctgaatgct acatattata a                                              681

<210> SEQ ID NO 42
<211> LENGTH: 1119
<212> TYPE: DNA
<213> ORGANISM: Staphylococcus aureus

<400> SEQUENCE: 42
gacattccca catcaaatga tgcgggttgt gttaattgag caagtgtata gagcatttaa     60
gattatgcgt ggagaggcgt atcataagta aaactaaaaa attctgtatg aggagataat    120
aatttggagg gtgttaaatg gtggacatta aatccacgtt cattcaatat ataagatata    180
tcacgataat tgcgcatata acttaagtag tagctaacag ttgaaattag gccctatcaa    240
attggtttat atctaaaatg attaatatag aatgcttctt tttgtcctta ttaaattata    300
aaagtaactt tgcaatagaa acagttattt cataatcaac agtcattgac gtagctaagt    360
aatgataaat aatcataaat aaaattacag atattgacaa aaaatagtaa atataccaat    420
gaagtttcaa agaacaatt ccaagaaatt gagaatgtaa ataataaggt caaagaattt     480
tattaagatt tgaaagagta tcaatcaaga agatgtagt ttttttaataa actatttgga    540 aaataattat caatttaa aaactgacaa tttgcgagac tcataaaatg taataatgga     600
aatagatgta aaatataatt aagggtgta atatgaagat taatatttat aaatctattt    660
ataattttca ggaaacaaat acaaattttt tagagaatct agaatcttta aatgatgaca    720
attatgaact gcttaatgat aaagaacttg ttagtgattc aaatgaatta aaattaatta    780
gtaaagttta tacgtaaaa aaagacaaaa aactattaga ttggcaatta ttaataaaga    840 atgtataccct agatactgaa gaagatgaca atttattttc agaatccggt catcattttg   900
atgcaatatt atttctcaaa gaagatacta cattacaaaa taatgtatat attataccctt  960 ttggacaagc atatcatgat ataaataatt tgattgatta tgacttcgga attgattttg   1020
cagaaagagc aatcaaaaat gaagacatag ttaataaaaa tgttaatttt tttcaacaaa   1080
acaggcttaa agagattgtt aattatagaa ggaatagtg                          1119

<210> SEQ ID NO 43
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 43
cattttgctg aatgatagtg cgta                                            24

<210> SEQ ID NO 44
<211> LENGTH: 23
<212> TYPE: DNA
<213> ORGANISM: Artificial Sequence
<220> FEATURE:
```

-continued

<210> SEQ ID NO 44
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 44
gaggaccaaa cgacatgaaa atc                                          23

<210> SEQ ID NO 45
<211> LENGTH: 21
<212> TYPE: DNA
<213> ORGANISM: Artificial Sequence
<220> FEATURE:
<223> OTHER INFORMATION: Synthetically prepared nucleic acid sequence

<400> SEQUENCE: 45
atcaaatgat gcgggttgtg t                                            21

<210> SEQ ID NO 46
<211> LENGTH: 26
<212> TYPE: DNA
<213> ORGANISM: Artificial Sequence
<220> FEATURE:
<223> OTHER INFORMATION: Synthetically prepared nucleic acid sequence

<400> SEQUENCE: 46
aaacgaaaat actggtgaag atatta                                       26

<210> SEQ ID NO 47
<211> LENGTH: 25
<212> TYPE: DNA
<213> ORGANISM: Artificial Sequence
<220> FEATURE:
<223> OTHER INFORMATION: Synthetically prepared nucleic acid sequence

<400> SEQUENCE: 47
ttgcctttct caagtcttta caact                                        25

<210> SEQ ID NO 48
<211> LENGTH: 20
<212> TYPE: DNA
<213> ORGANISM: Artificial Sequence
<220> FEATURE:
<223> OTHER INFORMATION: Synthetically prepared nucleic acid sequence

<400> SEQUENCE: 48
cgaggagaag cgtatcacaa                                              20

<210> SEQ ID NO 49
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 49
agttgccata gattcaattt ctaaggt                                      27

<210> SEQ ID NO 50
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 50
aacaggtgaa ttattagcac ttgtaag                                      27

```
<210> SEQ ID NO 51
<211> LENGTH: 26
<212> TYPE: DNA
<213> ORGANISM: Artificial Sequence
<220> FEATURE:
<223> OTHER INFORMATION: Synthetically prepared nucleic acid sequence

<400> SEQUENCE: 51
ctattgttcc acaaattatg attact                                            26

<210> SEQ ID NO 52
<211> LENGTH: 26
<212> TYPE: DNA
<213> ORGANISM: Artificial Sequence
<220> FEATURE:
<223> OTHER INFORMATION: Synthetically prepared nucleic acid sequence

<400> SEQUENCE: 52
cttcttttct tgttattctt tcttct                                            26

<210> SEQ ID NO 53
<211> LENGTH: 20
<212> TYPE: DNA
<213> ORGANISM: Artificial Sequence
<220> FEATURE:
<223> OTHER INFORMATION: Synthetically prepared nucleic acid sequence

<400> SEQUENCE: 53
ctaaatcata gccatgaccg                                                   20

<210> SEQ ID NO 54
<211> LENGTH: 20
<212> TYPE: DNA
<213> ORGANISM: Artificial Sequence
<220> FEATURE:
<223> OTHER INFORMATION: Synthetically prepared nucleic acid sequence

<400> SEQUENCE: 54
atgctctttg ttttgcagca                                                   20

<210> SEQ ID NO 55
<211> LENGTH: 1073
<212> TYPE: DNA
<213> ORGANISM: Staphylococcus aureus

<400> SEQUENCE: 55
tattggaagc aagccatagc agaatatgaa aaacgtttag gcccatacac caagatagac       60
atcatagaag ttccagacga aaaagcacca gaaaatatga gcgacaaaga aattgagcaa      120
gtaaaagaaa aagaaggcca acgaatacta gccaaaatca accacaatc cacagtcatt       180 acattagaaa tacaaggaaa gatgctatct tccgaaggat gcccaaga attgaaccaa        240 cgcatgaccc aagggcaaag cgactttgta ttcgtcattg gcggatcaaa cggcctgcac      300
aaggacgtct acaacgcag taactatgca ctatcattta gcaaaatgac attcccacat      360
caaatgatgc gggttgtgtt aattgaacaa gtgtatagag catttaagat tatgcgtgga     420
gaggcgtatc ataagtgatg cttgttagaa tgattttta caatatgaaa tagctgtgga    480
agcttaaaca atttgtttat ctaagtactt atttaataat tgattgaact gtgattggca     540
ccaggctgtc tggtaaattg agaagttggg ttttggagcg tataaatgat agaattaata     600
taaaattcaa tttgaggagt aggagattat gtcgaatata aaacaacac tagagacgtc      660 cgtaggacta gaaaaagaca acgataagct atttgattat ataactgaat tagagattca     720
```

```
aaacacgcct gaaaaccggg aagcaaaagt tgttattgaa gaaaggttac ataaagaata    780
taaatatgaa ttagatcaaa tgacaccaga gtatggaata caaaaaggca gtgttagaat    840
aggtcatgca gatgttgtaa tatttcatga ttctaaagat aaatctcaag agaatattaa    900
aataatagta gagtgtaaaa gaaagaatcg cagggatggt attgaacaat taaaaacata    960
tcttgcaggg tgtgagtctg cagaatacgg cgtttggttt aatggagaag atatagtata   1020
tataaaacga ttgaaaaaag caccacattg gaaaacagta tttaatatac cga          1073

<210> SEQ ID NO 56
<211> LENGTH: 595
<212> TYPE: DNA
<213> ORGANISM: Staphylococcus aureus

<400> SEQUENCE: 56
atgaaaatca ccattttagc tgtagggaaa ctaaaagaga atattggaa gcaagccata     60 gcagaatatg aaaaacgttt aggcccatac accaagatag acatcataga agttccagac   120
gaaaaagcac cagaaaatat gagtgacaaa gaaattgagc aagtaaaaga aaagaaggc    180 caacgaatac tagccaaaat caaaccacaa tccacagtca ttacattaga aatacaagga   240
aagatgctat cttccgaagg attggcccaa gaattgaacc aacgcatgac ccaagggcaa   300
agcgactttg ttttcgtcat tggcggatca aacggcctgc acaaggacgt cttacaacgc   360
agtaactacg cactatcatt cagcaaaatg acattccac atcaaatgat gcgggttgtg   420
ttaattgaac aagtgtacag agcatttaag attatgcgag gagaagcgta tcacaaataa   480
aactaaaaaa tagattgtgt ataatataaa aggagcggat ttatattaaa actttgaatt   540
caaaaattat tgaagggaa gctaccttag aaattgaatc tatggcaact aatac         595

<210> SEQ ID NO 57
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 57
cgtggagagg cgtatcataa gt                                              22

<210> SEQ ID NO 58
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 58
gctccaaaac ccaacttctc aa                                              22

<210> SEQ ID NO 59
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 59
gccaaaatta aaccacaatc cac                                             23

<210> SEQ ID NO 60
<211> LENGTH: 30
```

<210> SEQ ID NO 60 (implicit continuation)
<212> TYPE: DNA
<213> ORGANISM: Artificial Sequence
<220> FEATURE:
<223> OTHER INFORMATION: Synthetically prepared nucleic acid sequence

<400> SEQUENCE: 60
aatctttgtc ggtacacgat attcttcacg         30

<210> SEQ ID NO 61
<211> LENGTH: 30
<212> TYPE: DNA
<213> ORGANISM: Artificial Sequence
<220> FEATURE:
<223> OTHER INFORMATION: Synthetically prepared nucleic acid sequence

<400> SEQUENCE: 61
cgtaatgaga tttcagtaga taatacaaca         30

<210> SEQ ID NO 62
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 62
gccaaaatca aaccacaatc cac         23

<210> SEQ ID NO 63
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 63
attgctgtta atatttttg agttgaa         27

<210> SEQ ID NO 64
<211> LENGTH: 21
<212> TYPE: DNA
<213> ORGANISM: Artificial Sequence
<220> FEATURE:
<223> OTHER INFORMATION: Synthetically prepared nucleic acid sequence

<400> SEQUENCE: 64
tattgcaggt ttcgatgttg a         21

<210> SEQ ID NO 65
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 65
tcaccgtctt tcttttgacc tt         22

<210> SEQ ID NO 66
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 66
cagcaattcw cataaacctc ata                              23

<210> SEQ ID NO 67
<211> LENGTH: 26
<212> TYPE: DNA
<213> ORGANISM: Artificial Sequence
<220> FEATURE:
<223> OTHER INFORMATION: Synthetically prepared nucleic acid sequence

<400> SEQUENCE: 67
caggcatagc tatatatgat aaagca                           26

<210> SEQ ID NO 68
<211> LENGTH: 26
<212> TYPE: DNA
<213> ORGANISM: Artificial Sequence
<220> FEATURE:
<223> OTHER INFORMATION: Synthetically prepared nucleic acid sequence

<400> SEQUENCE: 68
atgcctttaa atcattcaca ttgaca                           26

<210> SEQ ID NO 69
<211> LENGTH: 2150
<212> TYPE: DNA
<213> ORGANISM: Staphylococcus aureus

<400> SEQUENCE: 69
tgaatcgttt aacgtgtcac atgatgcgat agatccgcaa ttttatattt tccataataa      60
ctataagaag tttacgattt taacagatac gggttacgtg tctgatcgta tgaaaggtat     120
gatacgtggc agcgatgcat ttattttga gagtaatcat gacgtcgata tgttgagaat     180
gtgtcgttat ccatggaaga cgaaacaacg cattttaggc gatatgggtc atgtatctaa     240
tgaggatgcg ggtcatgcga tgacagacgt gattacaggg aacacgaaac gtatttactt     300
atcgcattta tcacaagata taatatgaa agatttggcg cgtatgagtg ttggccaagt     360
attgaacgaa cacgatattg atacggaaaa agaagtattg ctatgtgata cggataaagc     420
tattccaaca ccaatatata caatataaat gagagtcatc cgataaagtt ccgcactgct     480
gtgaaacgac tttatcgggt gcttttttat gttgttggtg ggaaatggct gttgttgagt     540
tgaatcggat tgattgaaat gtgtaaaata attcgatatt aaatgtaatt tataaataat     600
ttacataaaa tcaaacattt taatataagg attatgataa tatattggtg tatgacagtt     660
aatggaggga acgaaatgaa agctttatta cttaaaacaa gtgtatggct cgttttgctt     720
tttagtgtga tgggattatg gcatgtctcg aacgcggctg agcagcatac accaatgaaa     780
gcacaagcag caacaacaga taagcaacaa gtaacgccaa caaggaagc ggctcatcaa     840
tctggtgaag aagcggcaac caacgtatca gcatcagtac agggaacagc tgatgataca     900
aacaacaaag taacatccaa cgcaccatct aacaaaccat ctacagcagt tcaacaaca     960
gtaaacgaaa cgcgcgacgt agatgcacaa caagcctcaa cacaaaaacc aactcaatca    1020
gcaacattca aattatcaaa tgctaaaaca gcatcacttt caccacgaat gtttgctgct    1080
aatgcaccac aaacaacaac acataaaata tggttctgtt gcaaagtaaa aaaatatagc    1140
taaccactaa tttatcatgt cagtgttcgc ttaacttgct agcatgatgc taatttcgtg    1200
gcatggcgaa aatccgtaga tctgaagaga cctgcggttc tttttatata gagcgtaaat    1260
acattcaata cctttaaaag tattcttttgc tgtattgata ctttgatacc ttgtcttttct    1320
tactttaata tgacggtgat cttgctcaat gaggttattc agatatttcg atgtacaatg    1380

```
acagtcaggt ttaagtttaa aagctttaat tactttagcc attgctacct tcgttgaagg    1440
tgcctgatct gtaattacct tttgaggttt accaaattgt ttaatgagac gtttgataaa    1500
cgcatatgct gaatgattat ctcgttgctt acgcaaccaa atatctaatg tatgtccctc    1560
tgcatcaatg gcacgatata aatagctcca ttttccttttt attttgatgt acgtctcatc    1620
aatacgccat tgtaataag ctttttatg cttttcttc caaatttgat acaaaattgg        1680
ggcatattct tgaacccaac ggtagaccgt tgaatgatga acgtttacac cacgttccct    1740
taatatttca gatatatcac gataactcaa tgtatatctt agatagtagc caacggctac    1800
agtgataaca tccttgttaa attgtttata tctgaaatag ttcatacaga agactccttt    1860
ttgttaaaat tatactataa attcaacttt gcaacagaac cgaaaaacta gacttgatta    1920
caaaatggag cttgggacat aaatgatttt ttaaaaatga gatgagacgt agattaactc    1980
cataatcaat acgaatctat cgacttcttt atttatgata ttcatctctt tttaatggaa    2040
ataaaagtgc gattaatgtg ataatacagt tacgttaatt aaaaaaataa aaatgcaagg    2100
agaggtaata tgctaactgt atatggacat agaggattac ctagtaaagc                2150
```

<210> SEQ ID NO 70
<211> LENGTH: 29
<212> TYPE: DNA
<213> ORGANISM: Artificial Sequence
<220> FEATURE:
<223> OTHER INFORMATION: Synthetically prepared nucleic acid sequence

<400> SEQUENCE: 70
atttcatata tgtaattcct ccacatctc                                        29

<210> SEQ ID NO 71
<211> LENGTH: 29
<212> TYPE: DNA
<213> ORGANISM: Artificial Sequence
<220> FEATURE:
<223> OTHER INFORMATION: Synthetically prepared nucleic acid sequence

<400> SEQUENCE: 71
caaatattat ctcgtaattt accttgttc                                        29

<210> SEQ ID NO 72
<211> LENGTH: 29
<212> TYPE: DNA
<213> ORGANISM: Artificial Sequence
<220> FEATURE:
<223> OTHER INFORMATION: Synthetically prepared nucleic acid sequence

<400> SEQUENCE: 72
ctctgcttta tattataaaa ttacggctg                                        29

<210> SEQ ID NO 73
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 73
caagctccat tttgtaatca ag                                               22

<210> SEQ ID NO 74
<211> LENGTH: 27
<212> TYPE: DNA

-continued

```
<213> ORGANISM: Artificial Sequence
<220> FEATURE:
<223> OTHER INFORMATION: Synthetically prepared nucleic acid sequence

<400> SEQUENCE: 74
cactttttat tcttcaaaga tttgagc                                          27

<210> SEQ ID NO 75
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 75
acaaactttg aggggatttt tagtaaa                                          27

<210> SEQ ID NO 76
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 76
gccaaaatca aaccacaatc aac                                              23

<210> SEQ ID NO 77
<211> LENGTH: 3050
<212> TYPE: DNA
<213> ORGANISM: Staphylococcus aureus

<400> SEQUENCE: 77
tcgtgccatt gatgcagagg gacatacatt agatatttgg ttgcgtaagc aacgagataa        60
tcattcagca tatgcgttta tcaaacgtct cattaaacaa tttggtaaac ctcaaaaggt       120
aattacagat caggcacctt caacgaaggt agcaatggct aaagtaatta aagcttttaa       180
acttaaacct gactgtcatt gtacatcgaa atatctgaat aacctcattg agcaagatca       240
ccgtcatatt aaagtaagaa agacaaggta tcaaagtatc aatacagcaa agaatacttt       300
aaaaggtatt gaatgtattt acgctctata taaaaagaac cgcaggtctc ttcagatcta       360
cggattttcg ccatgccacg aaattagcat catgctagca agttaagcga acactgacat       420
gataaattag tggttagcta tattttttta ctttgcaaca gaaccgaaaa taatctcttc       480
aatttatttt tatatgaatc ctgtgactca atgattgtaa tatctaaaga tttcagttca       540
tcatagacaa tgttcttttc aacatttttt atagcaaatt gattaaataa attctctaat       600
ttctcccgtt tgatttcact accatagatt atattatcat tgatatagtc aatgaataat       660
gacaaattat cactcataac agtcccaacc cctttatttt gatagactaa ttatcttcat       720
cattgtaaaa caaattacac cctttaaatt taactcaact taaatatcga caaattaaaa       780
aacaataaaa ttacttgaat attattcata atatattaac aactttatta tactgctctt       840
tatatataaa atcattaata attaaacaag ccttaaaata tttaactttt ttgtgattat       900
tacacattat cttatctgct ctttatcacc ataaaaatag aaaaaacaag attcctaaag       960
aatataggaa tcttgtttca gactgtggac aaactgattt tttatcagtt agcttattta      1020
gaaagtttta tttaaattac agtttctatt tttattagat cacaatttta ttttagctct      1080
tgttcaagta atcattttc gccaaaaact ttatactgaa tagcttctac attaaatact      1140
ttgtcaatga gatcatctac atctttaaat tcagaataat ttgcatatgg atctataaaa      1200
```

-continued

```
taaaattgtg gttctttacc ggaaacatta aatattctta atattaaata tttctgctta    1260
tattctttca tagcaaacat ttcatttagc gacataaaaa atggttcctc aatactagaa    1320
gatgtagatg ttttaatttc aataaatttt tctacagctt tatctgtatt tgttggatca    1380
aaagctacta atcatagcc atgaccgtgt tgagagcctg gattatcatt taaaatattc    1440
ctaaactgtt ctttcttatc ttcgtctatt ttattatcaa ttagctcatt aaagtaattt    1500
agcgctaatt tttctccaac tttaccggtt aatttattct ctttatttga ttttcaatt    1560 tctgaatcat ttttagtagt ctttgataca cctttttat attttggaat tattcctta     1620 ggtgcttcca cttccttgag tgtcttatct ttttgtgctg ttctaatttc ttcaatttcg    1680
ctgtcttcct gtatttcgtc tatgctattg accaagctat cataggatgt ttttgtaact    1740
tttgaagcta attcattaaa tagttctaaa aatttcttta aatcctctag catatcttct    1800
tctgtgaatc cttcattcaa atcataatat ttgaatctta ttgatccatg agaatatcct    1860
gatggataat cattttttaa atcataagat gaatctttat tttctgcgta ataaaatctt    1920
ccagtattaa attcatttga tgtaatatat ttattgagtt cggaagataa agttaatgct    1980
ctttgttttg cagcattttt atcccgcgga aacatatcac ttatctttga ccatccttga    2040
ttcaaagata agtatatgcc ttctccttcc ggatgaaaaa gatataccaa ataatatcca    2100
tcctttgttt cttttgttat attctcatca tatattgaaa tccaaggaac tttactatag    2160
ttcccagtag caaccttccc tacaactgaa tatttatctt cttttatatg cacttttaac    2220
tgcttgggta acttatcatg gactaaagtt ttatatagat cacctttatc ccaatcagat    2280
tttttaacta cattattggt acgtttctct ttaattaatt taaggacctg cataaagttg    2340
tctatcattt gaaattccct cctattataa aatatattat gtctcatttt ttcaatatg    2400 tacttattta tattttaccg taatttacta tatttagttg cagaaagaat tttctcaaag    2460
ctagaacttt gcttcactat aagtattcag tataaagaat atttcgctat tatttacttg    2520
aaatgaaaga ctgcggaggc taactatgtc aaaaatcatg aacctcatta cttatgataa    2580
gcttctcctc gcataatctt aaatgctctg tacacttgtt caattaacac aacccgcatc    2640
atttgatgtg ggaatgtcat tttgctgaat gatagtgcgt agttactgcg ttgtaagacg    2700
tccttgtgca ggccgtttga tccgccaatg acgaaaacaa agtcgctttg cccttgggtc    2760
atgcgttggt tcaattcttg ggccaatcct tcggaagata gcatctttcc ttgtatttct    2820
aatgtaatga ctgtggattg tggtttgatt ttggctagta ttcgttggcc ttcttttct     2880 tttacttgct caatttcttt gtcactcata ttttctggtg cttttttcgtc tggaacttct    2940 atgatgtcta tcttggtgta tgggcctaaa cgttttttcat attctgctat ggcttgcttc    3000
caatatttct cttttagttt ccctacagct aaaatggtga ttttcatgtc                3050
```

<210> SEQ ID NO 78
<211> LENGTH: 3050
<212> TYPE: DNA
<213> ORGANISM: Staphylococcus aureus

<400> SEQUENCE: 78

```
acctcattga gcaagatcac cgtcatatta aagtaagaaa gacaaggtat caaagtatca      60
atacagcaaa gaatacttta aaaggtattg aatgtatttta cgctctatat aaaaagaacc    120
gcaggtctct tcagatctac ggattttcgc catgccacga aattagcatc atgctagcaa    180
gttaagcgaa cactgacatg ataaattagt ggttagctat attttttac tttgcaacag      240
```

```
aaccgaaaat aatctcttca atttattttt atatgaatcc tgtgactcaa tgattgtaat    300
atctaaagat ttcagttcat catagacaat gttcttttca acatttttta tagcaaattg    360
attaaataaa ttctctaatt tctcccgttt gatttcacta ccatagatta tattatcatt    420
gatatagtca atgaataatg acaaattatc actcataaca gtcccaaccc ctttcttttg    480
atagactaat tatcttcatc attgtaaaac aaattcacc ctttaaattt aactcaactt    540
aaatatcgac aaattaaaaa acaataaaat tacttgaata ttattcataa tatattaaca    600
actttattat actgctcttt atatataaaa tcattaataa ttaaacaagc cttaaaatat    660 ttaactttt tgtgattatt acacattatc ttatctgctc tttatcacca taaaaataga    720
aaaaacaaga ttcctaaaga ataggaat cttgtttcag actgtggaca aactgattt    780 ttatcagtta gcttatttag aaagttttat ttaaattaca gtttctattt ttattagatc    840
acaattttat tttagctctt gttcaagtaa tcatttttcg ccaaaaactt tatactgaat    900
agcttctaca ttaaatactt tgtcaatgag atcatctaca tctttaaatt cagataatt    960 tgcatatgga tctataaaat aaaattgtgg ttctttaccg gaaacattaa atattcttaa   1020
tattaaatat ttctgcttat attctttcat agcaaacatt tcatttagcg acataaaaaa   1080
tggttcctca atactagaag atgtagatgt tttaatttca ataaattttt ctacagcttt   1140
atctgtattt gttggatcaa aagctactaa atcatagcca tgaccgtgtt gagagcctgg   1200
attatcattt aaaatattcc taaactgttc tttcttatct tcgtctattt tattatcaat   1260
tagctcatta aagtaattta gcgctaattt ttctccaact ttaccggtta atttattctc   1320
tttatttgat ttttcaattt ctgaatcatt tttagtagtc tttgatacac ctttttata   1380 ttttggaatt attcctttag gtgcttccac ttccttgagt gtcttatctt tttgtgctgt   1440
tctaatttct tcaatttcgc tgtcttcctg tatttcgtct atgctattga ccaagctatc   1500
ataggatgtt tttgtaactt ttgaagctaa ttcattaaat agttctaaaa atttctttaa   1560
atcctctagc atatcttctt ctgtgaatcc ttcattcaaa tcataatatt tgaatcttat   1620
tgatccatga gaatatcctg atggataatc attttttaaa tcataagatg aatctttatt   1680
ttctgcgtaa taaaatcttc cagtattaaa ttcatttgat gtaatatatt tattgagttc   1740
ggaagataaa gttaatgctc tttgttttgc agcattttta tcccgcggaa acatatcact   1800
tatctttgac catccttgat tcaaagataa gtatatgcct tctccttccg gatgaaaaag   1860
atataccaaa taatatccat cctttgtttc ttttgttata ttctcatcat atattgaaat   1920
ccaaggaact ttactatagt tcccagtagc aaccttccct acaactgaat atttatcttc   1980
ttttatatgc acttttaact gcttgggtaa cttatcatgg actaaagttt tatatagatc   2040
acctttatcc caatcagatt ttttaactac attattggta cgtttctctt taattaattt   2100
aaggacctgc ataagttgt ctatcatttg aaattccctc ctattataaa atatattatg   2160
tctcattttc ttcaatatgt acttatttat attttaccgt aatttactat atttagttgc   2220
agaaagaatt ttctcaaagc tagaactttg cttcactata agtattcagt ataaagaata   2280
tttcgctatt atttacttga aatgaaagac tgcggaggct aactatgtca aaaatcatga   2340
acctcattac ttatgataag cttcttaaaa acataacagc aattcacata aacctcatat   2400
gttctgatac attcaaaatc cctttatgaa gcggctgaaa aaaccgcatc atttatgata   2460
tgcttctcca cgcataatct taaatgctct atacacttgc tcaattaaca caacccgcat   2520
catttgatgt gggaatgtca ttttgctgaa tgatagtgcg tagttactgc gttgtaagac   2580
gtccttgtgc aggccgtttg atccgccaat gacgaataca aagtcgcttt gcccttgggt   2640
```

| | |
|---|---|
| catgcgttgg ttcaattctt gggccaatcc ttcggaagat agcatctttc cttgtatttc | 2700 |
| taatgtaatg actgtggatt gtggtttaat tttggctagt attcgttggc cttcttttc | 2760 |
| ttttacttgc tcaatttctt tgtcgctcat attttctggt gcttttcgt ctggaacttc | 2820 |
| tatgatgtct atcttggtgt atgggcctaa acgtttttca tattctgcta tggcttgctt | 2880 |
| ccaatatttc tcttttagtt tccctacagc taaaatggtg attttcatgt cgtttggtcc | 2940 |
| tccaaattgt tatcaacttt ccagttatcc acaagttatt aacttgttca cactgttccc | 3000 |
| tcttattata ccaatatttt ttgcagtttt tgatattttc ctgacattta | 3050 |

<210> SEQ ID NO 79
<211> LENGTH: 385
<212> TYPE: DNA
<213> ORGANISM: Staphylococcus aureus

<400> SEQUENCE: 79

| | |
|---|---|
| ttcgtcattg gcggatcaaa cggcctgcac aaggacgtct tacaacgcag taactacgcg | 60 |
| ctatcattca gcaaaatgac attcccacat caaatgatgc gggttgtgtt aattgaacaa | 120 |
| gtgtacaaag catttaagat tatgcgagga gaagcttatc ataagtaatg aggttcatga | 180 |
| ttttttgacat agttagcctc cgcagtcttt catttcaagt aaataatagc gaaatattct | 240 |
| ttatactgaa tacttatagt gaagcaaagt tctagctttg agaaaattct ttctgcaact | 300 |
| aaatatagta aattacggta aaatataaat aagtacatat tgaagaaaat gagacataat | 360 |
| atattttata ataggaggga atttc | 385 |

<210> SEQ ID NO 80
<211> LENGTH: 2153
<212> TYPE: DNA
<213> ORGANISM: Staphylococcus aureus

<400> SEQUENCE: 80

| | |
|---|---|
| ctgtagggaa actaaaagag aaatactgga agcaagccat agcagaatat gaaaaacgtt | 60 |
| taggcccata caccaagata gacatcatag aagttccaga cgaaaaagca ccagaaaata | 120 |
| tgagcgacaa agaaatcgag caagtaaaag aaaagaagg ccaacgaata ctagccaaaa | 180 |
| tcaaaccaca atccacagtc attacattag aaatacaagg aaagatgcta tcttccgaag | 240 |
| gattggccca agaattgaac caacgcatga cccaagggca aagcgacttt gtattcgtca | 300 |
| ttggcggatc aaacggcctg cacaaggacg tcttacaacg cagtaactac gcactatcat | 360 |
| tcagcaaaat gacattccca catcaaatga tgcgggttgt gttaattgaa caagtgtaca | 420 |
| gagcatttaa gattatgcgt ggagaagcgt accacaaatg atgcggtttt ttatccagtt | 480 |
| ttttgtttaa tgaacaaggt aaattacgag ataatatttg aagaaaacaa taaagtagag | 540 |
| atggatttcc atatcctctt tagtagcggt tttatctgt aaggtttatt aataattaaa | 600 |
| taaataggcg ggatagttat atatagctta ttaatgaaag aatatgatta ttaatttagt | 660 |
| attatatttt aatattaaaa agaagatatg aaataaattat tcatacccttc caccttacaa | 720 |
| taattagttt tcaatcgaat attaagatta ttagtagtct taaaagttaa gacttcctta | 780 |
| tattaatgac ctaatttatt atttgcctca tgaattatct tttatttct ttgatatgtc | 840 |
| ccaaaccaca tcgtgatata cactacaata aatattatga tgaaactaat aatattctca | 900 |
| aagttcagat ggaaccaacc tgctagaata gcgagtggga agaataggat tatcatcaat | 960 |
| ataaagtgaa ctacagtctg ttttgttata ctccaatcgg tatctgtaaa tatcaaatta | 1020 |

-continued

```
ccataagtaa acaaaattcc aatcaatgcc catagtgcta cacatattag cataataacc   1080
gcttcattaa agttttcata ataaatttta cccataaaag aatctggata tagtggtaca   1140
tatttatccc ttgaaaaaaa taagtgaagt aatgacagaa atcataagac cagtgaacgc   1200
acctttttga acagcgtgga ataattttt catagtgaga tggaccattc catttgtttc   1260
taacttcaag tgatcaatgt aatttagatt gataatttct gattttgaaa tacgcacgaa   1320
tattgaaccg acaagctctt caatttggta aagtcgctga taaagtttta aagctttatt   1380
attcattgtt atcgcatacc tgtttatctt ctactatgaa ctgtgcaatt tgttctagat   1440
caattgggta aacatgatgg ttctgttgca agtaaaaaa atatagctaa ccactaattt   1500
atcatgtcag tgttcgctta acttgctagc atgatgctaa tttcgtggca tggcgaaaat   1560
ccgtagatct gatgagacct gcggttcttt ttatatagag cgtaaataca ttcaatacct   1620
tttaaagtat tctttgctgt attgatactt tgataccttg tctttcttac tttaatatga   1680
cggtgatctt gctcaatgag gttattcaaa tatttcgatg tacaatgaca gtcaggttta   1740
agtttaaaag ctttaattac tttagccatt gctaccttcg ttgaaggtgc ctgatctgta   1800
attacctttt gaggtttacc aaattgttta atgagacgtt taataaacgc atatgctgaa   1860
tgattatctc gttgcttacg caaccaaata tctaatgtat gtccctctgc atcaatggca   1920
cgatataaat agctccattt tccttttatt ttgatgtacg tctcatcaat acgccatttg   1980
taataagctt ttttatgctt tttcttccaa atttgatata aaattggggc atattcttga   2040
acccaacggt agaccgttga atgatgaacg tttacaccac gtccccttaa tatttcagat   2100
atatcacgat aactcaatgc atatcttaga tagtagccaa cggctacagt gat          2153
```

<210> SEQ ID NO 81
<211> LENGTH: 1696
<212> TYPE: DNA
<213> ORGANISM: Staphylococcus aureus

<400> SEQUENCE: 81

```
aaagagaaat attggaagca agccatagca gaatatgaaa aacgtttagg cccatacacc     60
aagatagaca tcatagaagt tccagacgaa aaagcaccag aaaatatgag tgacaaagaa    120
attgagcaag taaagaaaaa agaaggccaa cgaatactag ccaaaatcaa accacaatcc    180
acagtcatta cattagaaat acaaggaaag atgctatctt ccgaaggatt ggcccaagaa    240
ttgaaccaac gcatgaccca agggcaaagc gactttgttt tcgtcattgg cggatcaaac    300
ggcctgcaca aggacgtctt acaacgcagt aactacgcac tatcattcag caaaatgaca    360
ttcccacatc aaatgatgcg ggttgtgtta attgaacaag tgtacagagc atttaagatt    420
atgcgaggag aagcatatca taaatgatgc ggttatttca gccgtaattt tataatataa    480
agcagagttt attaaatttt aatgattact ttttattaag aattaattct agttgatata    540
ttataatgtg aaacacaaaa taataatttg taattgttag tttataggca tctgtatttg    600
gaattttttg tagactattt aaaaaatagt gtatataagt attgagttca tgtattaact    660
gtcttttttc atcgttcatc aagtataagg atgtagagat ttgttggata atttcttcgg    720 atgttttttaa aattatcatt aaattagatg gtatctgatc ttgagttttg ttttagtgt    780 atgtatattt taaaaaattt ttgattgttg ttatttgact ctcttttaat ttgacaccct    840
catcaataaa tgtgttaaat atatcttcat ttgtacttaa atcatcaaaa tttgccaaca    900
aatatttgaa cgtctctaaa tcattatgtt tgagttccgt tttgctattc cataattcca    960
aaccatttgg tagaaagccc aagctgtgat tttgatctcc ccatatagct gaatttaaat   1020
```

-continued

```
cagtgagttg attaattttt tcaacacaga aatgtaattt tggaatgagg aatcgaagtt      1080
gttcttctac ttgctgtact tttcttttgt tttcaataaa atttctacac catactgtta      1140
tcaaaccgcc aattattgtg cacaatcctc caatgattgt agataaaatt gacaatatat      1200
tacacacctt tcttagaggt ttattaacat ctattttga atttaaaatt attactttgg      1260
tagcgttata acctatttaa cagattagag aaaaattgaa tgatcgattg aagaatttcc      1320
aaaataccgt cccatatgcg ttgaaggaga tttctatttt cttctgtatt caaatctttg      1380
gctttatcct ttgctttatt caataaatca tctgagtttt tttcaatatt ttttaataca      1440
tctttggcat tttgtttaaa tactttagga tcggaagtta gggcattaga gtttgccaca      1500
ttaatcatat tattattaat catttgaatt tgattatctg ataatatctc tgataaccta      1560
cgctcatcga ggactttatt aacagtgtct tcaacttgtt gttgtgtgat tgtttatct      1620 tgattttgtt taatatctgc aagttgttct ttaatatctg ctatagaagc atttaaagct      1680
tcatctgaat acccat                                                      1696

<210> SEQ ID NO 82
<211> LENGTH: 991
<212> TYPE: DNA
<213> ORGANISM: Staphylococcus aureus

<400> SEQUENCE: 82
accattttag ctgtagggaa actaaaagag aaatactgga agcaagccat agcagaatat        60
gaaaaacgtt taggcccata caccaagata gacatcatag aagttccaga cgaaaaagca       120
ccagaaaata tgaactacaa agaaattgag caagtaaaag aaaaagaagg ccaacgaata       180
ctagccaaaa tcaaaccaca atcaacagtc attacattag aaatacaagg aaagatgcta       240
tcttccgaag gattggccca agaattgaac caacgcatga cccaagggca aagcgacttt       300
gtattcgtca ttggcggatc aaacggcctg cacaaggacg tcttacaacg cagtaactac       360
gcactatcat tcagcaaaat gacattccca catcaaatga tgcgggttgt gttaattgaa       420
caagtgtaca gagcatttaa gattatgcga ggagaagcgt atcataagtg atggtaaaaa       480
atatgagtaa gtagatgaag agtgaaaatc agattaatta ataataatgt atcaaattta       540
aataaagggg ttttttaagta tgaatttaag aggtcatgaa aatagactta aatttcatgc       600
gaaatatgat gtgacaccta tcacatttt aaaattatta gaaggtcaaa agaaagacgg       660
tgaaggcggc atactgacag atagctatta ctgttttttca tacagcttaa aaggtaattc       720
taaaaaagtt ttaggtacgt ttaattgtgg ttatcatatt gctgaagatt tactaaaatt       780
atcaaatcaa gataaattac ctttatttaa cccgtttaaa gtaattaatg aaggtaatca       840
attgcagggc gtaacgaata aaggtaattt aaatattaat aggcaaagaa aacagtataa       900
tgaagtggct ttacagcttt caaatgctat taatttaatc ataatttgtt atgaggataa       960
tattaaagaa ccactttcaa cgataaaata c                                      991

<210> SEQ ID NO 83
<211> LENGTH: 1108
<212> TYPE: DNA
<213> ORGANISM: Staphylococcus aureus

<400> SEQUENCE: 83
accattttag ctgtagggaa actaaaagag aaatattgga agcaagccat agcagaatat        60
gaaaaacgtt taggcccata caccaagata gacatcatag aagttccaga cgaaaaagca       120
```

-continued

```
ccagaaaata tgagcgacaa agaaattgag caagtaaaag aaaaagaagg ccaacgaata      180
ctagccaaaa tcaaaccaca atccacagtc attacattag aaatacaagg aaagatgcta      240
tcttccgaag gattggccca agaattgaac caacgcatga cccaagggca aagcgacttt      300
gtattcgtca ttggcggatc aaacggcctg cacaaggacg tcttacaacg cagtaactat      360
gcactatcat ttagcaaaat gacattccca catcaaatga tgcgggttgt gttaattgaa      420
caagtgtata gagcatttaa gattatgcgt ggagaagcgt accacaaata aaactaaaaa      480
atatgagaaa attattaaat tagctcaaat ctttgaagaa taaaaagtga atattaagtt      540
tgataattta ggtacaagta aagattaaga atttccatta tttaatacat ggtgtgtaaa      600
tcgacttctt tttgtattag atgtttgcag taagcgatgt aaagaagatg ctaataaata      660
tgtgaggaat gattacgata ctagataagc ggctaatgaa attttttaaa gtacatatat      720
agacatattt ttcatttagt aaaatttga atttcactttt gctaagacta gtgtctagaa       780
atttataatg atttattaac acctatttga aacttaagta taataaatga ttcggatttt      840 attttttaata aagacaaact tgaacgtagc aaagtagttt ttatgataaa taataagttt      900
taataatgtg acgcttttat ataagcacat tattatgaac aatgtgaatt gagcatctac      960
aattacatta ataaatatat aaatgatgat ttaaattcac atatatttat aatacacata     1020
ctatatgaaa gttttgatta tccgaataaa tgctaaaatt aataaaataa ttaaaggaat     1080
catacttatt atacgtatac gtttagct                                         1108
```

<210> SEQ ID NO 84
<211> LENGTH: 1530
<212> TYPE: DNA
<213> ORGANISM: Staphylococcus aureus

<400> SEQUENCE: 84

```
ttagctgtag ggaaactaaa agagaaatat tggaagcaag ccatagcaga atatgaaaaa       60
cgtttaggcc catacaccaa gatagacatc atagaagttc cagacgaaaa agcaccagaa      120
aatatgagcg acaaagaaat tgagcaagta aaagaaaaag aaggccaacg aatactagcc      180
aaaatcaaac cacaatccac agtcattaca ttagaaatac aaggaaagat gctatcttcc      240
gaaggattgg cccaagaatt gaaccaacgc atgacccaag gcaaagcga ctttgtattc      300 gtcattggcg gatcaaacgg cctgcacaag gacgtcttac aacgcagtaa ctatgcacta      360
tcatttagca aaatgacatt cccacatcaa atgatgcggg ttgtgttaat tgaacaagtg      420
tatagagcat ttaagattat gcgtggagaa gcatatcata aatgatgcgg ttttttcagc      480
cgcttcataa agggggtga tcatatcgga acgtatgagg tttatgagaa ttgctgctat      540 gttttatga agcgtatcat aaatgatgca gttttttgata atttttttctt tatcagagat      600 tttactaaaa atcccctcaa agtttgtttt tttcaacttc aactttgaag ggaataaata      660
aggaacttat ttatatttat cctttatctc attaatatct attttttttat taataatatt      720 ataaatatta aattctttag aaaagtcact atcactctta ttcttcatac taaacgttat      780
taatctaata atatcagcta ctatttcttt aaattctatt gcatcttctt ttttataagt      840
agcgcctgta tgaacaattt tatttctcat accatagtaa tctttcatat attttttttac      900 acaattttta atttcattag aattatccaa atctagatta tcaattgtct ttaataaatg      960
atcattaaca acattagcat acccacatcc aagcttcttt tttatctctt catcacttaa     1020
attttcatct aatttataat atcttttctaa aaaatttgtg ataaaaactt ctaatgcagt     1080
ctgaatttgt acaattgcta aattatagtc agatttataa aaagaacgtt caccttttct     1140
```

-continued

```
catagccaaa acataaatat tgctaggatg attattgaaa atattataat ttttttaat      1200 atttaataaa tcactttttt tgatagatga atactgatct tcttctatct ttccaggcat     1260
gtcaatcatg aaaatactca tctcttttat atttccatct atagtatata ttatataata    1320
tggaatactt aatatatccc ctaatgatag ctggtatata ttatgatact gatatttaac    1380
gctaataatt ttaataagat tatttagaca attaaattgc ttattaaaaa ttttcgttag    1440
actattactt ttctttgatt ccctagaagt agaatttgat ttcaattttt taaactgatt    1500
gtgcttgatt attgaagtta tttcaacata                                      1530
```

<210> SEQ ID NO 85
<211> LENGTH: 1256
<212> TYPE: DNA
<213> ORGANISM: Staphylococcus aureus

<400> SEQUENCE: 85

```
gctgtaggga aactaaaaga gaaatattgg aagcaagcca tagcagaata tgaaaaacgt      60
ttaggcccat acaccaagat agacatcata gaagttccag acgaaaaagc accagaaaat    120
atgagcgaca aagaaattga gcaagtaaaa gaaaagaag gccaacgaat actagccaaa     180
attaaaccac aatccacagt cattacatta gaaatacaag gaaagatgct atcttccgaa    240
ggattggccc aagaattgaa ccaacgcatg acccaagggc aaagcgactt tgtattcgtc    300
attggcggat caaacggcct gcacaaggac gtcttacaac gcagtaacta cgcactatca    360
ttcagcaaaa tgacattccc acatcaaatg atgcgggttg tgttaattga gcaagtgtat    420
agagcattta agattatgcg tggagaagca tatcataaat gatgcggttt tttcagccgc    480
ttcataaagg gatttgaat gtatcagaac atatgaggtt tatgtgaatt gctgttatgt    540
ttttaagaag catatcataa gtgatgcggt ttttattaat tagttgctaa aaaatgaagt    600
atgcaatatt aattattatt aaattttgat atatttaaag aaagattaag tttagggtga    660
atgaatggct tatcaaagtg aatatgcatt agaaaatgaa gtacttcaac aacttgagga    720
attgaactat gaaagagtaa atatacataa tattaaatta gaaattaatg aatatctcaa    780
agaactagga gtgttgaaaa atgaataagc agacaaatac tccagaacta agatttccag    840
agtttgatga ggaatggaaa aaaaggaaat taggtgaagt agtaaattat aaaaatggtg    900
gttcatttga aagtttagtg aaaaaccatg gtgtatataa actcataact cttaaatctg    960
ttaatacaga aggaaagttg tgtaattctg gaaaatatat cgatgataaa tgtgttgaaa   1020
cattgtgtaa tgatacttta gtaatgatac tgagcgagca agcaccagga ctagttggaa   1080
tgactgcaat tatacctaat aataatgagt atgtactaaa tcaacgagta gcagcactag   1140
tgcctaaaca atttatagat agtcaatttc tatctaagtt aattaataga aaccagaaat   1200
atttcagtgt gagatctgct ggaacaaaag tgaaaaatat ttctaaagga catgta      1256
```